US007236815B2

(12) United States Patent
Richards-Kortum et al.

(10) Patent No.: US 7,236,815 B2
(45) Date of Patent: *Jun. 26, 2007

(54) METHOD FOR PROBABILISTICALLY CLASSIFYING TISSUE IN VITRO AND IN VIVO USING FLUORESCENCE SPECTROSCOPY

(75) Inventors: Rebecca Richards-Kortum, Austin, TX (US); Nirmala Ramanujam, Philadelphia, PA (US); Anita Mahadevan-Jansen, Nashville, TN (US); Michele Follen, Houston, TX (US); Urs Utzinger, Austin, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 509 days.

This patent is subject to a terminal disclaimer.

(21) Appl. No.: 10/688,152

(22) Filed: Oct. 17, 2003

(65) Prior Publication Data

US 2004/0162489 A1  Aug. 19, 2004

Related U.S. Application Data

(63) Continuation of application No. 09/421,965, filed on Oct. 20, 1999, now abandoned, which is a continuation-in-part of application No. 08/988,840, filed on Dec. 11, 1997, now Pat. No. 6,095,982, which is a continuation of application No. 08/403,446, filed on Mar. 14, 1995, now Pat. No. 5,697,373, said application No. 09/421,965 and a continuation-in-part of application No. 08/693,471, filed on Aug. 2, 1996, now abandoned, and a continuation-in-part of application No. 08/666,021, filed on Jun. 19, 1996, now abandoned.

(51) Int. Cl.
*A61B 6/00*  (2006.01)

(52) U.S. Cl. .................. 600/407; 600/476; 600/477; 436/63; 436/64; 436/813

(58) Field of Classification Search ............... 600/407, 600/473, 475–478; 436/63, 64, 813; 356/301, 356/432; 250/461.2, 459.1
See application file for complete search history.

(56) References Cited

U.S. PATENT DOCUMENTS

| 5,421,339 | A |   | 6/1995  | Ramanujam et al. ........ 600/477 |
| 5,612,540 | A | * | 3/1997  | Richards-Kortum et al. ........ 250/461.2 |
| 5,660,181 | A |   | 8/1997  | Ho et al. .................... 600/408 |
| 5,697,373 | A | * | 12/1997 | Richards-Kortum et al. ........ 600/475 |
| 6,095,982 | A | * | 8/2000  | Richards-Kortum et al. ........ 600/476 |
| 6,135,965 | A | * | 10/2000 | Tumer et al. ................ 600/476 |
| 6,174,291 | B1|   | 1/2001  | McMahon et al. .......... 600/564 |
| 6,241,662 | B1| * | 6/2001  | Richards-Kortum et al. ........ 600/310 |
| 6,258,576 | B1| * | 7/2001  | Richards-Kortum et al. ........ 435/40.52 |

OTHER PUBLICATIONS

Albert and Harris, *Multivariate Interpretation of Clinical Laboratory Data*. Marcel Dekker, New York, 1987.
Alfano et al., "Human breast tissues studied by IR fourier transform Raman spectroscopy," *Lasers in Life Sc*, 4: 23-28, 1991.
Alfano et al., "Optical spectroscopic diagnosis of cancer in normal and breast tissues," *J Optic Soc Am B*, 6:1015-1023, 1989.
American Cancer Society, "Cancer Facts and Figures," 12-13, 1995.
Andersson et al., "Fluorescence imaging and point measurements of tissue: applications to the demarcation of malignant tumors and atherosclerotic lesions from normal tissue," *Photochem Photobiol*, 53:807-14, 1991.
Baraga et al., "Rapid near-infrared Raman spectroscopy of human tissue with a spectrograph and CCD detector." *Appl. Spectr*, 46: 187-190, 1992.
Barrasso et al., "Human papilloma viruses and cervical intraepithelial neoplasia: the role of colposcopy," *Gynecologic Oncology*, 27:197-207, 1987.
Barron et al., "Statistical model of the natural history of cervical carcinoma: II. Estimates of the transition time from dysplasia to carcinoma in situ," *JNCI*, 45:1025-1030, 1970.

Braichotte et al., "Clinical pharmacokinetic studies of photofrin by fluorescence spectroscopy in the oral cavity, the esophagus and the bronchi," *Cancer*, 75:2768-2778, 1995.

Brookner et al., "Safety analysis: relative risk of UV-fluorescence spectroscopy and endoscopy are comparable," *Photochem Photobiol*, 65:1020-1025, 1997.

Burke and Ducatman, *Colposcopy, text and atlas*. Appleton and Large, Norwalk, CT., 1-213, 1991.

Cothren et al., "Gastrointestinal tissue diagnosis by laser induced fluorescence spectroscopy at endoscopy". *Gastrointestinal Endoscopy* 36:105-111, 1990.

Devore, "Probability and Statistics for Engineering and the Sciences". Brooks/Cole, Pacific Grove, 1992.

Dillon and Goldstein, *Multivariate Analysis: Methods and Applications*. John Wiley and Sons, New York, 1984.

Fahey et al., "Meta-analysis of Pap test accuracy," *American J Epidemiology*, 141:680-689,1995.

Farrell and Patterson, "A diffusion theory model of spatially resolved, steady-state diffus reflectance for the non invasive determination of tissue optical properties in vivo," *Medical Physic*, 19:879-888, 1992.

Glassman et al., "Ultraviolet excited fluorescence spectra from non-malignant and malignant tissues of the gynecologic tract," *Lasers in Life Sciences*, 5:49-58, 1992.

Gray et al., "Use of hematoporphyrin derivative in detection and management of cervical cancer," *Am J Obst & Gynec*, 99:766-770, 1967.

Hung et al., "Autofluorescence of normal and malignant bronchial tissue," *Lasers in Surgery and Medicine*, 11:99-105, 1991.

Kapadia et al., "Laser-induced fluorescence spectroscopy of human colonic mucosa," *Gastroenterology*, 99:150-157, 1990.

Kennedy and Pottier, "Endogenous protoporphyrin IX, a clinical useful photosensitizer for photodynamic therapy," *J Photochem Photobiol B:Biol*, 14:275-292, 1992.

Koss, "The Papanicolaou test for cervical cancer detection: a triumph and a tragedy," *JAMA*, 261:737-743, 1989.

Kurman et al., "Interim guidelines of management of abnormal cervical cytology," *JAMA*, 271:1866-1869, 1994.

Lam et al., "Detection and localization of early lung cancer by imaging techniques," *Chest*, 103:12S-14S, 1993.

Lam et al., "Detection of dysplasia and carcinoma in situ by ratio fluorimetry," *Am Rev Respir Dis* 146:1458-1461, 1992.

Liu et al., "Raman, fluorescence and time-resolved light scattering as optical diagnostic techniques to separate diseased and normal biomedical media," *J Photochemistry and Photobiology*, 16:187-209, 1992.

Loh et al., "Oral versus intravenous administration of 5-aminolaevulinic acid for photodynamic therapy," *British Journal of Cancer*, 68:41-51, 1993.

Lohmann et al., "Fluorescence of the cervix uteri as a marker for dysplasia and invasive carcinoma," *European Journal of Obstetrics and Gynecology and Reproductive Biology*, 131:249-253, 1989.

Mahadevan et al., "A study of the fluorescence properties of normal and neoplastic human cervical tissue," *Lasers Surg Med*, 13:647-655, 1993.

Marchesini et al., "Light-induced fluorescence spectroscopy of adenomas, adenocarcinomas and non-neoplastic mucosa in human colon," *J Photochemistry and Photobiology*, 14:219-230, 1992.

Mitchell, "Diagnosis and Treatment of Preinvasive Disease of the Female Lower Genital Tract" *The Cancer Bulletin*, 42:71-76, 1990.

Mitchell, "Accuracy of Colposcopy," *Clinical Consultations in Obstetrics and Gynecology*, 6:70-73, 1994.

Montan and Stromblad, "Spectral characterization of brain tumors utilizing laser-induced fluorescence," *Lasers in Life Sciences*, 1:275-285, 1987.

Ramanujam et al., "Spectroscopic diagnosis of cervical intraepithelial neoplasia (cin) in vivo using laser induced fluorescence spectra at multiple excitation wavelengths," *Lasers Surg Med*, 19:63-74, 1996.

Ramanujam et al., "In vivo diagnosis of cervical intraepithelial neoplasia using 337 excitation," *PNAS*, 91:10193-10197, 1994.

Rava et al., "Early detection of dysplasia in colon and bladder tissue using laser-induced fluorescence," *SPIE* 1426:68-78, 1991.

Reid and Scalzi, "Genital Warts and Cervical Cancer," *Am J Obstet Gynecol*, 153:611-618, 1985.

Reid et al., "Genital warts and cervical cancer," *Am J Obstet Gynecol*, 149:815-823, 1984.

Richards-Kortum et al., "Spectroscopic diagnosis of colonic dysplasia," *Photochem Photobiol*, 53:777-786, 1991.

Schomacker et al., "Ultraviolet laser induced fluorescence of colonic tissue: basic biology and diagnostic potential," *Lasers in Surgery and Medicine*, 12:63-78, 1992.

Schomacker et al., "Ultraviolet laser-induced fluorescence of colonic polyps," *Gastroenterology*, 102:1155-1160, 1992.

Walpole and Myers, *Probability and Statistics for Engineers and Scientists*. Decker, New York., 1987.

Wilkinson, "Pap smears and screening for cervical neoplasia," *Clin Obstet Gynecol*, 33:817-825, 1990.

Wong et al., "Infrared spectroscopy of human cervical cells: evidence of extensive structural changes during carcinogenesis," *Proc Natl Acad Sci USA*, 88:10988-10992, 1991.

World Health Organization, Geneva Cytological Screening in the Control of Cervical Cancer: Technical Guidelines, 1988.

Wright et al., in *Pathology of the Female Genital Tract* (eds. A. Blaustein), 156-326, Springer-Verlag, New York (1994).

Yuanlong et al., "Characteristic autofluorescence for cancer diagnosis and its origin," *Lasers in Surgery and Medicine*, 7:528-532, 1987.

\* cited by examiner

*Primary Examiner*—Ruth S. Smith
(74) *Attorney, Agent, or Firm*—Fulbright & Jaworski L.L.P.

(57) ABSTRACT

Fluorescence spectral data acquired from tissues in vivo or in vitro is processed in accordance with a multivariate statistical method to achieve the ability to probabilistically classify tissue in a diagnostically useful manner, such as by histopathological classification. The apparatus includes a controllable illumination device for emitting electromagnetic radiation selected to cause tissue to produce a fluorescence intensity spectrum. Also included are an optical system for applying the plurality of radiation wavelengths to a tissue sample, and a fluorescence intensity spectrum detecting device for detecting an intensity of fluorescence spectra emitted by the sample as a result of illumination by the controllable illumination device. The system also include a data processor, connected to the detecting device, for analyzing detected fluorescence spectra to calculate a probability that the sample belongs in a particular classification. The data processor analyzes the detected fluorescence spectra using a multivariate statistical method. The five primary steps involved in the multivariate statistical method are (i) preprocessing of spectral data from each patient to account for inter-patient variation, (ii) partitioning of the preprocessed spectral data from all patients into calibration and prediction sets, (iii) dimension reduction of the preprocessed spectra in the calibration set using principal component analysis, (iv) selection of the diagnostically most useful principal components using a two-sided unpaired student's t-test and (v) development of an optimal classification scheme based on logistic discrimination using the diagnostically useful principal component scores of the calibration set as inputs.

32 Claims, 33 Drawing Sheets

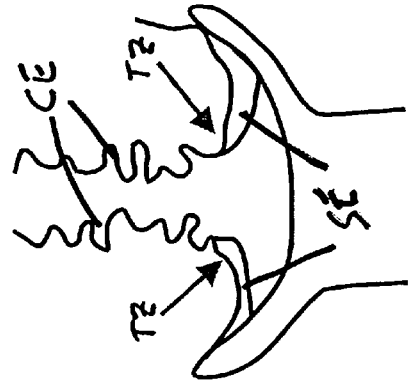
FIG. 22A Neonate
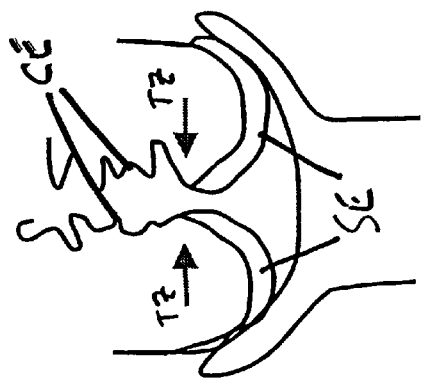
FIG. 22B Premenarchal
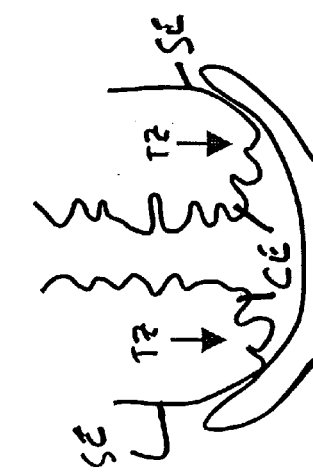
FIG. 22D Menstruating
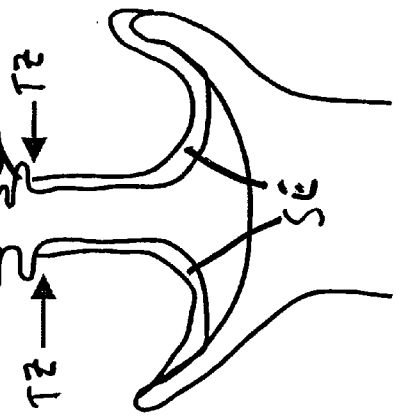
FIG. 22C Menarchal
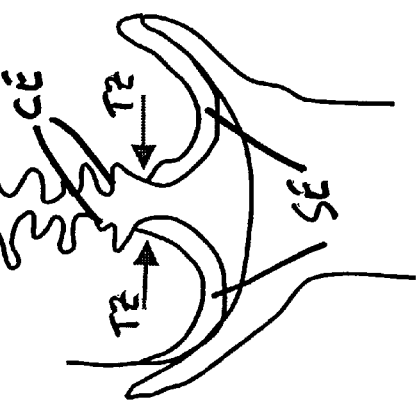
FIG. 22E Menopausal
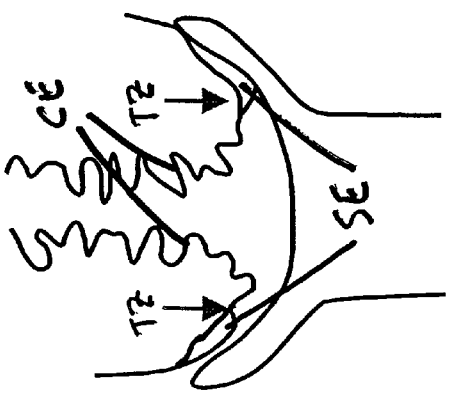
FIG. 22F Postmenopausal

METHOD FOR PROBABILISTICALLY CLASSIFYING TISSUE IN VITRO AND IN VIVO USING FLUORESCENCE SPECTROSCOPY

RELATED APPLICATIONS

This is a continuation of U.S. patent application Ser. No. 09/421,965, filed Oct. 20, 1999, now abandoned, which is a continuation-in-part application of U.S. patent application Ser. No. 08/988,840, filed Dec. 11, 1997, which issued Aug. 1, 2000, as U.S. Pat. No. 6,095,982, which is a continuation of U.S. patent application Ser. No. 08/403,446, filed Mar. 14, 1995, which issued on Dec. 16, 1997, as U.S. Pat. No. 5,697,373; U.S. patent application Ser. No. 09/421,965 is also a continuation-in-part application of U.S. patent application Ser. No. 08/666,021, filed Jun. 19, 1996, now abandoned; and U.S. patent application Ser. No. 09/421,965 is also a continuation-in-part application of U.S. patent application Ser. No. 08/693,471, filed Aug. 2, 1996, now abandoned, which are all hereby incorporated herein by reference in their entirety and serve as a basis for priority for this disclosure.

APPENDICES

Appendices A, B, C and D are included herewith. The Appendices include citations to various references and data. To the extent that these references provide exemplary experimental details or other information supplementary to that set forth herein, they are incorporated herein by reference.

BACKGROUND OF THE INVENTION

1. Field of the Invention

The present invention relates to methods and apparatus of probabilistically classifying tissue in vivo and in vitro using fluorescence spectroscopy, and more particularly to probabilistically classifying normal, cancerous and precancerous epithelial tissue such as cervical tissue in vivo and in vitro using fluorescence spectroscopy.

2. Description of Related Art

Fluorescence, infrared absorption and Raman spectroscopies have been proposed for cancer and precancer diagnosis. Many groups have successfully demonstrated their use in various organ systems. Auto and dye induced fluorescence have shown promise in recognizing atherosclerosis and various types of cancers and precancers. Many groups have demonstrated that autofluorescence may be used for differentiation of normal and abnormal tissues in the human breast and lung, bronchus and gastrointestinal tract. Fluorescence spectroscopic techniques have also been investigated for improved detection of cervical dysplasia.

Although a complete understanding of the quantitative information contained within a tissue fluorescence spectrum has not been achieved, many groups have applied fluorescence spectroscopy for real-time, non-invasive, automated characterization of tissue pathology. Characterization of tissue pathology using auto-fluorescence, see Appendix A, References 10-23, as well as photosensitizer induced fluorescence, see Appendix A, References 25-27, to discriminate between diseased and non-diseased human tissues in vitro and in vivo has been described in a variety of tissues. However, these various approaches have not been entirely satisfactory.

Auto-fluorescence spectra of normal tissue, intraepithelial neoplasia and invasive carcinoma have been measured from several organ sites in vivo. For example, in vivo studies of the human colon at 370 nm excitation (Appendix A, Reference 13) indicated that a simple algorithm based on fluorescence intensity at two emission wavelengths can be used to differentiate normal colon and adenomatous polyps with a sensitivity and specificity of 100% and 97%, respectively. Shomacker et al. (Appendix A, Reference 14) conducted similar studies in vivo at 337 nm excitation and demonstrated that a multivariate linear regression algorithm based on laser induced fluorescence spectra can be used to discriminate between normal colon and colonic polyps with a similarly high sensitivity and specificity. Lam et al. developed a bronchoscope which illuminates tissue at 442 nm excitation and produces a false color image in near real-time which represents the ratio of fluorescence intensities at 520 nm (green) and 690 nm (red) (Appendix A, References 16 and 17). In vivo studies demonstrated that the ratio of red to green auto-fluorescence is greater in normal bronchial tissues than in abnormal bronchial tissues (Appendix A, Reference 16). In a trial with 53 patients, the sensitivity of fluorescence bronchoscopy was found to be 72%, as compared to 50% for conventional white light bronchoscopy (Appendix A, Reference B 17).

Nonetheless, a reliable diagnostic method and apparatus with improved diagnostic capability for use in vitro and in vivo is needed to allow faster, more effective patient management and potentially further reduce mortality.

SUMMARY OF THE INVENTION

The present invention advantageously achieves a real time, non-invasive, and automated method and apparatus for classifying normal, cancerous and precancerous tissue in a diagnostically useful manner, such as by histopathological classifications, to allow faster, more effective patient management and potentially further reduce mortality.

One embodiment of the invention is a method of probabilistically classifying a sample of tissue of a mammalian anatomical structure, tissues of which may have various morphological and biochemical states and are classifiable in accordance therewith. The method comprises illuminating the tissue sample with electromagnetic radiation of a wavelength selected to stimulate in the tissues of the mammalian anatomical structure a fluorescence having spectral characteristics distinguishing between a first plurality of classifications therefor; acquiring fluorescence intensity spectrum sample data for the tissue sample from the illuminating step; obtaining a quantity from fluorescence intensity spectral calibration data, the calibration data being from a calibration set comprising tissues in each one of the first plurality of classifications of a statistically significant set of tissues of the mammalian anatomical structures illuminated with the electromagnetic radiation, and the quantity accounting for a significant amount of variation in the calibration data and showing statistically significant differences between the calibration set tissues in the plurality of classifications; obtaining probability distributions of the calibration data as modified by the quantity for each one of the plurality of classifications; and calculating from the probability distributions and from the sample data as modified by the quantity a probability that the tissue sample belongs in one of the plurality of classifications.

Another embodiment of the invention is a method of probabilistically classifying a sample of tissue of a mammalian anatomical structure, tissues of which may have various morphological and biochemical states and are classifiable in accordance therewith. The method comprises illuminating the tissue sample with electromagnetic radiation of a wavelength selected to stimulate in tissues of the mammalian anatomical structure a fluorescence having spectral characteristics indicative of a classification thereof; detecting a first fluorescence intensity spectrum from the tissue sample resulting from the illuminating step; and calculating a probability that the tissue sample belongs in the classification from a data set comprising the fluorescence intensity spectrum.

A further embodiment of the invention is an apparatus for probabilistically classifying a sample of tissue of a mammalian anatomical structure, tissues of which may have various morphological and biochemical states and are classifiable in accordance therewith. The apparatus comprises a controllable illumination source for generating electromagnetic radiation of a wavelength selected to stimulate in the tissues of the mammalian anatomical structure a fluorescence having spectral characteristics distinguishing between a plurality of classifications therefor; an optical system for illuminating the tissue sample with the electromagnetic radiation and acquiring fluorescence emissions from the tissue sample; a detector for converting the fluorescence emissions from the tissue sample to intensity spectrum sample data; and a processor coupled to the controllable illumination source for control thereof and coupled to the detector for processing the sample data. The processor comprises means for storing a quantity obtained from fluorescence intensity spectral calibration data, the calibration data being from a calibration set comprising tissues in each one of the first plurality of classifications of a statistically significant set of tissues of the mammalian anatomical structures illuminated with the electromagnetic radiation, and the quantity accounting for a significant amount of variation in the calibration data and showing statistically significant differences between the calibration set tissues in the plurality of classifications; means for storing probability distributions of the calibration data as modified by the first quantity for each one of the plurality of classifications; and means for calculating from the probability distributions and from the sample data as modified by the quantity a probability that the tissue sample belongs in one of the first plurality of classifications.

A further embodiment of the invention is a computer program product comprising a computer readable medium having program logic recorded thereon for probabilistically classifying a sample of tissue of a mammalian anatomical structure, tissues of which may have various morphological and biochemical states and are classifiable in accordance therewith. The computer program product comprises means for controlling illumination of the tissue sample with electromagnetic radiation of a wavelength selected to stimulate in the tissues of the mammalian anatomical structure a fluorescence having spectral characteristics distinguishing between a plurality of classifications therefor; means for controlling acquisition of fluorescence intensity spectrum sample data for the tissue sample; a quantity obtained from fluorescence intensity spectral calibration data, the calibration data being from a calibration set comprising tissues in each one of the plurality of classifications of a statistically significant set of tissues of the mammalian anatomical structures illuminated with the electromagnetic radiation, and the quantity accounting for a significant amount of variation in the calibration data and showing statistically significant differences between the calibration set tissues in the plurality of classifications; first probability distributions of the calibration data as modified by the first quantity for each one of the plurality of classifications; and means for calculating from the probability distributions and from the sample data as modified by the quantity a probability that the tissue sample belongs in one of the plurality of classifications.

BRIEF DESCRIPTION OF THE DRAWINGS

FIGS. 22A through 22F illustrate various states of the endocervical canal.

DETAILED DESCRIPTION OF THE PREFERRED EMBODIMENT

Figure 1:
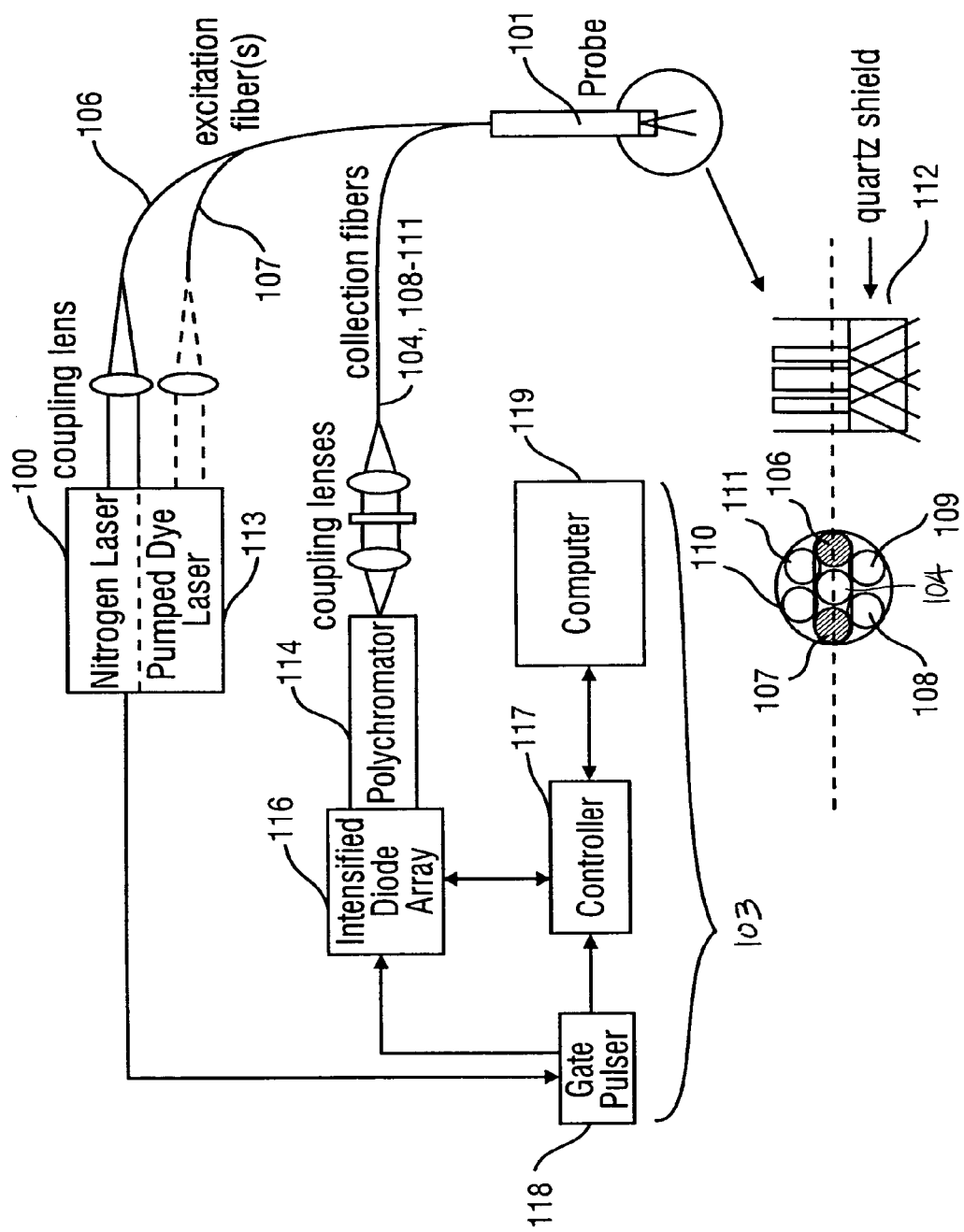
FIG. 1 is a block diagram of an exemplary fluorescence spectroscopy diagnostic apparatus.

Fluorescence spectroscopy has the capability to quickly, non-invasively and quantitatively probe the biochemical and morphological changes that occur as tissue becomes neoplastic. The altered biochemical and morphological state of the neoplastic tissue is reflected in the spectral characteristics of the measured fluorescence. This spectral information can be correlated to tissue histopathology, the current "gold standard" to develop clinically effective screening and diagnostic algorithms. These mathematical algorithms can be implemented in software, thereby enabling automated, fast, non-invasive and accurate pre-cancer screening and diagnosis in the hands of non-experts.

Specifically, fluorescence spectral data acquired from tissues in vivo or in vitro is processed in accordance with a multivariate statistical method to achieve the ability to probabilistically classify tissue in a diagnostically useful manner, such as by histopathological classification. Fluorescence occurs when a fraction of the light absorbed by the tissue is re-radiated at emission wavelengths that are longer than the excitation light. Thus, the apparatus includes a controllable illumination device for emitting electromagnetic radiation selected to cause tissue to produce a fluorescence intensity spectrum. Also included are an optical system for applying the plurality of radiation wavelengths to a tissue sample, and a fluorescence intensity spectrum detecting device for detecting an intensity of fluorescence spectra emitted by the sample as a result of illumination by the controllable illumination device. Optionally, the system may include a data processor, connected to the detecting device, for analyzing detected fluorescence spectra to calculate a probability that the sample is abnormal.

Multivariate Statistical Method

The data processor analyzes the detected fluorescence spectra using a multivariate statistical method. The five primary steps involved in the multivariate statistical method are (i) preprocessing of spectral data from each patient to account for inter-patient variation, (ii) partitioning of the preprocessed spectral data from all patients into calibration and prediction sets, (iii) dimension reduction of the preprocessed spectra in the calibration set using principal component analysis, (iv) selection of the diagnostically most useful principal components using a two-sided unpaired student's t-test and (v) development of an optimal classification scheme based on logistic discrimination using the diagnostically useful principal component scores of the calibration set as inputs. These five individual steps of the multivariate statistical method are discussed below in more detail.

Classification of tissue of a specific patient being diagnosed may be performed by including the patient in the prediction set or by applying the diagnostically most useful principal components and a suitable classification scheme specifically to the spectra from the patient's tissue.

(i) Preprocessing. The objective of preprocessing is to calibrate tissue spectra for inter-patient variation which might obscure differences in the spectra of different tissue types. Four methods of preprocessing were invoked on the spectral data: (a) normalization, (b) mean scaling, (c) a combination of normalization and mean scaling and (d) median scaling.

Spectra were normalized by dividing the fluorescence intensity at each emission wavelength by the maximum fluorescence intensity of that sample. Normalizing a fluorescence spectrum removes absolute intensity information; methods developed from normalized fluorescence spectra rely on differences in spectral line shape information for diagnosis. If the contribution of the absolute intensity information is not significant, two advantages are realized by utilizing normalized spectra. First, it is no longer necessary to calibrate for inter-patient variation of normal tissue fluorescence intensity as in the two-stage method. And second, identification of a colposcopically normal reference site in each patient prior to spectroscopic analysis is no longer needed.

Mean scaling was performed by calculating the mean spectrum for a patient (using all spectra obtained from cervical sites in that patient) and subtracting it from each spectrum in that patient. Mean-scaling can be performed on both unnormalized (original) and normalized spectra. Mean-scaling does not require colposcopy to identify a reference normal site in each patient prior to spectroscopic analysis. However, unlike normalization, mean-scaling displays the differences in the fluorescence spectrum from a particular site with respect to the average spectrum from that patient. Therefore this method can enhance differences in fluorescence spectra between tissue categories most effectively when spectra are acquired from approximately equal numbers of non diseased and diseased sites from each patient.

Median scaling is performed by calculating the median spectrum for a patient (using all spectra obtained from cervical sites in that patient) and subtracting it from each spectrum in that patient. Like mean scaling, median scaling can be performed on both unnormalized (original) and normalized spectra, and median scaling does not require colposcopy to identify a reference normal site in each patient prior to spectroscopic analysis. However, unlike mean scaling, median scaling does not require the acquisition of spectra from equal numbers of non diseased and diseased sites from each patient.

(ii) Calibration and Prediction Data Sets. The preprocessed spectral data were randomly assigned into either a calibration or prediction set. The multivariate statistical method was developed and optimized using the calibration set. It was then tested prospectively on the prediction data set.

(iii) Principal Component Analysis. Principal component analysis (PCA) is a linear model which transforms the original variables of a fluorescence emission spectrum into a smaller set of linear combinations of the original variables called principal components that account for most of the variance of the original data set. Principal component analysis is described in Dillon W. R., Goldstein M., *Multivariate Analysis: Methods and Applications*, John Wiley and Sons, 1984, pp. 23-52, the disclosure of which is expressly incorporated herein by reference. While PCA may not provide direct insight to the morphologic and biochemical basis of tissue spectra, it provides a novel approach of condensing all the spectral information into a few manageable components, with minimal information loss. Furthermore, each principal component can be easily related to the original emission spectrum, thus providing insight into diagnostically useful emission variables.

Prior to PCA, a data matrix is created where each row of the matrix contains the preprocessed fluorescence spectrum of a sample and each column contains the pre-processed fluorescence intensity at each emission wavelength. The data matrix D (RC), consisting of R rows (corresponding to r total samples from all patients in the training set) and C columns (corresponding to intensity at c emission wavelengths) can be written as:

$$D = \begin{pmatrix} D_{11} D_{12} \ldots D_{1c} \\ D_{21} D_{22} \ldots D_{2c} \\ \\ D_{r1} D_{r2} \ldots D_{rc} \end{pmatrix} \quad (1)$$

The first step in PCA is to calculate the covariance matrix, Z. First, each column of the preprocessed data matrix D is mean-scaled. The mean-scaled preprocessed data matrix, $D_m$ is then multiplied by its transpose and each element of the resulting square matrix is divided by (r−1), where r is the total number of samples. The equation for calculating Z is defined as:

$$Z = \frac{1}{r-1}(D_m/D_m) \quad (2)$$

The square covariance matrix, Z (c×c) is decomposed into its respective eigenvalues and eigenvectors. Because of experimental error, the total number of eigenvalues will always equal the total number of columns (c) in the data matrix D assuming that c<r. The goal is to select n<c eigenvalues that can describe most of the variance of the original data matrix to within experimental error. The variance, V accounted for by the first n eigenvalues can be calculated as follows:

$$V = 100 \left( \frac{\sum_{j=1}^{n} \lambda_j}{\sum_{j=1}^{c} \lambda_j} \right) \quad (3)$$

The criterion used in this analysis was to retain the first n eigenvalues and corresponding eigenvectors that account for 99% of the variance in the original data set.

Next, the principal component score matrix can be calculated according to the following equation:

$$R = DC \quad (4)$$

where, D (r×c) is the preprocessed data matrix and C (c×n) is a matrix whose columns contain the n eigenvectors which correspond to the first n eigenvalues. Each row of the score matrix R (r×c) corresponds to the principal component scores of a sample and each column corresponds to a principal component. The principal components are mutually orthogonal to each other.

Finally, the component loading is calculated for each principal component. The component loading represents the correlation between the principal component and the variables of the original fluorescence emission spectrum. The component loading can be calculated as shown below:

$$CL_{ij} = \frac{C_{ij}}{\sqrt{S_{ii}}} \sqrt{\lambda_j} \quad (5)$$

where, $CL_{ij}$ represents the correlation between the ith variable (preprocessed intensity at ith emission wavelength) and the jth principal component. $C_{ij}$ is the ith component of the jth eigenvector, $\lambda_j$ is the jth eigenvalue and $S_{ii}$ is the variance of the ith variable.

Principal component analysis was performed on each type of preprocessed data matrix, described above. Eigenvalues accounting for 99% of the variance in the original preprocessed data set were retained. The corresponding eigenvectors were then multiplied by the original data matrix to obtain the principal component score matrix R.

(iv) Student's T-Test. Average values of principal component scores were calculated for each histo-pathologic tissue category for each principal component obtained from the preprocessed data matrix. A two-sided unpaired student's t-test was employed to determine the diagnostic contribution of each principal component. Such a test is disclosed in Devore J. L., *Probability and Statistics for Engineering and the Sciences*, Brooks/Cole, 1992, and in Walpole R. E., Myers R. H., *Probability and Statistics for Engineers and Scientists*, Macmillan Publishing Co., 1978, Chapter 7, the disclosures of which are expressly incorporated herein by reference. The hypothesis that the means of the principal component scores of two tissue categories are different were tested for 1) normal squamous epithelia and SILs, 2) columnar normal epithelia and SILs and 3) inflammation and SILs. The t-test was extended a step further to determine if there are any statistically significant differences between the means of the principal component scores of high grade SILs and low grade SILs. Principal components for which the hypothesis stated above were true below the 0.05 level of significance were retained for further analysis.

(v) Logistic Discrimination. Logistic discriminant analysis is a statistical technique that can be used to develop diagnostic methods based on posterior probabilities, overcoming the drawback of the binary decision scheme employed in the two-stage method. This statistical classification method is based on Bayes theorem and can be used to calculate the posterior probability that an unknown sample belongs to each of the possible tissue categories identified. Logistic discrimination is discussed in Albert A., Harris E. K., *Multivariate Interpretation of Clinical Laboratory Data*, Marcel Dekker, 1987, the disclosure of which is expressly incorporated herein by reference. Classifying the unknown sample into the tissue category for which its posterior probability is highest results in a classification scheme that minimizes the rate of misclassification.

For two diagnostic categories, $G_1$ and $G_2$, the posterior probability of being a member of $G_1$, given measurement x, according to Bayes theorem is:

$$P(G_1 \mid x) = \frac{P(x \mid G_1) P(G_1) C(2 \mid 1)}{P(x \mid G_1) P(G_1) C(2 \mid 1) + P(x \mid G_2) P(G_2) C(1 \mid 2)} \quad (6)$$

where $P(x|G_i)$ is the conditional joint probability that a tissue sample of type i will have principal component score x, and $P(G_i)$ is the prior probability of finding tissue type i in the sample population. C(j|i) is the cost of misclassifying a sample into group j when the actual membership is group i.

The prior probability $P(G_i)$ is an estimate of the likelihood that a sample of type i belongs to a particular group when no information about it is available. If the sample is considered representative of the population, the observed proportions of cases in each group can serve as estimates of the prior probabilities. In a clinical setting, either historical incidence figures appropriate for the patient population can be used to generate prior probabilities, or the practitioner's colposcopic assessment of the likelihood of precancer can be used to estimate prior probabilities.

The conditional probabilities can be developed from the probability distributions of the n principal component scores for each tissue type, i. The probability distributions can be modeled using various techniques. For example, one technique is the gamma function, which is characterized by two parameters, alpha and beta, which are related to the mean and standard deviation of the data set. The Gamma function is typically used to model skewed distributions and is defined below:

$$f(x; \alpha, \beta) = \frac{1}{\beta^\alpha \Gamma(\alpha)} x^{\alpha-1} e^{-\frac{x}{\beta}} \quad (7)$$

The gamma function can be used to calculate the conditional probability that a sample from tissue type i, will exhibit the principal component score, x. If more than one principal component is needed to describe a sample population, then the conditional joint probability is simply the product of the conditional probabilities of each principal component (assuming that each principal component is an independent variable) for that sample population.

Another technique is the normal probability density function, see Appendix A, Reference 31, which is characterized by μ (mean) and ' (standard deviation).

Use of the multivariate statistical method in four illustrative diagnostic methods is described below in the following four examples.

FIRST EXAMPLE

Instrumentation

Fluorescence spectra were recorded with a spectroscopic system incorporating a pulsed nitrogen pumped dye laser, an optical fiber probe and an optical multi-channel analyzer at colposcopy. The laser characteristics for the study were: 337, 380 and 460 nm wavelengths, transmitted pulse energy of 50 uJ, a pulse duration of 5 ns and a repetition rate of 30 Hz. The probe includes 2 excitation fibers, one for each wavelength and 5 collection fibers. Rhodamine 6G (8 mg/ml) was used as a standard to calibrate for day to day variations in the detector throughput. The spectra were background subtracted and normalized to the peak intensity of rhodamine. The spectra were also calibrated for the wavelength dependence of the system.

FIG. 1 is an exemplary spectroscopic system for collecting and analyzing fluorescence spectra from cervical tissue. The system incorporates a pulsed nitrogen pumped dye laser 100, an optical fiber probe 101 and an optical multi-channel analyzer 103 utilized to record fluorescence spectra from the intact cervix at colposcopy. The probe 101 comprises a central fiber 104 surrounded by a circular array of six fibers. All seven fibers have the same characteristics (0.22 NA, 200 micron core diameter). Two of the peripheral fibers, 106 and 107, deliver excitation light to the tissue surface; fiber 106 delivers excitation light from the nitrogen laser and fiber 107 delivers light from the dye module (overlap of the illumination area viewed by both optical fibers 106, 107 is greater than 85%). The purpose of the remaining five fibers (104 and 108-111) is to collect the emitted fluorescence from the tissue surface directly illuminated by each excitation fibers 106, 107. A quartz shield 112 is placed at the tip of the probe 101 to provide a substantially fixed distance between the fibers and the tissue surface, so fluorescence intensity can be reported in calibrated units.

Excitation light at 337 nm excitation was focused into the proximal end of excitation fiber 106 to produce a 1 mm diameter spot at the outer face of the shield 112. Excitation light from the dye module 113, coupled into excitation fiber 107 was produced by using appropriate fluorescence dyes; in this example, BBQ (1E-03M in 7 parts toluene and 3 parts ethanol) was used to generate light at 380 nm excitation, and Coumarin 460 (1E-02 M in ethanol) was used to generate light at 460 nm excitation. The average transmitted pulse energy at 337, 380 and 460 nm excitation were 20, 12 and 25 mJ, respectively. The laser characteristics for this example are: a 5 ns pulse duration and a repetition rate of 30 Hz, however other characteristics would also be acceptable. Excitation fluences should remain low enough so that cervical tissue is not vaporized and so that significant photo-bleaching does not occur. In arterial tissue, for example, significant photo-bleaching occurs above excitation fluences of 80 mJ/mm.

The proximal ends of the collection fibers 104, 108-111 are arranged in a circular array and imaged at the entrance slit of a polychromator 114 (Jarrell Ash, Monospec 18) coupled to an intensified 1024-diode array 116 controlled by a multi-channel analyzer 117 (Princeton Instruments, OMA). 370, 400 and 470 nm long pass filters were used to block scattered excitation light at 337, 380 and 460 nm excitation respectively. A 205 ns collection gate, synchronized to the leading edge of the laser pulse using a pulser 118 (Princeton Instruments, PG200), effectively eliminated the effects of the colposcope's white light illumination during fluorescence measurements. Data acquisition and analysis were controlled by computer 119 in accordance with the fluorescence diagnostic method described below in more detail with reference to the flowcharts of FIGS. 2A-2C.

Method

1. SILs vs. Normal Squamous Tissue at 337 nm excitation. A summary of the fluorescence diagnostic method developed and tested in a previous group of 92 patients (476 sites) is presented here. The spectral data were preprocessed by normalizing each spectrum to a peak intensity of one, followed by mean-scaling. Mean scaling is performed by calculating the mean spectrum for a patient (using all spectra obtained from cervical sites in that patient) and subtracting it from each spectrum in that patient. Next, principal component analysis (PCA) is used to transform the original variables of each preprocessed fluorescence emission spectrum into a smaller set of linear combinations called principal components that account for 99% of the variance of the original data set. Only the diagnostically useful principal components are retained for further analysis. Posterior probabilities for each tissue type are determined for all samples in the data set using calculated prior and conditional joint probabilities. The prior probability is calculated as the percentage of each tissue type in the data. The conditional probability was calculated from the gamma function which modeled the probability distributions of the retained principal components scores for each tissue category. The entire data set was split in two groups: calibration and prediction data set such that their prior probabilities were approximately equal. The method is optimized using the calibration set and then implemented on the prediction set to estimate its performance in an unbiased manner. The methods using PCA and Bayes theorem were developed using the calibration set consisting of previously collected spectra from 46 patients (239 sites). These methods were then applied to the prediction set (previously collected spectra from another 46 patients; 237 sites) and the current data set of 36 samples.

More specifically, at 337 nm excitation, fluorescence spectra were acquired from a total of 476 sites in 92 patients. The data were randomly assigned to either a calibration set or prediction set with the condition that both sets contain roughly equal number of samples from each histo-pathologic category, as shown in Table 1. Table 1A shows the histo-pathologic classification of samples in the training and the validation set examined at 337 nm excitation, and Table 1B shows the histological classification of cervical samples spectroscopically interrogated in vivo from 40 patients at 380 nm excitation and 24 patients in 460 nm excitation.

TABLE 1A

| Histology | Training Set | Validation Set |
| --- | --- | --- |
| Squamous Normal | 127 | 126 |
| Columnar Normal | 25 | 25 |
| Inflammation | 16 | 16 |
| Low Grade SIL | 40 | 40 |
| High Grade SIL | 31 | 30 |

TABLE 1B

| Histology | 380 nm excitation (40 patients) | 460 nm excitation (24 patients) |
| --- | --- | --- |
| Squamous Normal | 82 | 76 |
| Columnar Normal | 20 | 24 |
| Inflammation | 10 | 11 |
| Low Grade SIL | 28 | 14 |
| High Grade SIL | 15 | 22 |

The random assignment ensured that not all spectra from a single patient were contained in the same data set. The purpose of the calibration set is to develop and optimize the method and the purpose of the prediction set is to prospectively test its accuracy in an unbiased manner. The two-stage method and the multivariate statistical method were optimized using the calibration set. The performance of these methods were then tested prospectively on the prediction set.

Principal component analysis of mean-scaled normalized spectra at 337 nm excitation from the calibration data set resulted in three principal components accounting for 99% of the total variance. Only, the first two principal components obtained from the preprocessed data matrix containing mean-scaled normalized spectra demonstrate the statistically most significant differences ($P<0.05$) between normal squamous tissues and SILs (PC1: $P<1E-25$, PC2: $P<0.006$). The two-tail P values of the scores of the third principal component were not statistically significant ($P<0.2$). Therefore, the rest of the analysis was performed using these two principal components. All of the principal components are included in Appendix D.

For excitation at 337 nm, the prior probability was determined by calculating the percentage of each tissue type in the calibration set: 65% normal squamous tissues and 35% SILs. More generally, prior probabilities should be selected to describe the patient population under study; the values used here are appropriate as they describe the prediction set as well.

Figure 3:
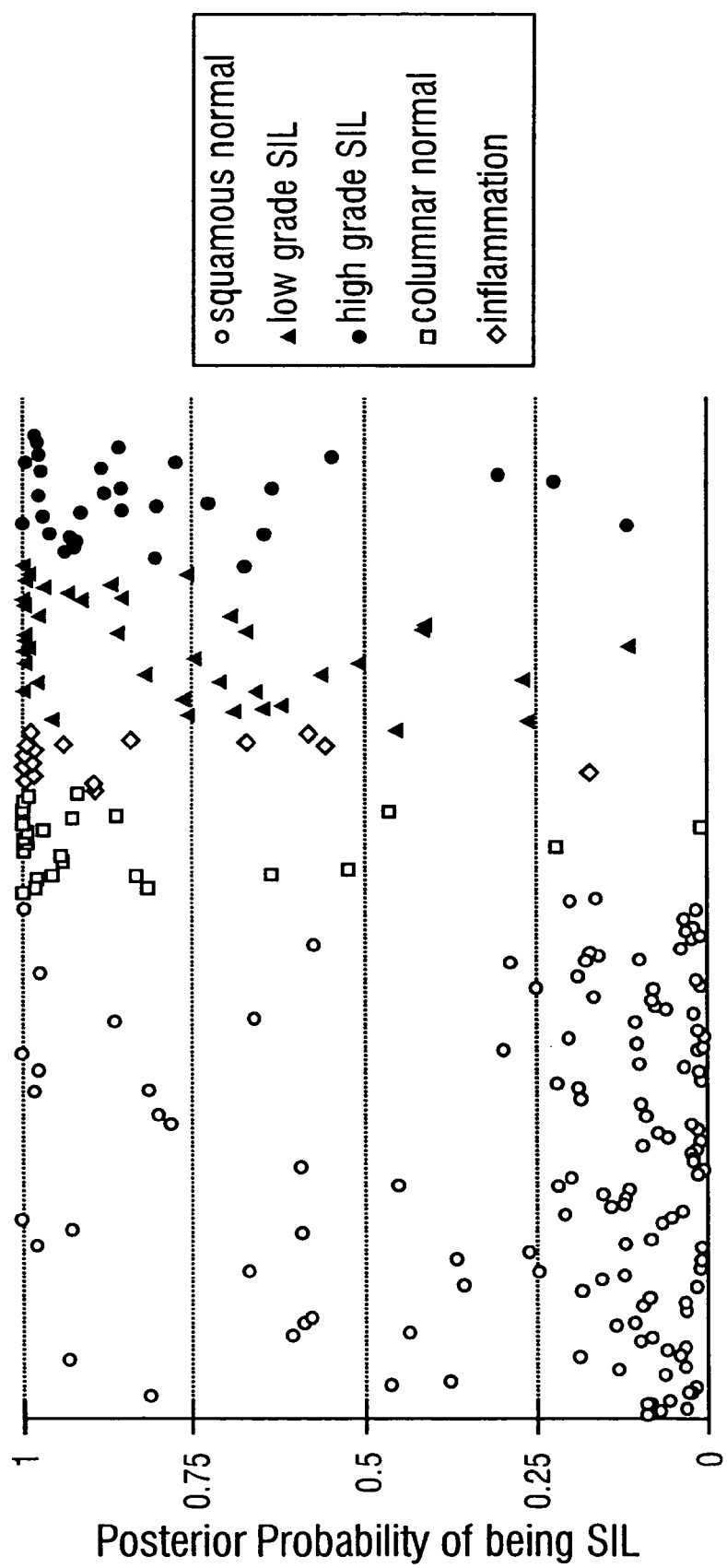
FIGS. 3 and 4 are graphs depicting the performance of the first exemplary fluorescence diagnostic method with 337 nm excitation.

Posterior probabilities of belonging to each tissue type (normal squamous or SIL) were calculated for all samples in the calibration set, using the known prior probabilities and the conditional probabilities calculated from the gamma function. A cost of misclassification of SILs equal to 0.5 was assumed. FIG. 3 illustrates the posterior probability of belonging to the SIL category. The posterior probability is plotted for all samples in the calibration set. This plot indicates that 75% of the high grade SILs have a posterior probability greater than 0.75 and almost 90% of high grade SILs have a posterior probability greater than 0.6. While 85% of low grade SILs have a posterior probability greater than 0.5, only 60% of low grade SILs have a posterior probability greater than 0.75. More than 80% of normal squamous epithelia have a posterior probability less than 0.25. Note that evaluation of normal columnar epithelia and samples with inflammation using this method results in classifying them as SILs.

Figure 4:
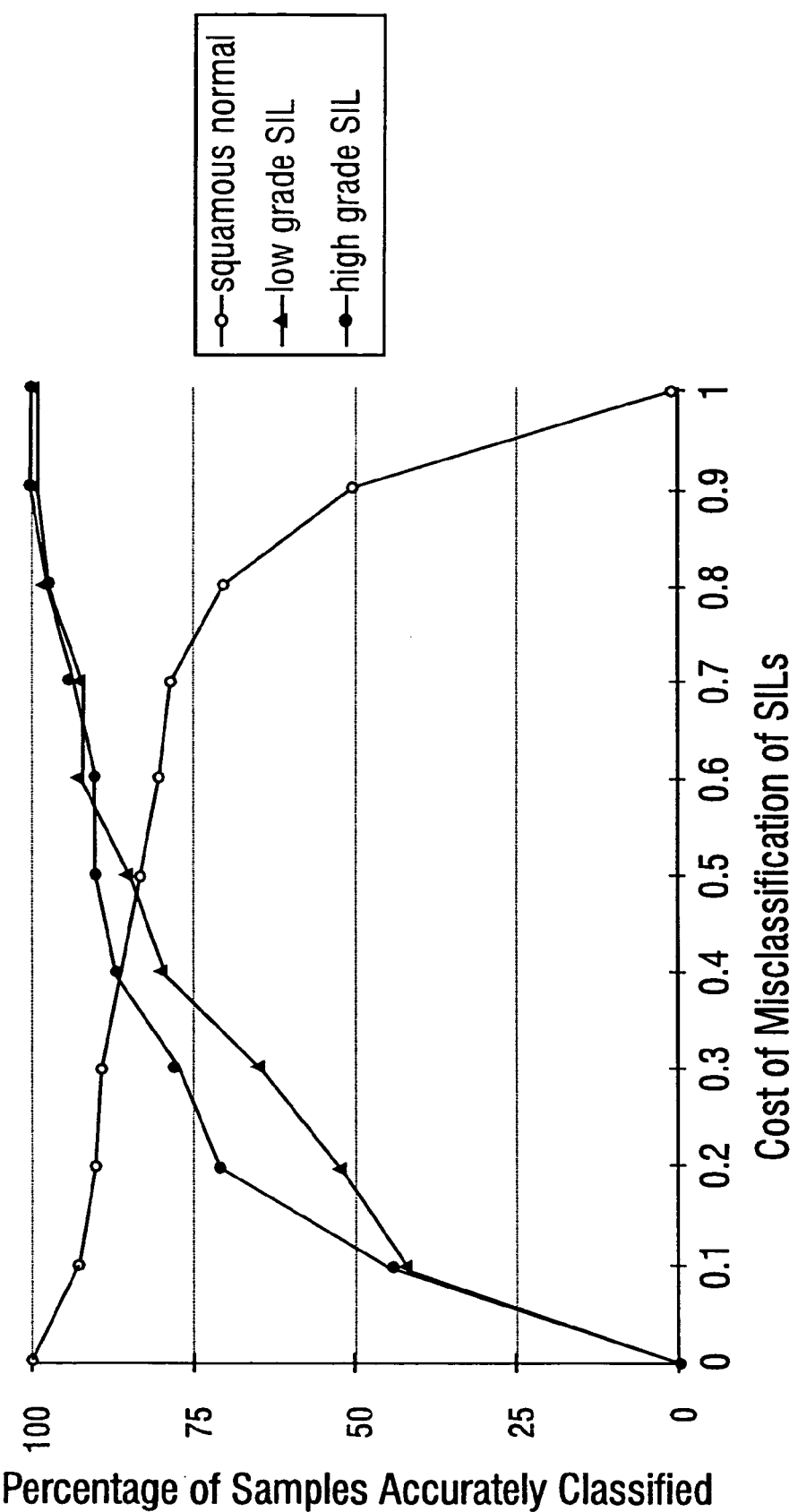

FIG. 4 shows the percentage of normal squamous tissues and SILs correctly classified versus cost of misclassification of SILs for the data from the calibration set. An increase in the SIL misclassification cost results in an increase in the proportion of correctly classified SILs and a decrease in the proportion of correctly classified normal squamous tissues. Note, that varying the cost from 0.4 to 0.6 alters the classification accuracy of both SILs and normal tissues by less than 15% indicating that a small change in the cost does not significantly alter the performance of the method. An optimal cost of misclassification would be 0.6-0.7 as this correctly classifies almost 95% of SILs and 80% of normal squamous epithelia, for the prior probabilities used and is not sensitivity to small changes in prior probability.

The method was implemented on mean-scaled spectra of the prediction set, to obtain an unbiased estimate of its accuracy. The two eigenvectors obtained from the calibration set were multiplied by the prediction matrix to obtain the new principal component score matrix. Using the same prior probabilities, a cost of misclassification of SILs equal to 0.5, and conditional joint probabilities calculated from the gamma function, all developed from the calibration set, Bayes rule was used to calculate the posterior probabilities for all samples in the prediction set.

Confusion matrices in Tables 2A and 2B show the results of the multivariate statistical method applied to the entire fluorescence emission spectra of squamous normal tissues and SILs at 337 n.m excitation in the calibration set and the prediction set, respectively. A comparison of the sample classification between the prediction and calibration sets indicates that the method performs within 7% on an unknown data set of approximately equal prior probability.

TABLE 2A

| Classification | Squamous Normal | Low Grade SIL | High Grade SIL |
| --- | --- | --- | --- |
| Squamous Normal | 83% | 15% | 10% |
| SIL | 17% | 85% | 90% |

TABLE 2B

| Classification | Squamous Normal | Low Grade SIL | High Grade SIL |
| --- | --- | --- | --- |
| Squamous Normal | 81% | 22% | 6% |
| SIL | 19% | 78% | 94% |

The utility of another parameter called the component loadings was explored for reducing the number of emission variables required to achieve classification with minimal decrease in predictive ability. Portions of the emission spectrum most highly correlated (correlation >0.9 or <0.9) with the component loadings were selected and the reduced data matrix was used to regenerate and evaluate the method. Using intensity at 2 emission wavelengths, the method was developed in an identical manner as was done with the entire emission spectrum. It was optimized using the calibration set and implemented on the prediction set. A comparison of the sample classification based on the method using the entire emission spectrum to that using intensity at 2 emission wavelengths indicates that the latter method performs equally well in classifying normal squamous epithelia and low grade SILs. The performance of the latter method is 6% lower for classifying high grade SILs.

2. SILs vs. Normal Columnar Epithelia and Inflammation at 380 nm Excitation. Principal components obtained from the preprocessed data matrix containing mean-scaled normalized spectra at 380 nm excitation could be used to differentiate SILs from non diseased tissues (normal columnar epithelia and inflammation). The principal components are included in Appendix D. Furthermore, a two-sided unpaired t-test indicated that only principal component 2 (PC2) and principal component 5 (PC5) demonstrated the statistically most significant differences (p<0.05) between SILs and non diseased tissues (normal columnar epithelia and inflammation). The p values of the remaining principal component scores were not statistically significant (p>0.13). Therefore, the rest of the analysis was performed using these two principal components which account collectively for 32% of the variation in the original data set.

Figure 5A:
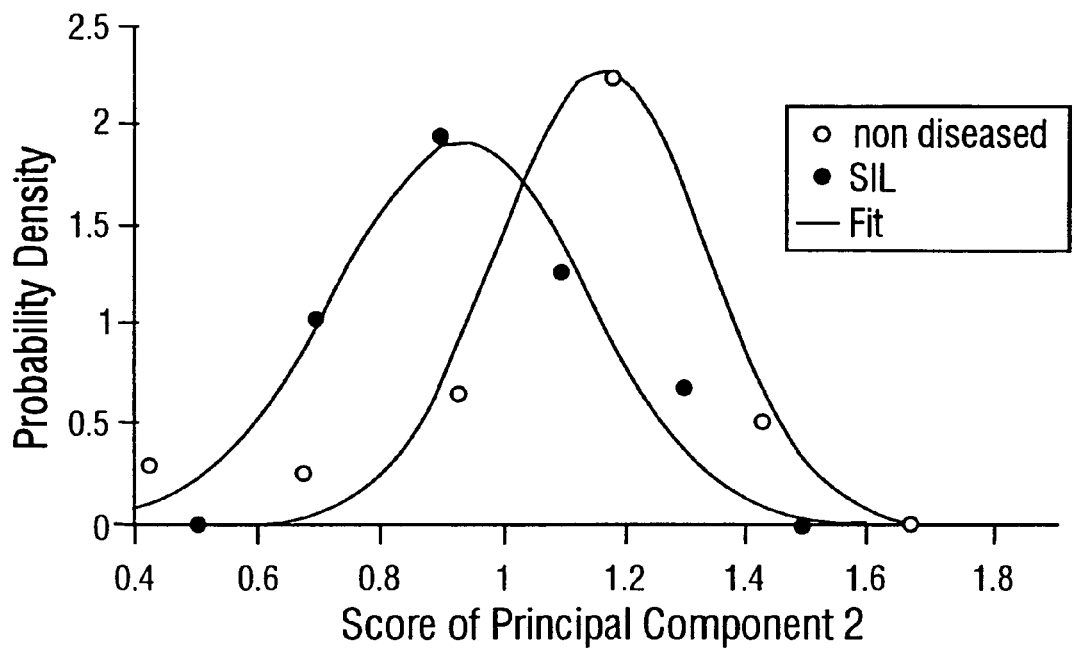
FIGS. 5A, 5B and 6 are graphs illustrating the performance of the first fluorescence spectrum diagnostic method at 380 nm excitation.
Figure 5B:
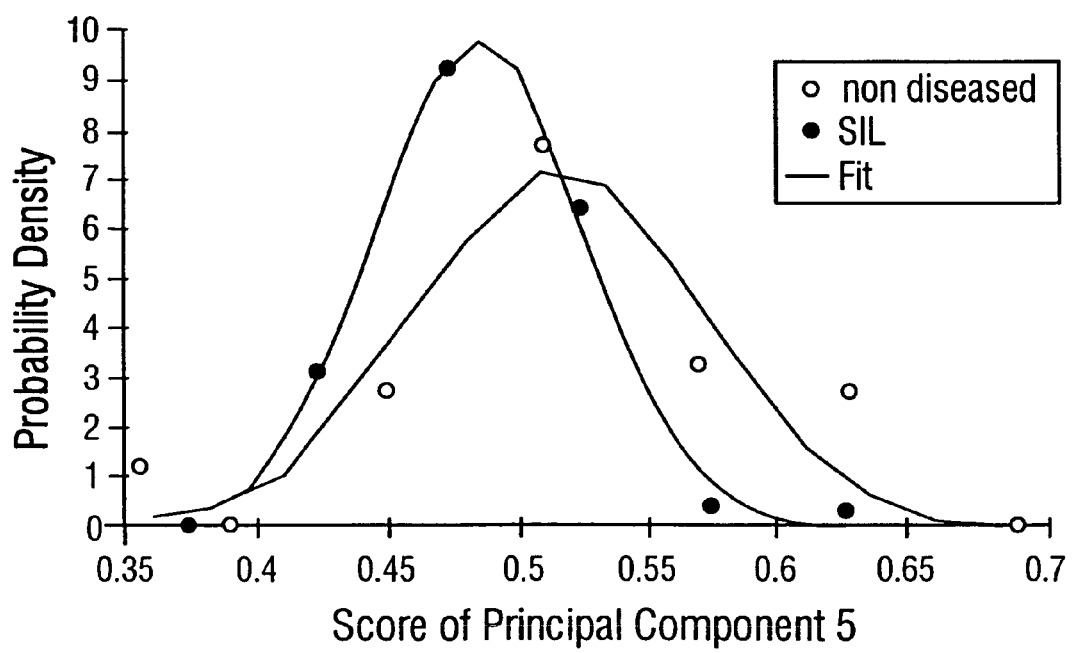
Figure 6:
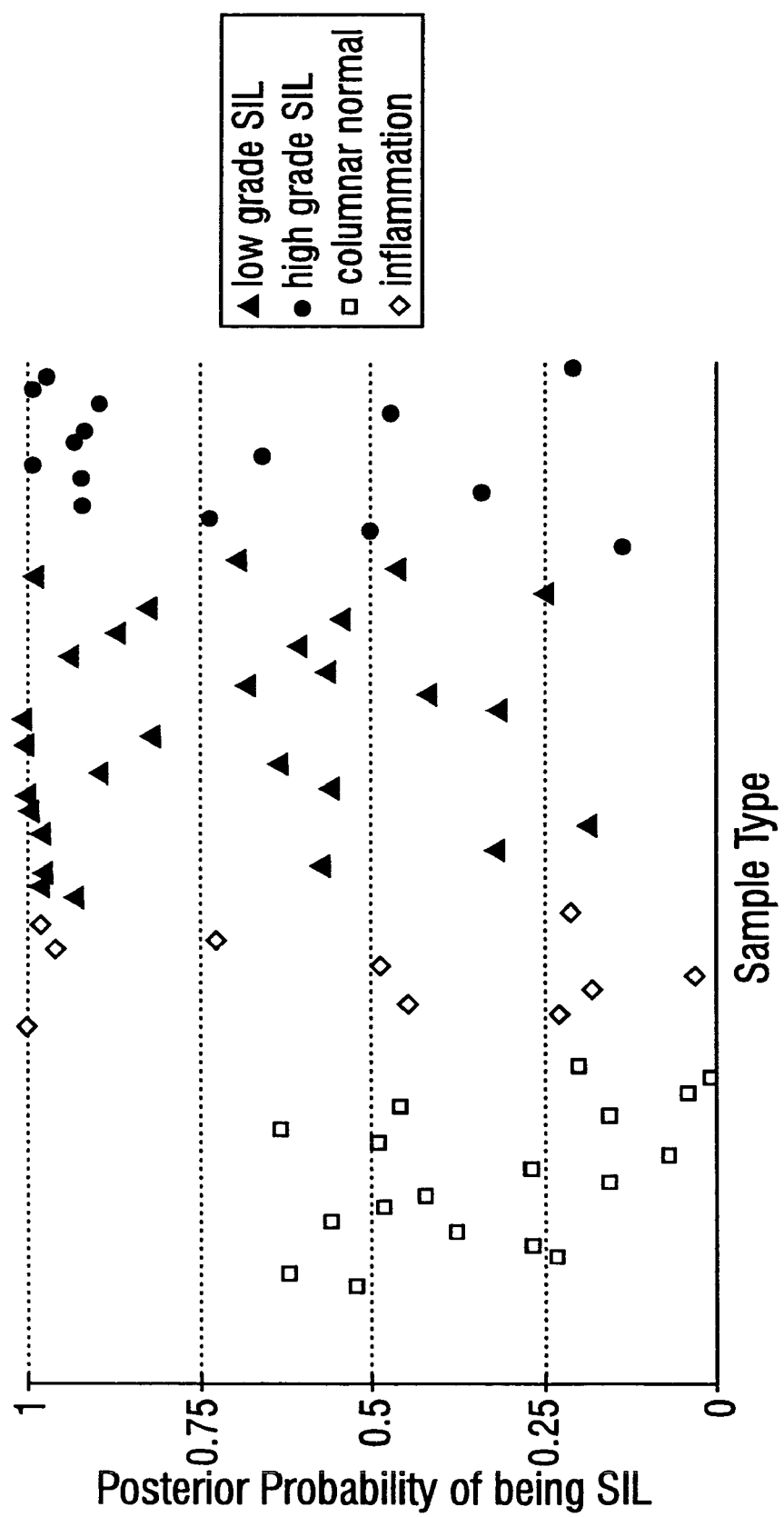

FIGS. 5A and 5B illustrate the measured probability distribution and the best fit of the normal probability density function to PC2 and PC5 of non diseased tissues and SILs, respectively. There is reasonable agreement between the measured and calculated probability distribution, for each case. The prior probability was determined by calculating the percentage of each tissue type in the data set: 41% non diseased tissues and 59% SILs. Posterior probabilities of belonging to each tissue type were calculated for all samples in the data set, using the known prior probabilities and the conditional joint probabilities calculated from the normal probability density function. FIG. 6 illustrates the retrospective performance of the diagnostic method on the same data set used to optimize it. The posterior probability of being classified into the SIL category is plotted for all samples evaluated. The results shown are for a cost of misclassification of SILs equal to 50%. FIG. 6 indicates that 78% of SILs have a posterior probability greater than 0.5, 78% of normal columnar tissues have a posterior probability less than 0.5 and 60% of samples with inflammation have a posterior probability less than 0.5. Note that, there are only 10 samples with inflammation in this study.

Tables 3A and 3B compare (a) the retrospective performance of the diagnostic method on the data set used to optimize it to (b) a prospective estimate of the method's performance using cross-validation. The method uses mean-scaled normalized spectra at 380 nm excitation to differentiate SILs from non diseased tissues (normal columnar epithelia and inflammation). Table 3A indicates that for a cost of misclassification of 50%, 74% of high grade SILs, 78% of low grade SILs, 78% of normal columnar samples and 60% of samples with inflammation are correctly classified. The unbiased estimate of the method's performance in Table 3B indicates that there is no change in the percentage of correctly classified SILs and approximately only a 10% decrease in the proportion of correctly classified normal columnar samples.

TABLE 3A

| Classification | Normal Columnar | Inflammation | Low Grade SIL | High Grade SIL |
| --- | --- | --- | --- | --- |
| Non diseased | 78% | 60% | 21% | 26% |
| SIL | 22% | 40% | 79% | 74% |

TABLE 3B

| Classification | Normal Columnar | Inflammation | Low Grade SIL | High Grade SIL |
| --- | --- | --- | --- | --- |
| Non diseased | 65% | 30% | 22% | 26% |
| SIL | 35% | 70% | 78% | 74% |

3. Squamous Normal Tissue vs. SILs at 460 n.m Excitation. Principal components obtained from the preprocessed data matrix containing mean-scaled normalized spectra at 460 nm excitation could be used to differentiate SIL from normal squamous tissue. These principal components are included in Appendix D. Only principal components 1 and 2 demonstrated the statistically most significant differences (p<0.05) between SILs and normal squamous tissues. The p values of the remaining principal component scores, were not statistically significant (p>0.06). Therefore, the rest of the analysis was performed using these two principal components which account collectively for 75% of the variation in the original data set.

Figure 7A:
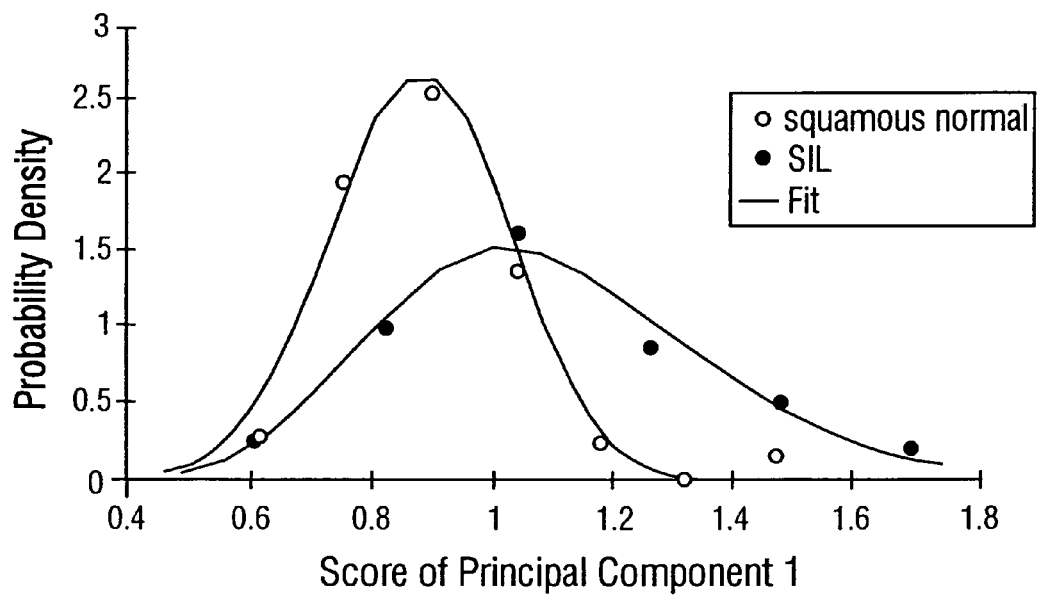
FIGS. 7A, 7B and 8 are graphs illustrating the performance of the first fluorescence spectrum diagnostic method to distinguish squamous normal tissue from SIL at 460 nm excitation.
Figure 7B:
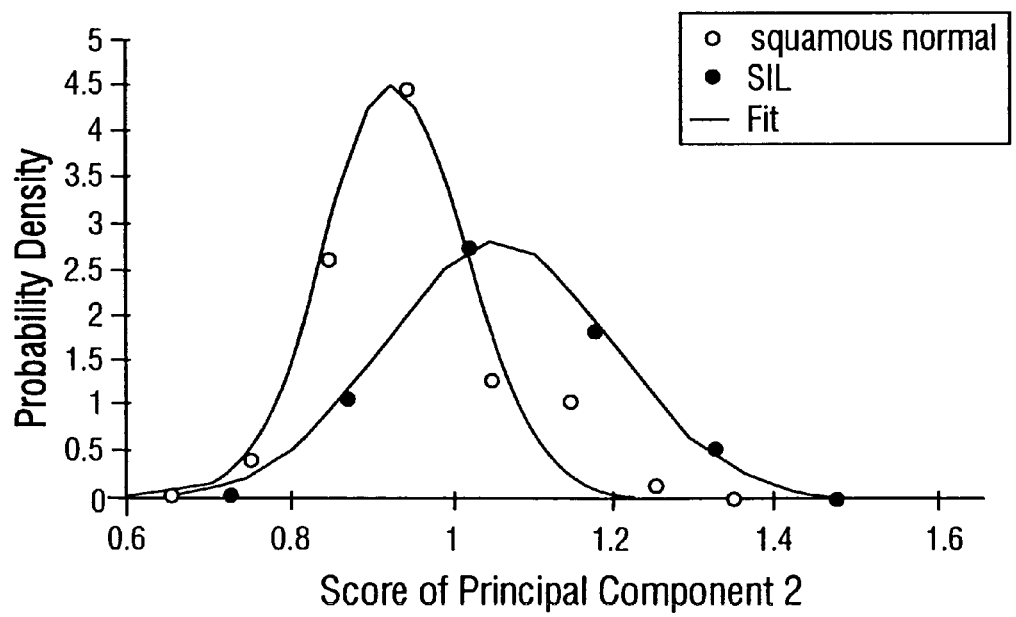
Figure 8:
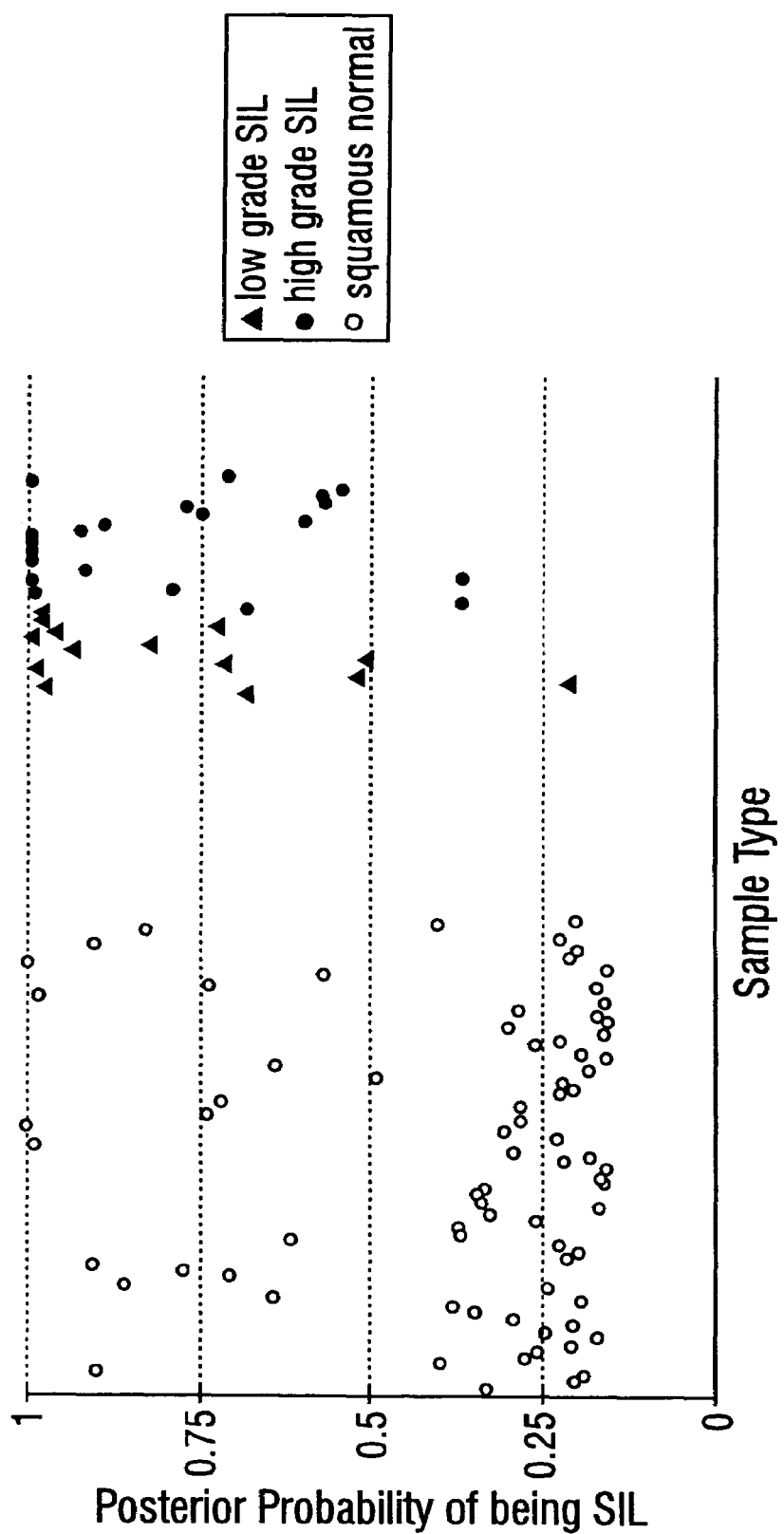

FIGS. 7A and 7B illustrate the measured probability distribution and the best fit of the normal probability density function to PC1 and PC2 of normal squamous tissues and SILs, respectively. There is reasonable agreement between the measured and calculated probability distribution, for each case. The prior probabilities were determined to be: 67% normal squamous tissues and 33% SILs. Next, posterior probabilities of belonging to each tissue type were calculated for all samples in the data set. FIG. 8 illustrates the retrospective performance of the diagnostic method on the same data set used to optimize it. The posterior probability of being classified into the SIL category is plotted for all samples evaluated. The results shown are for a cost of misclassification of SILs equal to 55%. FIG. 8 indicates that 92% of SILs have a posterior probability greater than 0.5, and 76% of normal squamous tissues have a posterior probability less than 0.5.

A prospective estimate of the method's performance was obtained using cross-validation. Table 4A and Table 4B compare (a) the retrospective performance of the method on the data set used to optimize it to (b) the prospective estimate of the method's performance using cross-validation. The method uses mean-scaled normalized spectra at 460 nm excitation to differentiate SILs from normal squamous tissues. Table 4A indicates that for a cost of misclassification of SILs equal to 55%, 92% of high grade SILs, 90% of low grade SILs, and 76% of normal squamous samples are correctly classified. The unbiased estimate of the method's performance in Table 4B indicates that there is no change in the percentage of correctly classified high grade SILs or normal squamous tissue; there is a 5% decrease in the proportion of correctly classified low grade SILs.

TABLE 4A

| Classification | Normal Squamous | Low Grade SIL | High Grade SIL |
| --- | --- | --- | --- |
| Normal Squamous | 76% | 7% | 9% |
| SIL | 24% | 93% | 91% |

TABLE 4B

| Classification | Normal Squamous | Low Grade SIL | High Grade SIL |
| --- | --- | --- | --- |
| Normal Squamous | 75% | 14% | 9% |
| SIL | 25% | 86% | 91% |

4. Low Grade SILs vs. High Grade SILs at 460 n.m Excitation. Principal components obtained from the preprocessed data matrix containing normalized spectra at 460 nm excitation could be used to differentiate high grade SILs from low grade SILs. These principal components are included in Appendix D. Principal component 4 (PC4) and principal component 7 (PC7) demonstrated the statistically most significant differences (p<0.05) between high grade SILs and low grade SILs. The p values of the remaining principal component scores were not statistically significant (p>0.09). Therefore, the rest of the analysis was performed using these two principal components which account collectively for 8% of the variation in the original data set.

Figure 9A:
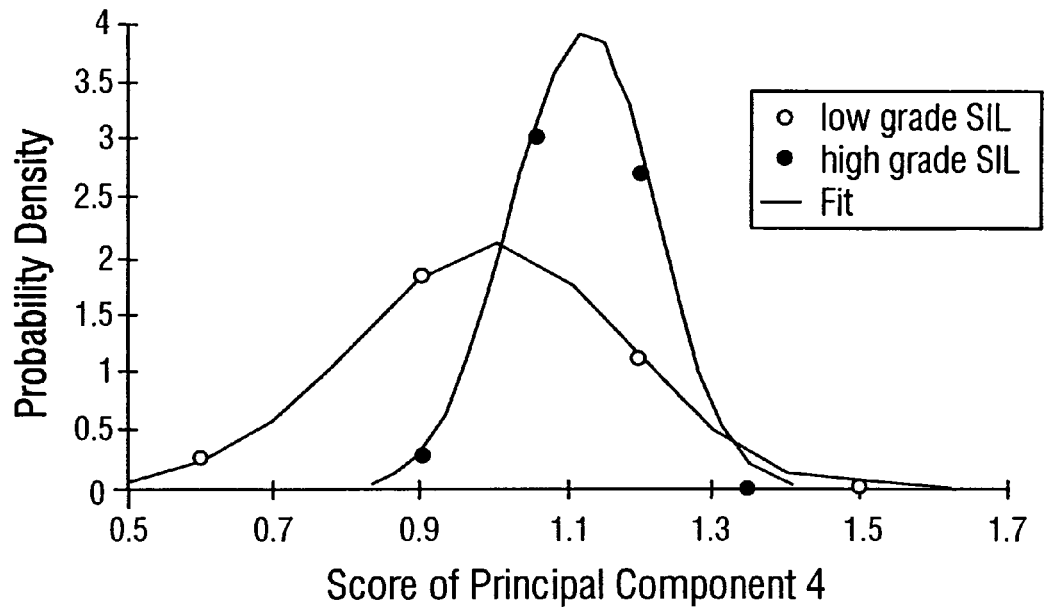
FIGS. 9A, 9B and 10 are graphs illustrating the performance of the first fluorescence spectrum diagnostic method to distinguish low grade SIL from high grade SIL at 460 nm excitation.
Figure 9B:
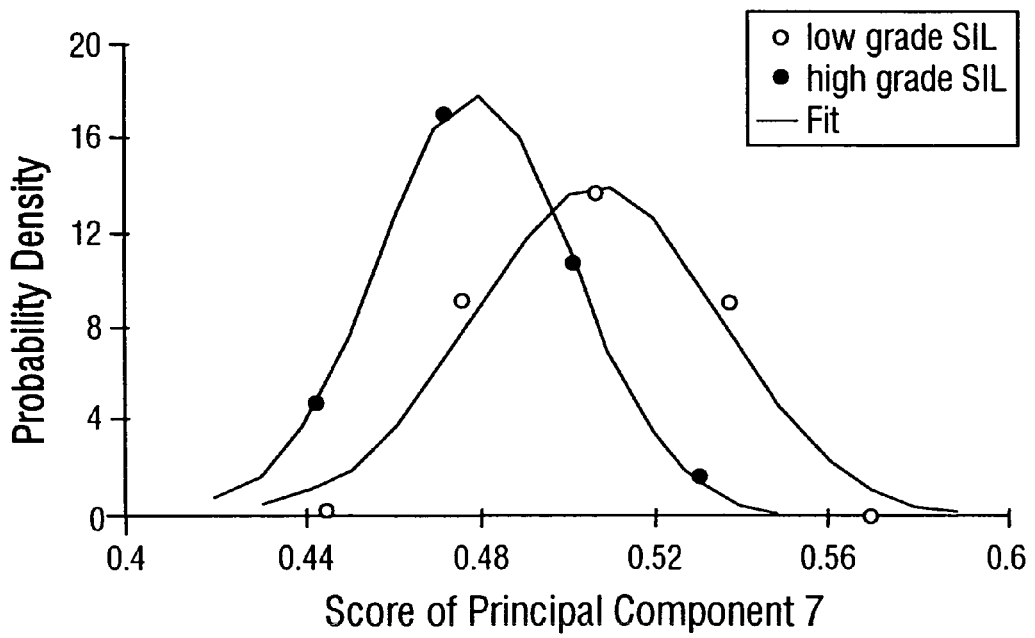

FIGS. 9A and 9B illustrate the measured probability distribution and the best fit of the normal probability density function of PC4 and PC7 for normal squamous tissues and SILs, respectively. There is reasonable agreement between the measured and calculated probability distribution, for each case. The prior probability was determined to be: 39% low grade SILs and 61% high grade SILs. Posterior probabilities of belonging to each tissue type were calculated.

Figure 10:
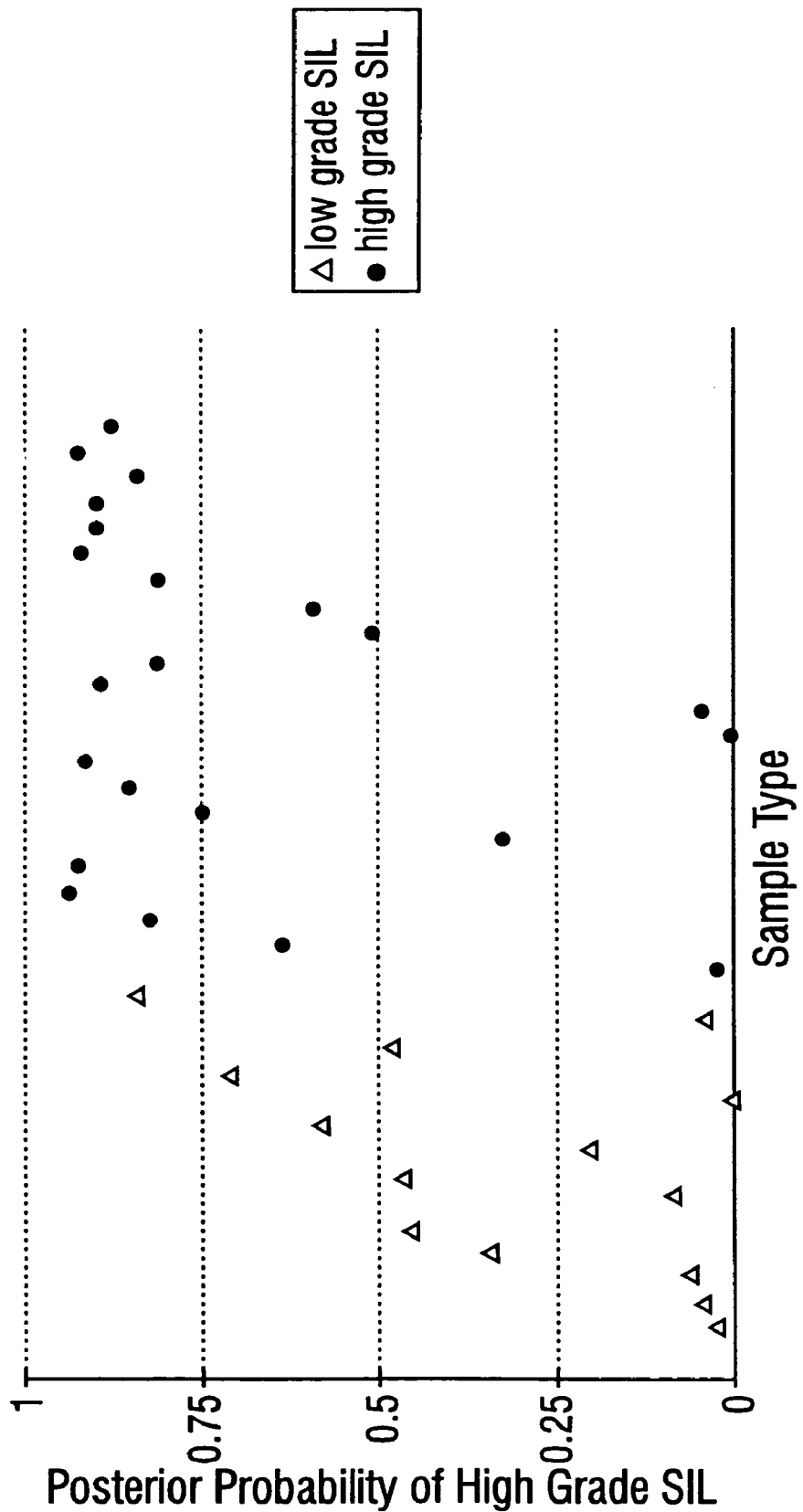

FIG. 10 illustrates the retrospective performance of the diagnostic method on the same data set used to optimize it. The posterior probability of being classified into the SIL category is plotted for all samples evaluated. The results shown are for a cost of misclassification of SILs equal to 65%. FIG. 10 indicates that 82% of high grade SILs have a posterior probability greater than 0.5, and 78% of low grade SILs have a posterior probability less than 0.5.

A prospective estimate of the method's performance was obtained using cross-validation. Table 5A and Table 5B compare (a) the retrospective performance of the method on the data set used to optimize it to (b) the unbiased estimate of the method's performance using cross-validation. The method uses mean-scaled normalized spectra at 460 nm excitation to differentiate high grade from low grade SILs. Table 5A indicates that for a cost of misclassification of 65% 82% of high grade SILs and 78% of low grade SILs are correctly classified. The unbiased estimate of the method's performance in Table 5B indicates that there is a 5% decrease in the percentage of correctly classified high grade SILs and low grade SILs.

TABLE 5A

| Classification | Low Grade SIL | High Grade SIL |
| --- | --- | --- |
| Low Grade SIL | 79% | 18% |
| High Grade SIL | 21% | 82% |

TABLE 5B

| Classification | Low Grade SIL | High Grade SIL |
| --- | --- | --- |
| Low Grade SIL | 72% | 27% |
| High Grade SIL | 21% | 77% |

Figure 2A:
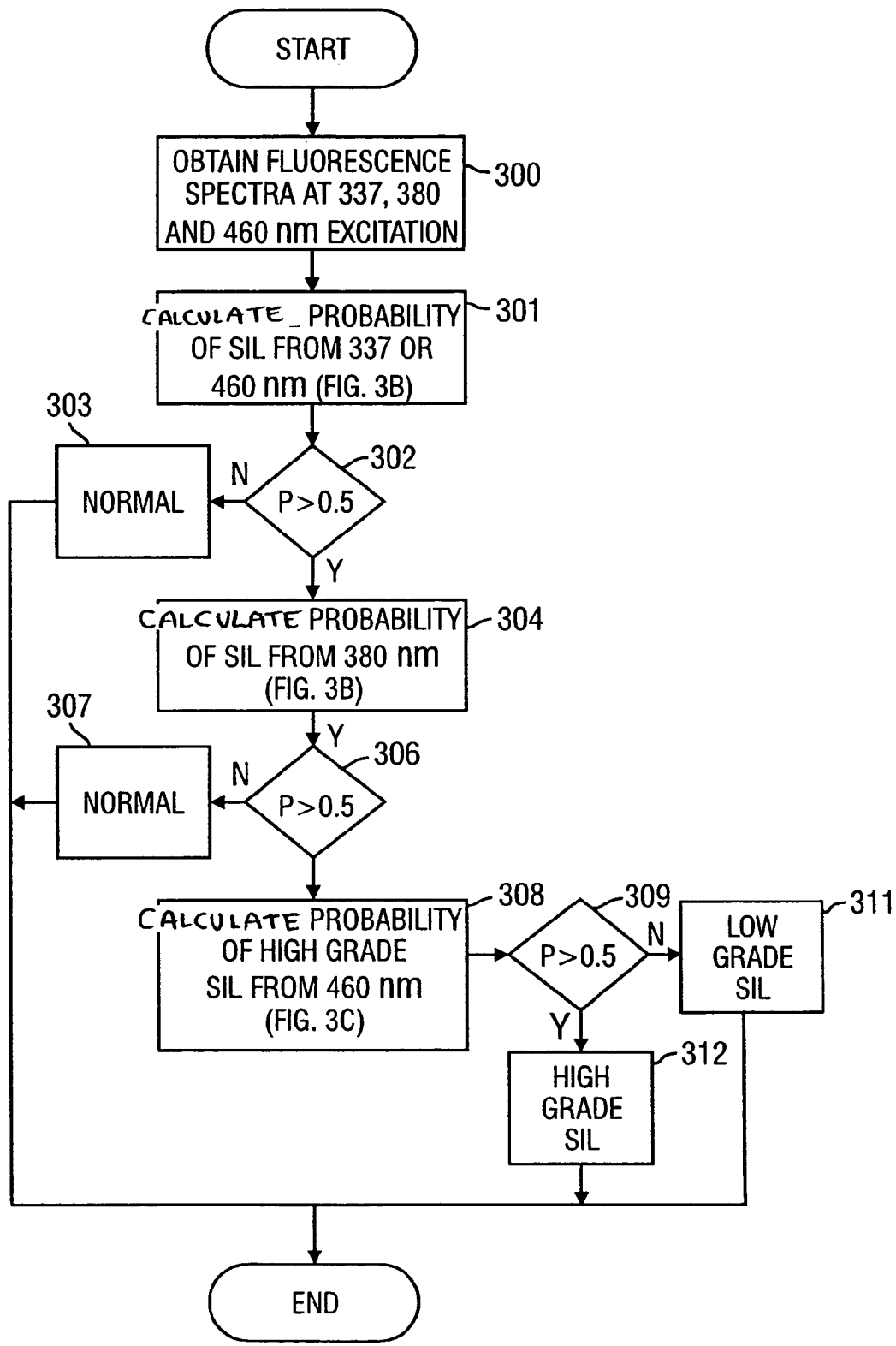
FIGS. 2A, 2B and 2C are flowcharts of a first exemplary fluorescence spectroscopy diagnostic methods.
Figure 2B:
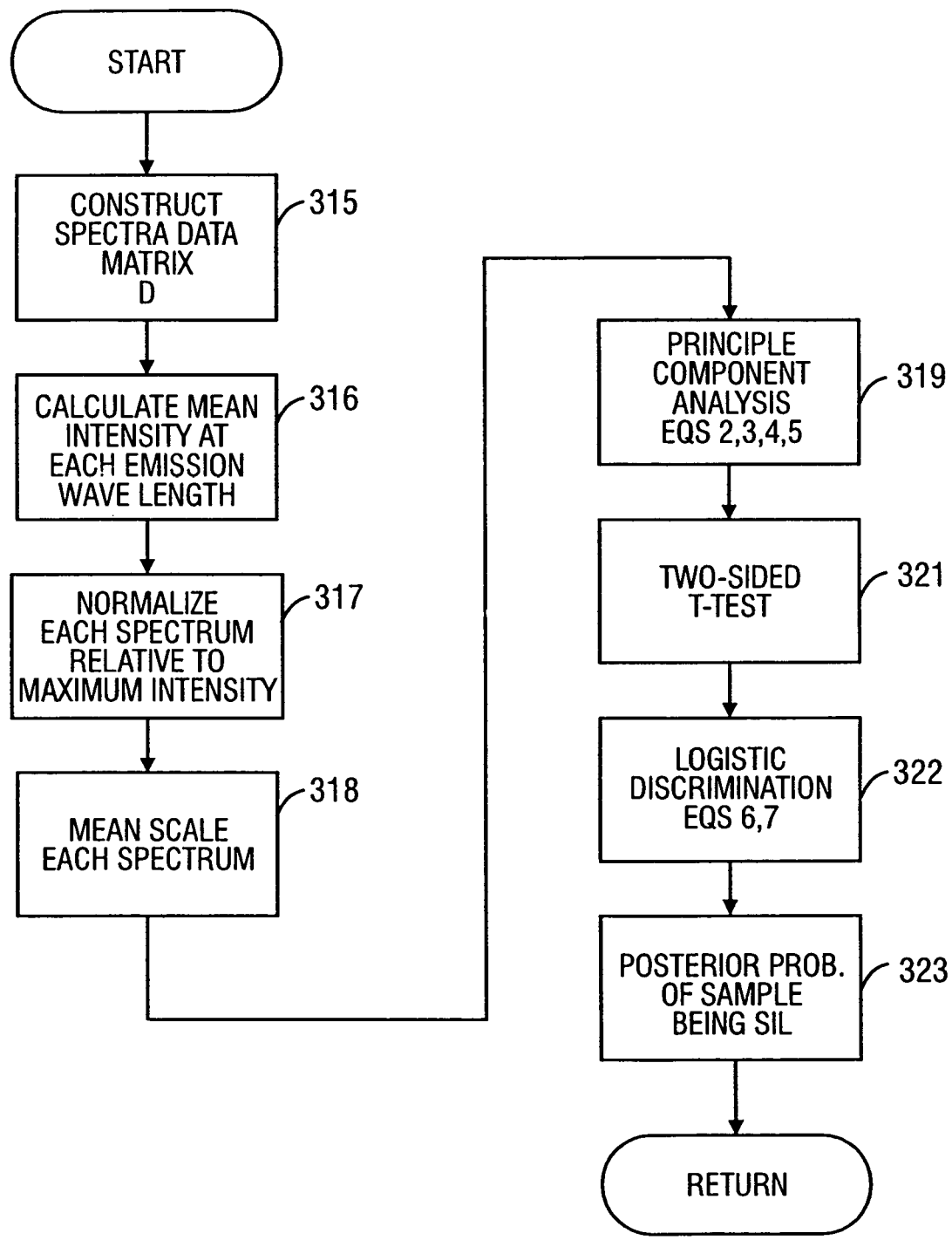
Figure 2C:
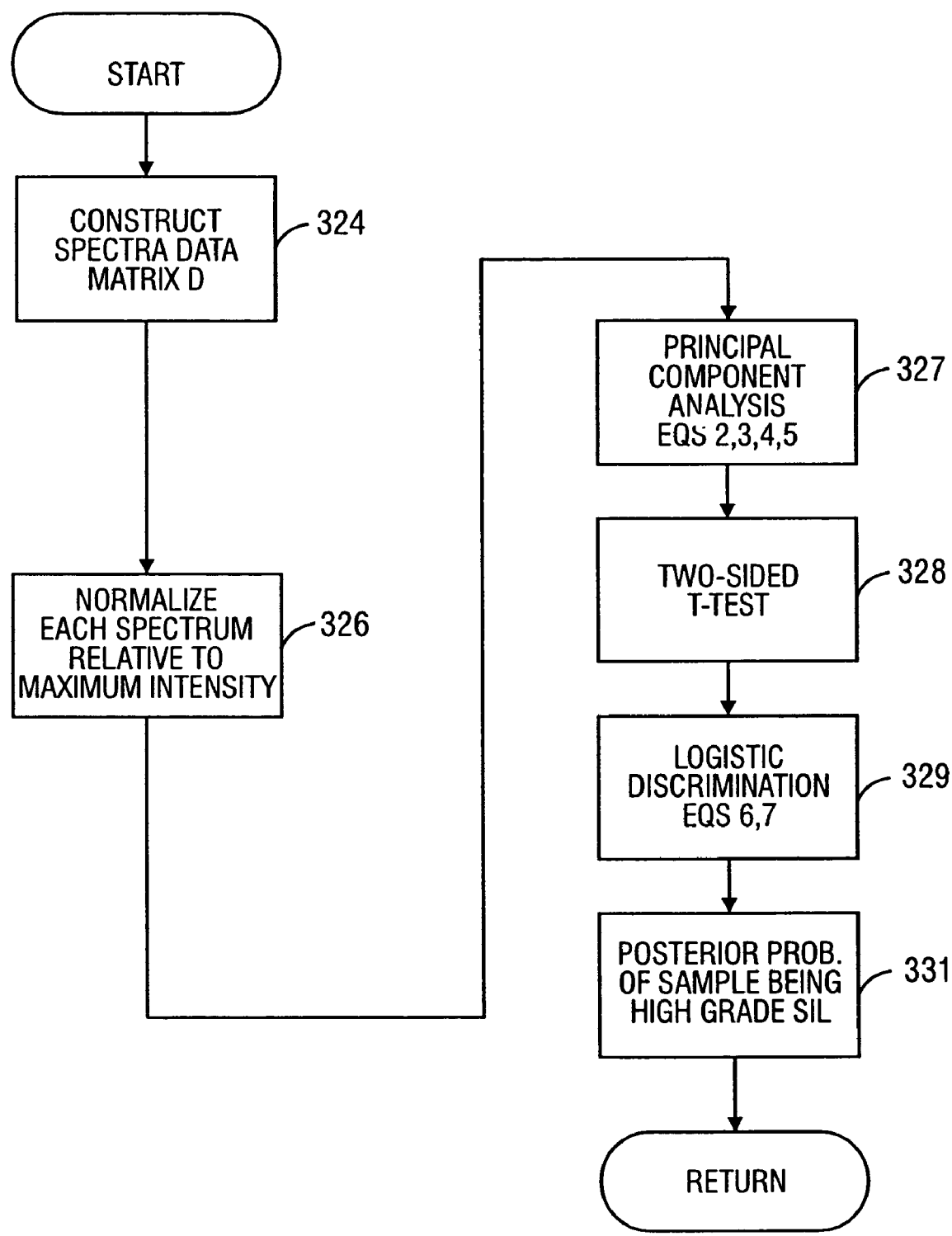

FIGS. 2A, 2B and 2C are flowcharts of the above-described fluorescence spectroscopy diagnostic methods. In practice, the flowcharts of FIGS. 2A, 2B and 2C are coded into appropriate form and are loaded into the program memory of computer 119 (FIG. 1) which then controls the apparatus of FIG. 1 to cause the performance of the diagnostic method.

Referring first to FIG. 2A, control begin in block 300 where fluorescence spectra are obtained from the patient at 337, 380 and 460 nm excitation. Control then passes to block 301 where the probability of the tissue sample under consideration being SIL is calculated from the spectra obtained from the patient at 337 or 460 nm. This method is shown in more detail with reference to FIG. 3B.

Control then passes to decision block 302 where the probability of SIL calculated in block 301 is compared against a threshold of 0.5. If the probability is not greater than 0.5, control passes to block 303 where the tissue sample is diagnosed normal, and the routine is ended. On the other hand, if the probability calculated in block 301 is greater than 0.5, control passes to block 304 where the probability of the tissue containing SIL is calculated based upon the emission spectra obtained from excitation at 380 nm. This method is identical to the method used to calculate probability of SIL from fluorescence spectra due to 337 or 460 nm, and is also presented below in more detail with reference to FIG. 3B.

Control then passes to decision block 306 where the probability of SIL calculated in block 304 is compared against a threshold of 0.5. If the probability calculated in block 304 is not greater than 0.5, control passes to block 307 where normal tissue is diagnosed and the routine is ended. Otherwise, if decision block 306 determines that the probability calculated in block 304 is greater than 0.5, control passes to block 308 where the probability of high grade SIL is calculated from the fluorescence emission spectra obtained from a 460 nm excitation. This method is discussed below in greater detail with reference to FIG. 3C.

Control then passes to decision block 309 where the probability of high grade SIL calculated in block 308 is compared with a threshold of 0.5. If the probability calculated in block 308 is not greater than 0.5, low grade SIL is diagnosed (block 311), otherwise high grade SIL is diagnosed (block 312).

Referring now to FIG. 2B, the conditioning of the fluorescence spectra by blocks 301 and 304 is presented in more detail. It should be noted that while the processing of block 301 and 304 is identical, block 301 operates on spectra obtained from a 337 or 460 nm excitation, whereas block 304 operates on spectra obtain from a 380 nm excitation. In either case, control begins in block 315 where the fluorescence spectra data matrix, D, is constructed, each row of which corresponds to a sample fluorescence spectrum taken from the patient. Control then passes to block 316 where the mean intensity at each emission wavelength of the detected fluorescence spectra is calculated. Then, in block 317, each spectrum of the data matrix is normalized relative to a maximum of each spectrum. Then, in block 318, each spectrum of the data matrix is mean scaled relative the mean calculated in block 316. The output of block 318 is a preprocessed data matrix, comprising preprocessed spectra for the patient under examination.

Control then passes to block 319 where principal component analysis is conducted, as discussed above, with reference to equations 2, 3, 4 and 5. During principal component analysis, the covariance matrix Z (equation (2)), is calculated using a preprocessed data matrix, the rows of which comprise normalized, mean scaled spectra obtained from all patients, including the patient presently under consideration. The result of block 319 is applied to block 321 where a two-sided Student's T-test is conducted, which results in selection of only diagnostic principal components. Control then passes to block 322 where logistic discrimination is conducted, which was discussed above with reference to equations 6 and 7.

The quantity calculated by block 322 is the posterior probability of the sample belonging to the SIL category (block 323)

Referring now to FIG. 2C, presented are the details of the determination of the probability of high grade SIL from excitation at 460 nm (block 308, FIG. 3A). Control begins in block 324 where the fluorescence spectra data matrix, D, is constructed, each row of which corresponds to a sample fluorescence spectrum taken from the patient. Control then passes to block 326 where each spectrum of the data matrix is normalized relative to a maximum of each spectrum. The output of block 326 is a preprocessed data matrix, comprising preprocessed spectra for the patient under examination. It should be noted that, in contrast to the preprocessing performed in the SIL probability calculating routine of FIG. 3B, there is no mean scaling performed when calculating the probability of high grade SIL.

Control then passes to block 327 where principal component analysis is conducted, as discussed above, with reference to equations 2, 3, 4 and 5. During principal component analysis, the covariance matrix Z (equation (2)), is calculated using a preprocessed data matrix, the rows of which comprise normalized, mean scaled spectra obtained from all patients, including the patient presently under consideration. The result of block 327 is applied to block 328 where a two-sided Student's T-test is conducted, which results in selection of only diagnostic principal components. Control then passes to block 329 where logistic discrimination is conducted, which was discussed above with reference to equations 6 and 7.

The quantity calculated by block 329 is the posterior probability of the sample belonging to the high grade SIL category (block 331).

SECOND EXAMPLE

The first example described above is limited in two principal ways. A first limitation is that fluorescence spectra were not acquired at all three excitation wavelengths (337, 380 and 460 nm) from every patient in the study. Therefore, analysis of spectral data from these studies did not indicate if the classification accuracy of each of the three constituent algorithms developed using spectra at a single excitation wavelength could be improved by utilizing tissue spectra at all three excitation wavelengths. A second limitation of these studies is that the accuracy of composite screening and diagnostic algorithms utilizing a combination of the constituent algorithms could not be evaluated since tissue spectra were not available at all three excitation wavelengths from the same group of patients.

Thus, a first goal of the analysis in this second example is to evaluate the accuracy of constitutient and composite algorithms which address these limitations. Fluorescence spectra acquired in vivo at all three excitation wavelengths from 381 cervical sites in 95 patients were analyzed to determine if the accuracy of each of the three constituent algorithms previously developed in the analysis of the first example can be improved using tissue spectra at a combination of two or three excitation wavelengths rather than at a single excitation wavelength.

A second goal of the analysis is to integrate the three independently developed constituent algorithms which discriminate between pairs of tissue types into composite screening and diagnostic algorithms that can achieve discrimination between many of the clinically relevant tissue types. The effective accuracy of a composite screening algorithm for the identification of SILs (normal epithelium and inflammation versus SIL) and a composite diagnostic algorithm for the identification of high grade SILs (non-high grade versus high grade) was evaluated.

Instrumentation

Figure 11:
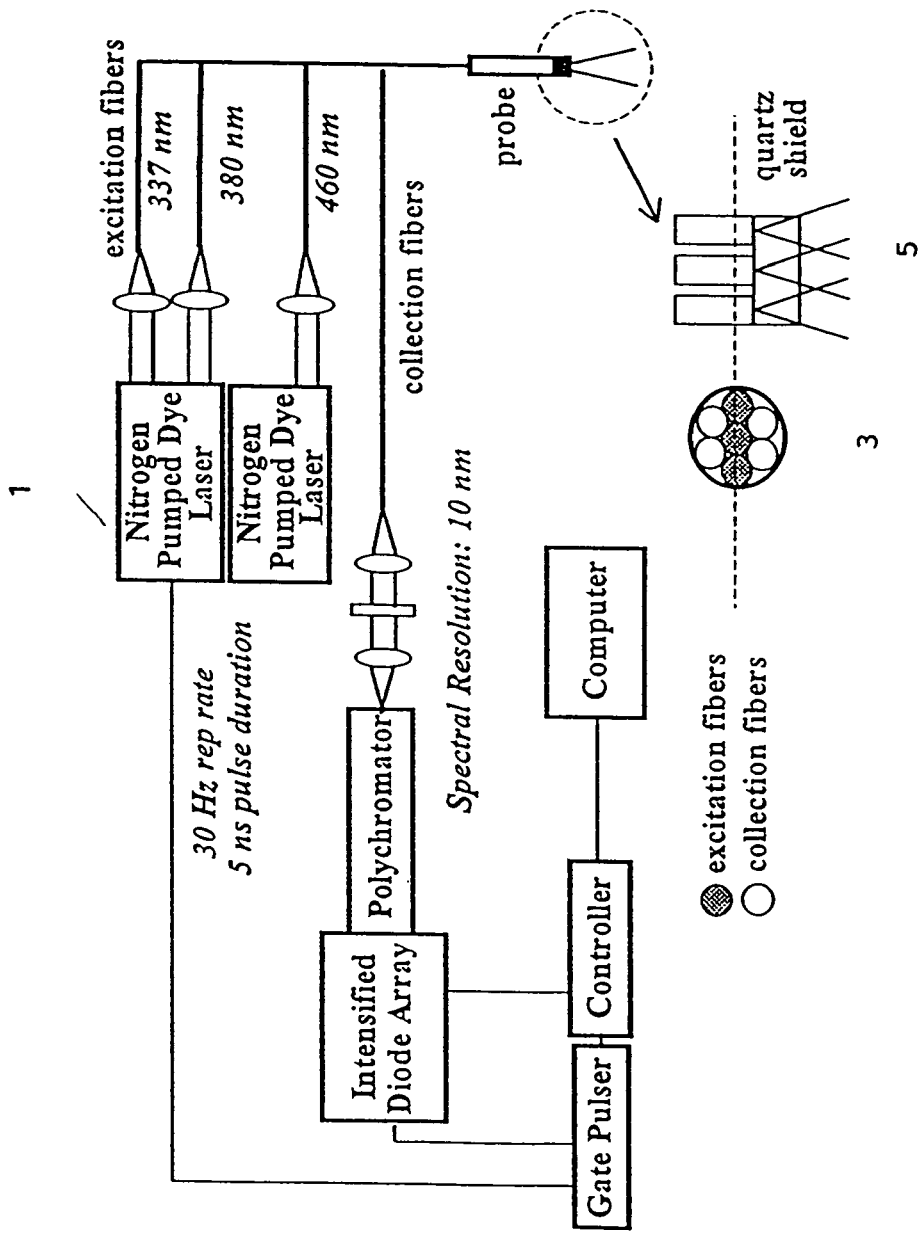
FIG. 11 is a schematic of the portable fluorimeter used to measure cervical tissue fluorescence spectra at three excitation wavelengths.

A schematic of the portable fluorimeter 1 which was used to acquire cervical tissue fluorescence spectra at three excitation wavelengths is shown in FIG. 11. The fiber-optic probe 3 includes a central fiber surrounded by a circular array of six fibers; all seven fibers have the same characteristics (0.22 NA, 200 µm core diameter). Three fibers along the diameter of the distal end of the probe (FIG. 11) are used for excitation light delivery (overlap of the illumination area viewed by the three excitation fibers is greater than 85%). The purpose of the remaining four fibers is to collect the emitted fluorescence from the area (1 mm diameter) directly illuminated by the probe. A quartz shield 5 at the tip of the distal end of the probe which is in direct tissue contact (FIG. 11) provides a fixed distance between the optical fibers and the tissue surface so fluorescence intensity can be measured in calibrated units.

Two nitrogen pumped-dye lasers are used to provide illumination at three different excitation wavelengths: one laser serves to deliver excitation light at 337 nm (fundamental) and has a dye module which is used to generate light at 380 nm using the fluorescent dye, BBQ (1E-03 M in 7 parts toluene and 3 parts ethanol). The dye module of the second laser is used to provide illumination at 460 nm, using the fluorescent dye, Coumarin 460 (1E-02 M in ethanol). Laser illumination at each excitation wavelength, 337, 380 and 460 nm is coupled into each of the excitation fibers. In this study, the average transmitted pulse energies at 337, 380 and 460 nm excitation were 12, 9 and 14 µJ, respectively. The laser characteristics were a 5 ns pulse duration and a repetition rate of 30 Hz.

The proximal ends of the four emission collection fibers are arranged in a circular array and imaged at the entrance slit of a polychromator coupled to a 1,024 intensified diode array controlled by a multi-channel analyzer. 360, 400 and 470 nm long pass filters are used to block scattered excitation light at 337, 380 and 460 nm excitation, respectively from the detector. A 205 ns collection gate, synchronized to the leading edge of the laser pulse using a pulser (Princeton Instruments, PG200), eliminates the effects of the colposcope's white light illumination during fluorescence measurements. Data acquisition is computer controlled.

Method

The method pertains to the development and application of a detection technique for human cervical pre-cancer, both in vitro and in vivo, based on laser induced fluorescence spectroscopy. Fluorescence spectra from 381 cervical samples in 95 patients were acquired at three excitation wavelengths: 337, 380 and 460 nm. A general multivariate statistical algorithm is then used to analyze and extract clinically useful information from tissue spectra acquired in vivo. This experiment includes a screening algorithm to discriminate between SILs and non-SILs (normal squamous and columnar epithelia and inflammation), and a diagnostic algorithm to differentiate high grade SILs from non-high grade SILs (low grade SILs, normal epithelia and inflammation). The retrospective and prospective accuracy of both the screening and diagnostic algorithms is compared to the accuracy of Pap smear screening, see Appendix A, Reference 5, and to colposcopy in expert hands, see Appendix A, Reference 9.

Clinical measurements. A randomly selected group of non-pregnant patients referred to the colposcopy clinic of the University of Texas MD Anderson Cancer Center on the basis of abnormal cervical cytology was asked to participate in the in vivo fluorescence spectroscopy study. Informed consent was obtained from each patient who participated and the study was reviewed and approved by the Institutional Review Boards of the University of Texas, Austin and the University of Texas, MD Anderson Cancer Center. Each patient underwent a complete history and a physical examination including a pelvic exam, a Pap smear and colposcopy of the cervix, vagina and vulva.

After colposcopic examination of the cervix, but before tissue biopsy, fluorescence spectra were acquired on average from two colposcopically abnormal sites, two colposcopically normal squamous sites and 1 normal columnar site (if colposcopically visible) from each patient. Tissue biopsies were obtained only from abnormal sites identified by colposcopy and subsequently analyzed by the probe to comply with routine patient care procedure. All tissue biopsies were fixed in formalin and submitted for histologic examination. Hemotoxylin and eosin stained sections of each biopsy specimen were evaluated by a panel of four board certified pathologists and a consensus diagnosis was established using the Bethesda classification system; see Appendix A, Reference 1. This classification system which has previously been used to grade cytologic specimens has now been extended to classification of histology samples. Samples were classified as normal squamous, normal columnar, inflammation, low grade SIL or high grade SIL. Samples with multiple diagnoses were classified into the most severe histo-pathologic category.

Prior to each patient study, the probe was disinfected and a background spectrum was acquired at all three excitation wavelengths consecutively with the probe dipped in a non-fluorescent bottle containing distilled water. The background spectrum was subtracted from all subsequently acquired spectra at corresponding excitation wavelengths for that patient. Next, with the probe placed on the face of a quartz cuvette containing a solution of Rhodamine 610 dissolved in ethylene glycol (2 mg/L), 50 fluorescence spectra were measured at each excitation wavelength. After calibration, fluorescence spectra were acquired from the cervix: 10 spectra for 10 consecutive pulses were acquired at 337 nm excitation; next, 50 spectra for 50 consecutive laser pulses were measured at 380 nm excitation and then at 460 nm excitation. The data acquisition time was 0.33 s at 337 nm excitation and 1.67 s at each 380 and 460 nm excitation per cervical site. Spectra were collected in the visible region of the electromagnetic spectrum with a resolution of 10 nm (full width at half maximum) and a signal to noise ratio of 30:1 at the fluorescence maximum at each excitation wavelength.

All spectra were corrected for the non-uniform spectral response of the detection system using correction factors obtained by recording the spectrum of an N.I.S.T traceable calibrated tungsten ribbon filament lamp. Spectra from each cervical site at each excitation wavelength were averaged and normalized to the peak fluorescence intensity of the Rhodamine 610 calibration standard at the corresponding excitation wavelength for that patient; absolute fluorescence intensities are reported in these calibrated units. In this clinical study, fluorescence spectra were acquired at all three excitation wavelengths from each cervical site from a total of 381 sites in 95 patients during colposcopy.

Figure 12:
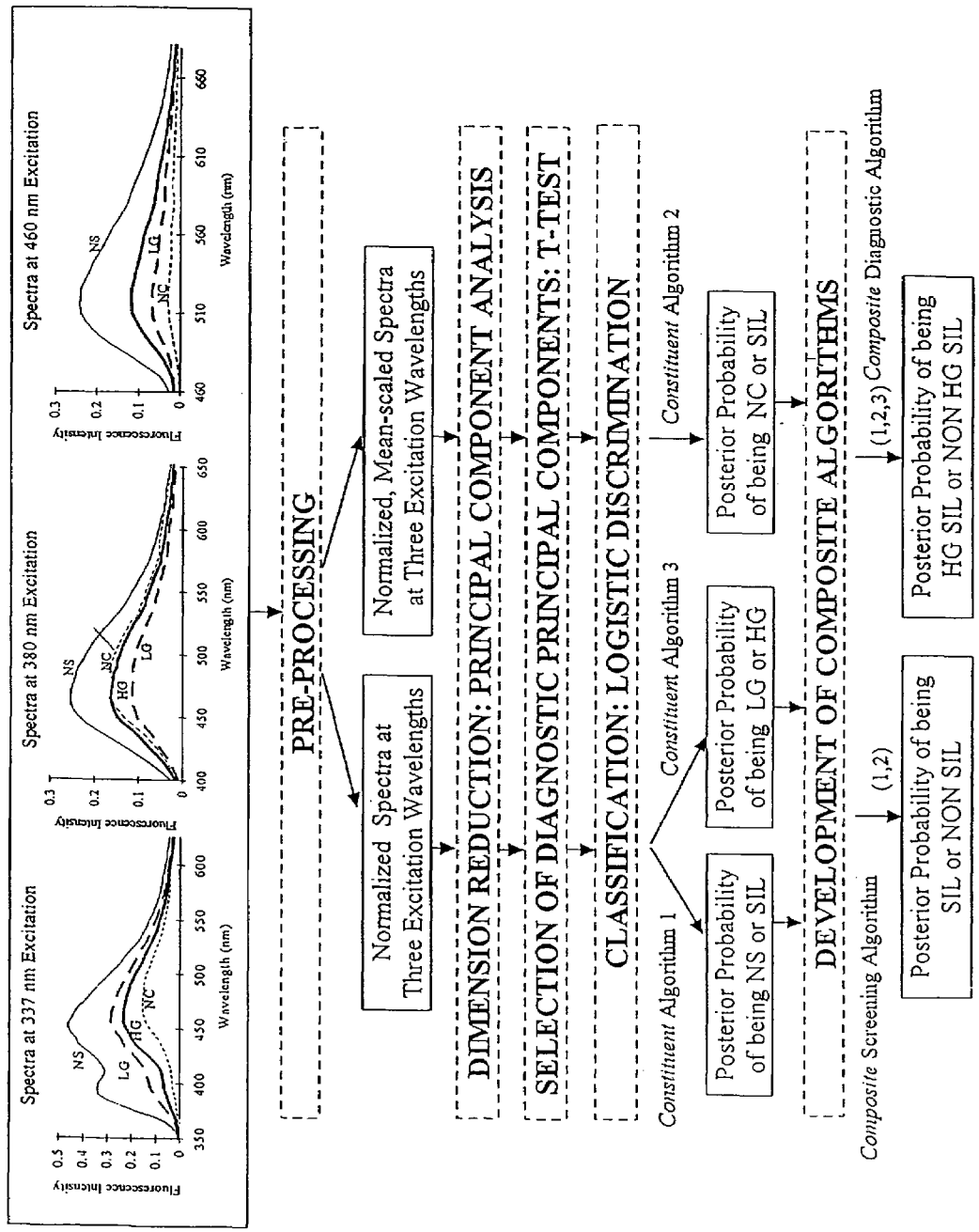
FIG. 12 is a flow chart of a formal analytical process used to develop the screening and diagnostic algorithms. The text in the dashed-line boxes represent mathematical steps implemented on the spectral data and the text in the solid line boxes represent outputs after each mathematical step (NS—normal squamous, NC—normal columnar, LG—LG SIL and HG—HG SIL).

Development of screening and diagnostic algorithms. FIG. 12 illustrates a schematic of the formal analytical process used to develop screening and diagnostic algorithms for the differential detection of SILs, in vivo. In FIG. 12, the text in the dashed-line boxes represents the mathematical steps implemented on the spectral data, and the text in the solid-line boxes represent the output after each mathematical process. There are four primary steps involved in the multivariate statistical analysis of tissue spectral data. The first step is to pre-process spectral data to reduce inter-patient and intra-patient variation within a tissue type; the pre-processed spectra are then dimensionally reduced into an informative set of principal components which describe most of the variance of the original spectral data set using Principal Component Analysis (PCA). Next, the principal components which contain diagnostically relevant information are selected using an unpaired, one-sided student's t-test, and finally a classification algorithm based on logistic discrimination is developed using these diagnostically relevant principal components.

In summary, three constituent algorithms were developed using multivariate statistical analysis: a constituent algorithm (1) that discriminates between SILs and normal squamous tissues, a constituent algorithm (2) that discriminates between SILs and normal columnar tissues, and a constituent algorithm (3) that differentiates high grade SILs from low grade SILs. The three constituent algorithms were then combined to develop two composite algorithms: constituent algorithms (1) and (2) were combined to develop a composite screening algorithm which discriminates between SILs and non SILs; and all three constituent algorithms were combined to develop a composite diagnostic algorithm which differentiates high grade SILs from non-high grade SILs.

Multivariate statistical analysis of cervical tissue spectra. As a first step, three methods of pre-processing were applied to the spectral data at each excitation wavelength: 1) normalization 2) mean-scaling and 3) a combination of normalization and mean-scaling. Similarly pre-processed spectra at each excitation wavelength were combined to create spectral inputs at the following combinations of excitation wavelengths: (337, 460) nm, (337, 380) nm, (380, 460) nm and (337, 380, 460) nm. Pre-processing of spectral data resulted in four types of spectral inputs (original and three types of pre-processed spectral inputs) at three single excitation wavelengths and at four possible combinations of multiple excitation wavelengths. Hence, there were a total of 12 spectral inputs at single excitation wavelengths and 16 spectral inputs at multiple excitation wavelengths which were evaluated using the multivariate statistical algorithm.

Prior to PCA, the input data matrix, D(r×c) was created so each row of the matrix corresponded to the pre-processed fluorescence spectrum of a sample and each column corresponded to the pre-processed fluorescence intensity at each emission wavelength. Spectral inputs at multiple excitation wavelengths were created by arranging spectra at each excitation wavelength in series in the original spectral data matrix. PCA (see Appendix A, Reference 28) was used to dimensionally reduce the pre-processed spectral data matrix into a smaller orthogonal set of linear combinations of the emission variables that account for most of the variance of the spectral data set.

Average values of principal component scores were calculated for each principal component of each tissue type. An unpaired, one-sided student's t-test (see Appendix A, Reference 29) was employed to determine the diagnostic content of each principal component. The hypothesis that the means of the principal component scores of two tissue types are different was tested for (1) normal squamous epithelia and SILs, (2) normal columnar epithelia and SILs and (3) inflammation and SILs. The t-test was extended a step further to determine if there were any statistically significant differences between the means of the principal component scores of high grade SILs and low grade SILs. Principal components for which the hypothesis stated above was statistically significant ($P<0.05$) were retained for further analysis.

Next, a statistical classification algorithm was developed using the diagnostically useful principal components to calculate the posterior probability that an unknown sample belongs to each tissue type under consideration. The posterior probability of an unknown sample belonging to each tissue type was calculated using logistic discrimination; see Reference 30. The posterior probability is related to the prior and conditional joint probabilities and to the costs of misclassification of the tissue types under consideration. The prior probability of each tissue type was determined by calculating the observed proportion of cases in each group. The cost of misclassification of a particular tissue type was varied from 0 to 1 in 0.1 increments, and the optimal cost was identified when the total number of misclassified samples based on the classification algorithm was a minimum. If there was more than one cost at which the total number of misclassified samples was a minimum, the cost that maximized sensitivity was selected. The conditional joint probabilities were developed by modeling the probability distribution of each principal component of each tissue type using the normal probability density function, see Appendix A, Reference 31, which is characterized by $\mu$ (mean) and $\sigma$ (standard deviation). The best fit of the normal probability density function to the probability distribution of each principal component (score) of each tissue type was obtained in the least squares sense, using $\mu$ and $\sigma$ as free parameters of the fit. The normal probability density function was then used to calculate the conditional joint probability that an unknown sample, given that it is from tissue type i, will exhibit a set of principal component scores, x.

The multivariate statistical algorithm was developed and optimized using a calibration set and then tested in an unbiased manner on a prediction set of approximately equal prior probability (Table 6). Data in the prediction set is pre-processed and organized into two prediction datasets in the following way. Spectra obtained from each patient at each excitation wavelength are separately (1) normalized and (2) normalized, followed by mean-scaling. Spectra at each excitation wavelength, processed in a similar manner are concatenated into a vector. Two prediction data matrices are developed. In each matrix, each row is a vector containing similarly pre-processed fluorescence emission spectra at 337, 380 and 460 nm excitation concatenated and each column corresponds to pre-processed fluorescence intensity at a particular excitation emission wavelength pair.

These processed data matrices are then used to test the composite screening algorithm performance. The steps of this test are:

The normalized prediction data matrix (Dn') is multiplied by the reduced eigenvector matrix from normalized spectral data of the calibration set (Cn'). Cn' contains only those eigenvectors which displayed statistically significant differences for samples to be classified by constituent algorithm 1.

The posterior probabilities that a sample is SIL or normal squamous epithelium are calculated using Bayes theorem. In this calculation, the mean values and standard deviations of the PC scores for normal squamous epithelium and SILs and prior probabilities and optimal costs of misclassification of the calibration set are used.

The normalized, mean-scaled prediction data matrix (Dnm') is multiplied by the reduced eigenvector matrix from normalized, mean-scaled spectral data of the calibration set (Cnm'). Cnm' contains only those eigenvectors which displayed statistically significant differences for samples to be classified by constituent algorithm 2.

The posterior probabilities that a sample is SIL or normal columnar epithelium are calculated using Bayes theorem. In this calculation, the mean values and standard deviations of the PC scores for normal columnar epithelium and SILs and prior probabilities and optimal costs of misclassification of the calibration set are used.

Using constituent algorithm 1, samples with a posterior probability of being normal squamous epithelium greater than a threshold value are classified as non-SIL. Remaining samples are classified based on the output of constituent algorithm 2. Using constituent algorithm 2, sample with a posterior probability of being normal columnar epithelium greater than a threshold are classified as non-SIL. The remaining samples are classified as SIL.

The processed data matrices are then used to test the composite diagnostic algorithm performance. The steps of this test are:

- The normalized prediction data matrix (Dn') is multiplied by the reduced eigenvector matrix from normalized spectral data of the calibration set (Cn'). Cn' contains only those eigenvectors which displayed statistically significant differences for samples to be classified by constituent algorithm 1.
- The posterior probabilities that a sample is SIL or normal squamous epithelium are calculated using Bayes theorem. In this calculation, the mean values and standard deviations of the PC scores for normal squamous epithelium and SILs and prior probabilities and optimal costs of misclassification of the calibration set are used.
- The normalized, mean-scaled prediction data matrix (Dnm') is multiplied by the reduced eigenvector matrix from normalized, mean-scaled spectral data of the calibration set (Cnm'). Cnm' contains only those eigenvectors which displayed statistically significant differences for samples to be classified by constituent algorithm 2.
- The posterior probabilities that a sample is SIL or normal columnar epithelium are calculated using Bayes theorem. In this calculation, the mean values and standard deviations of the PC scores for normal columnar epithelium and SILs and prior probabilities and optimal costs of misclassification of the calibration set are used.
- The normalized prediction data matrix (Dn') is multiplied by the reduced eigenvector matrix from normalized spectral data of the calibration set (Cn'). Cn' contains only those eigenvectors which displayed statistically significant differences for samples to be classified by constituent algorithm 3.
- The posterior probabilities that a sample is HGSIL or LGSIL are calculated using Bayes theorem. In this calculation, the mean values and standard deviations of the PC scores for HGSILs and LGSILs and prior probabilities and optimal costs of misclassification of the calibration set are used.
- Using constituent algorithm 1, samples with a posterior probability of being normal squamous epithelium greater than a threshold are classified as non-SIL. Remaining samples are classified based on the output of constituent algorithm 2. Using constituent algorithm 2, sample with a posterior probability of being normal columnar epithelium greater than a threshold are classified as non-SIL. Remaining samples are classified based on the output of constituent algorithm 3. Using constituent algorithm 3, samples with a posterior probability of being LGSIL greater than a threshold are classified as LGSIL. The remaining samples are classified as HGSIL.

The calibration and prediction sets were developed by randomly assigning the spectral data into the two sets with the condition that both contain roughly equal number of samples from each histo-pathologic category. The random assignment ensured that not all spectra from a single patient were contained in the same data set. Table 6 shows the histo-pathologic classification of samples from the calibration and prediction sets. Note that biopsies for histological evaluation were not obtained from colposcopically normal squamous and columnar tissue sites to comply with routine patient care procedure.

TABLE 6

| Histo-pathology | Calibration Set | Prediction Set |
| --- | --- | --- |
| Normal Squamous | 94 | 94 |
| Normal Columnar | 13 | 14 |
| Inflammation | 15 | 14 |
| Low Grade SIL | 23 | 24 |
| High Grade SIL | 35 | 35 |

Development of constituent algorithms. The multivariate statistical algorithm was developed and optimized using all 28 types of pre-processed spectral inputs from the calibration set. The algorithm was used to identify spectral inputs which provide the greatest discrimination between the following pairs of tissue types: (1) SILs and normal squamous epithelia, (2) SILs and normal columnar epithelia, (3) SILs and inflammation, and (4) high grade SILs and low grade SILs. The optimal spectral input for differentiating between two particular tissue types was identified when the total number of samples misclassified from the calibration set using the multivariate statistical algorithm was a minimum. The algorithm based on the spectral input that minimized misclassification between the two tissue types under consideration was implemented on the prediction data set.

Three multivariate statistical constituent algorithms were developed using tissue spectra at three excitation wavelengths. Constituent algorithm (1) was developed to differentiate between SILs and normal squamous epithelia; constituent algorithm (2) was developed to differentiate between SILs and normal columnar epithelia; and constituent algorithm (3) could be used to discriminate between low grade SILs and high grade SILs.

Development of composite algorithms. Each of the independently developed constituent algorithms was intended to discriminate only between pairs of tissue types. A combination of these constituent algorithms was required to provide discrimination between several of the clinically relevant tissue types. Therefore, two composite algorithms were developed: a composite screening algorithm was developed to differentiate between SILs and non SILs (normal squamous and columnar epithelia and inflammation) using constituent algorithms (1) and (2) and a composite diagnostic algorithm was developed to differentiate high grade SILs from non-high grade SILs (low grade SILs, normal epithelia and inflammation) using all three constituent algorithms.

The composite screening algorithm was developed in the following manner. First, constituent algorithms (1) and (2) were developed independently using the calibration data set. The classification outputs from both constituent algorithms were used to determine if a sample being evaluated is SIL or non-SIL: first, using constituent algorithm (1), samples were classified as non SIL if they had a probability that is less than 0.5; otherwise, they were classified as SIL. Next, only samples that were classified as SIL based on the algorithm (1) were tested using algorithm (2). Again, samples were classified as non SIL if their posterior probability was less than 0.5; otherwise they were classified as SIL. The spectral data from the prediction set was evaluated using the composite screening algorithm in an identical manner.

The composite diagnostic algorithm was implemented in the following manner. The three constituent algorithms were developed independently using the calibration set. Algorithms (1) and (2) were implemented on each sample from the calibration data set, as described previously. Only samples that were classified as SIL based on algorithms (1)

and (2) were tested using algorithm (3). If samples evaluated using algorithm (3) had a posterior probability greater than 0.5, they were classified as high grade SIL; otherwise they were classified as non-high grade SIL. The spectral data from the prediction set was evaluated using the composite diagnostic algorithm in an identical manner.

Results: constituent algorithms (1), (2) and (3). Table 7 summarizes the components of the optimal set of three constituent algorithms. Algorithm (1) discriminates between SILs and normal squamous tissues, algorithm (2) discriminates between SILs and normal columnar tissues, and algorithm (3) differentiates high grade (HG) SILs from low grade (LG) SILs. Superscripts in the table refer to the following notes: for the principal component analysis, note 1—Principal Component, and note 2—Variance accounted for by principal component; and for logistic discrimination, note 3—$\mu$ (mean) and $\sigma$ (standard deviation) of principal component scores of tissue types under consideration, and note 4—prior probabilities of tissue types under consideration.

wavelength range 360 to 450 nm; however, between 460 and 600 nm, the fluorescence intensity of the normal columnar tissue is greater than that of the SILs. This spectral difference reflects the longer peak emission wavelength of the normal columnar tissue relative to that of SILs. Further evaluation of Jo normalized spectra in FIG. 13B indicates that there are spectral line shape differences between low grade SILs and high grade SILs over the wavelength range 360 to 420 nm.

Figure 13A:
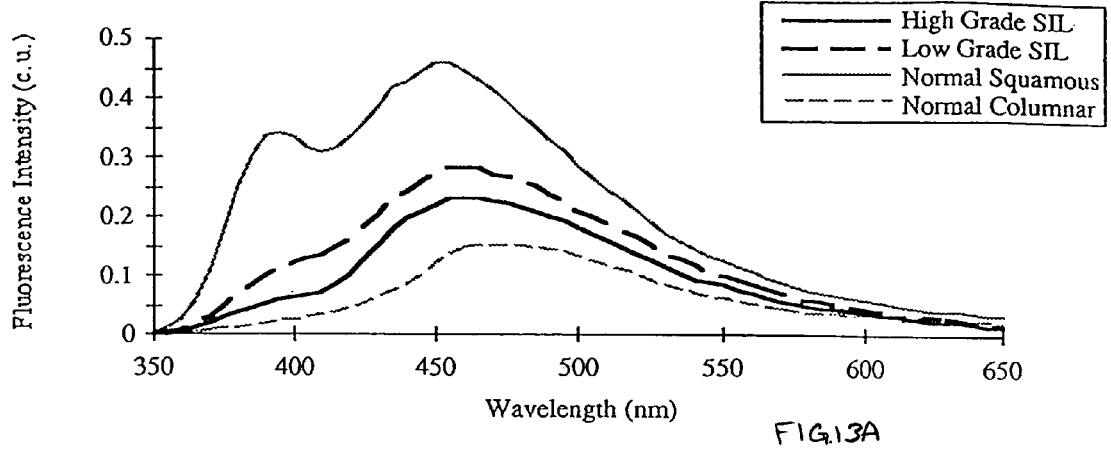
FIG. 13A shows the original spectra.
Figure 13B:
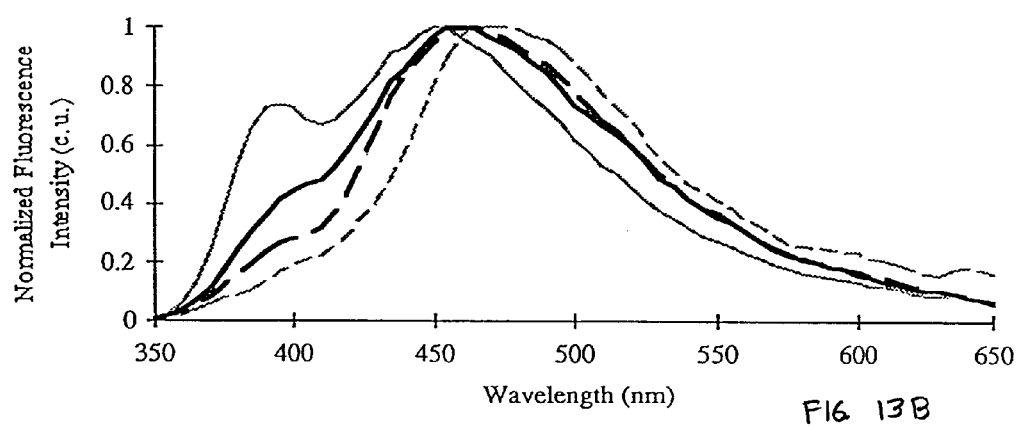
FIG. 13B shows the corresponding normalized spectra.
Figure 13C:
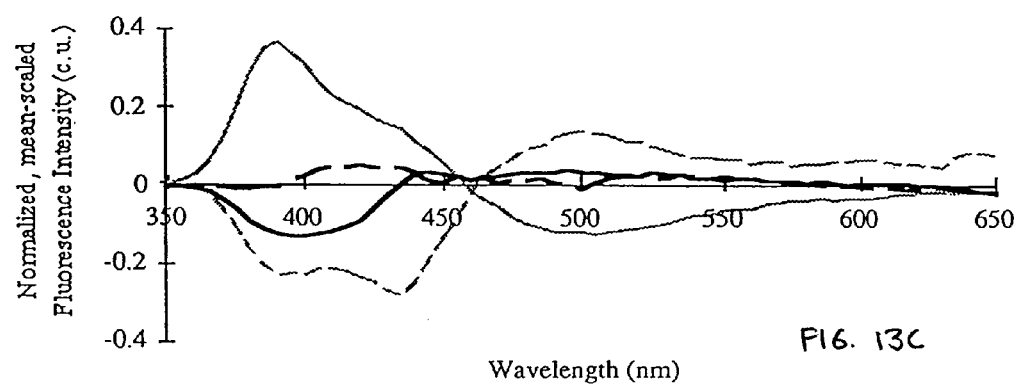
FIG. 13C shows the corresponding normalized, mean-scaled spectra at 337 nm excitation from a typical patient.

The corresponding normalized, mean-scaled spectra of this patient, shown in FIG. 13C displays differences in the normalized fluorescence spectrum (FIG. 13B) from a particular site with respect to the average normalized spectrum from this patient. Evaluation of FIG. 13C indicates that between 360 and 450 nm, the normalized, mean-scaled fluorescence intensity of the normal squamous tissue is greater than the mean (Y=0), and that of the normal columnar tissue is less than the mean. Above 460 nm, the opposite phenomenon is observed; the fluorescence intensity of the normal squamous tissue is less than the mean, while that of

TABLE 7

| Constituent Algorithms | Excitation Wavelengths | Preprocessing Method | $PC^1$ | $V(\%)^2$ | $(\mu, \sigma)^3$ | $PP^4$ |
|---|---|---|---|---|---|---|
| (1) SIL vs. Normal Squamous (NS) | 337, 380, 460 | normalization | PC1 | 51 | NS: (2.993, 1.589) SIL: (2.514, 0.671) | NS: 62% SIL: 38% |
| | | | PC3 | 11 | NS: (2.631, 0.292) SIL: (2.535, 0.427) | |
| | | | PC7 | 3 | NS: (2.850, 0.145) SIL: (2.775, 0.209) | |
| (2) SIL vs. Normal Columnar (NC) | 337, 380, 460 | normalization mean-scaling | PC1 | 59 | NC: (2.479, 0.444) SIL: (2.737, 0.482) | NC: 28% SIL: 72% |
| | | | PC2 | 12 | NC: (2.894, 0.330) SIL: (2.990, 0.367) | |
| | | | PC4 | 6 | NC: (3.006, 0.186) SIL: (3.051, 0.167) | |
| | | | PC5 | 3 | NC: (3.004, 0.101) SIL: (2.994, 0.199) | |
| (3) HG SIL (HG) vs. LG SIL (LG) | 337, 380, 460 | normalization | PC1 | 51 | LG: (2.755, 0.663) HG (2.353, 0.759) | LG: 40% HG: 60% |
| | | | PC3 | 11 | LG: (2.549, 0.394) HG: (2.453, 0.497) | |
| | | | PC6 | 3 | LG: (2.042, 0.180) HG (2.100, 0.180) | |
| | | | PC8 | 2 | LG: (2.486, 0.223) HG: (2.550, 0.130) | |

Pre-processing. FIG. 13A illustrates average fluorescence spectra per site acquired from cervical sites at 337 nm excitation from a typical patient. All fluorescence intensities are reported in the same set of calibrated units. Corresponding normalized and normalized, mean-scaled spectra are illustrated in FIGS. 13B and 13C, respectively. Evaluation of the original spectra at 337 nm excitation (FIG. 13A) indicates that the fluorescence intensity of SILs is less than that of the corresponding normal squamous tissue and greater than that of the corresponding normal columnar tissue over the entire emission spectrum. Examination of normalized spectra from this patient (FIG. 13B) indicates that following normalization, the fluorescence intensity of the normal squamous tissue is greater than that of corresponding SILs over the wavelength range 360 to 450 nm only; between 460 and 600 nm, the fluorescence intensity of SILs is greater than that of the corresponding normal squamous tissue which in part reflects the longer peak emission wavelength of SILs. A comparison of the spectral line shape of SILs to that of the normal columnar tissue illustrates the opposite phenomenon. The normalized fluorescence intensity of SILs is greater than that of the corresponding normal columnar tissue over the the normal columnar tissue is greater than the mean. The fluorescence intensity of SILs lies close to the mean and is bounded by the intensities of the two normal tissue types. In addition, between 360 and 420 nm, the normalized, mean-scaled fluorescence intensity of the low grade SIL is slightly greater than the mean, while that of the high grade SIL is less than the mean.

Figure 14A:
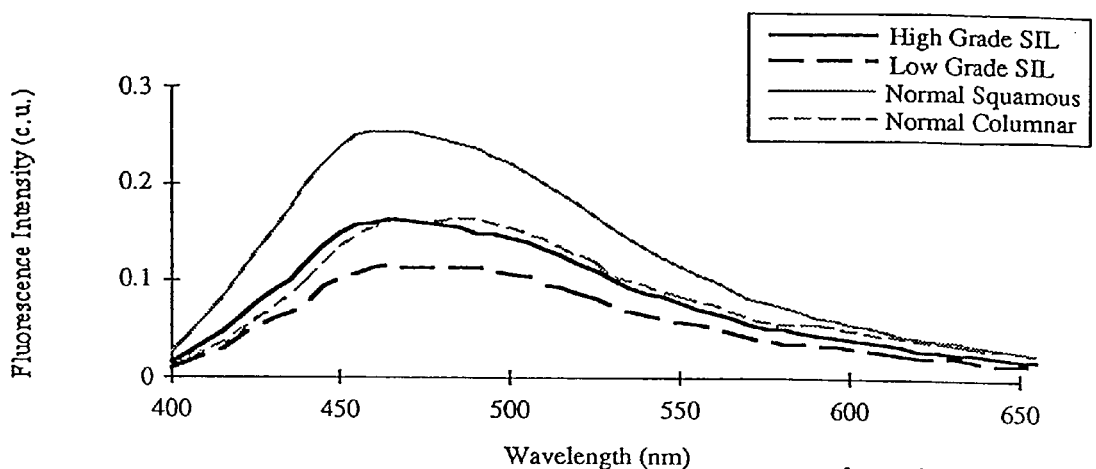
FIG. 14A shows the original spectra.
Figure 14B:
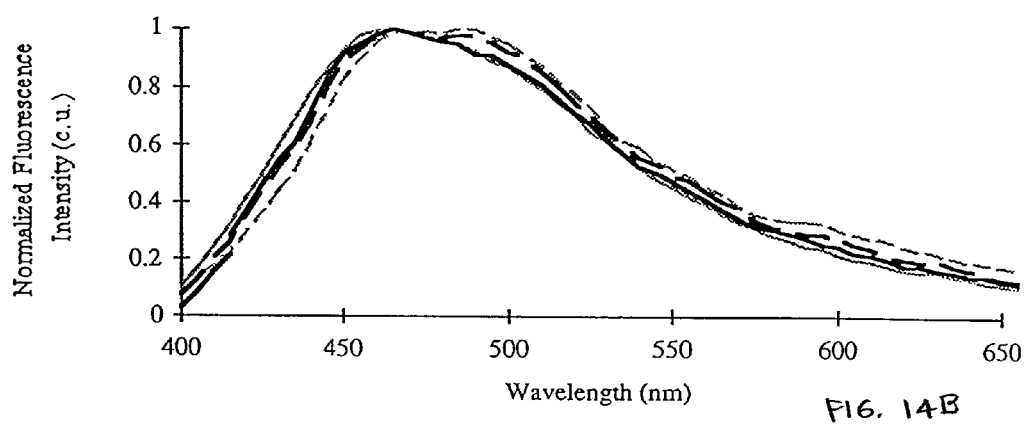
FIG. 14B shows the corresponding normalized spectra.
Figure 14C:
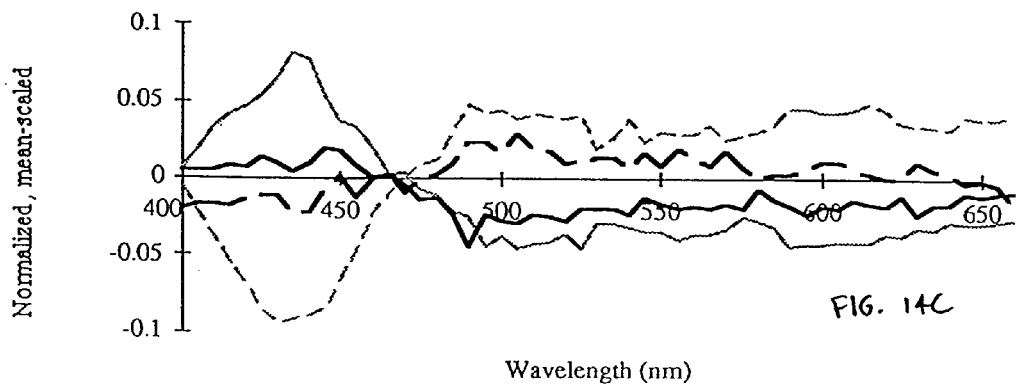
FIG. 14C shows the normalized, mean-scaled spectra at 380 nm excitation from the same patient.

FIG. 14A illustrates average fluorescence spectra per site acquired from cervical sites at 380 nm excitation, from the same patient. FIGS. 14B and 14C show the corresponding normalized, and normalized, mean-scaled spectra, respectively. In FIG. 14A, the fluorescence intensity of SILs is less than that of the corresponding normal squamous tissue, with the low grade SIL exhibiting the weakest fluorescence intensity over the entire emission spectrum. Note that the fluorescence intensity of the normal columnar sample is indistinguishable from that of the low grade SIL. Normalized spectra at 380 nm excitation, (FIG. 14B), indicate that over the wavelength range 400 to 450 nm, the fluorescence intensity of the normal squamous tissue is slightly greater than that of SILs and that of the normal columnar tissue is less than that of SILs. The opposite phenomenon is observed above 580 nm. A careful examination of the spectra of the low grade SIL and high grade SIL indicates that between 460 and 580 nm, the normalized fluorescence intensity of the low grade SIL is higher than that of the high grade SIL. The normalized, mean-scaled spectra (FIG. 14C) enhances the previously observed normalized spectral line shape differences by displaying them relative to the average normalized spectrum of this patient. FIG. 14C indicates that between 400 to 450 nm, the fluorescence intensity of the normal squamous tissue is greater than the mean and that of the normal columnar tissue is less than the mean. The opposite phenomenon is observed above 460 nm. The fluorescence intensity of the SILs is bounded by the intensities of the two normal tissue types over the entire emission spectrum. The low grade SIL and high grade SIL also show spectral line shape differences; above 460 nm, the normalized, mean-scaled fluorescence intensity of the low grade SIL lies above the mean and that of the high grade SIL lies below the mean.

Figure 15A:
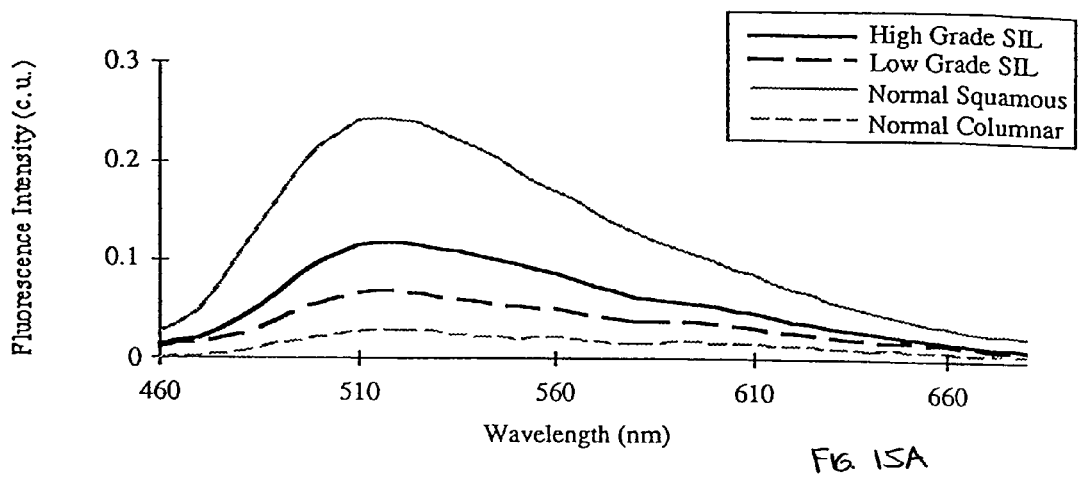
FIG. 15A shows the original spectra.
Figure 15B:
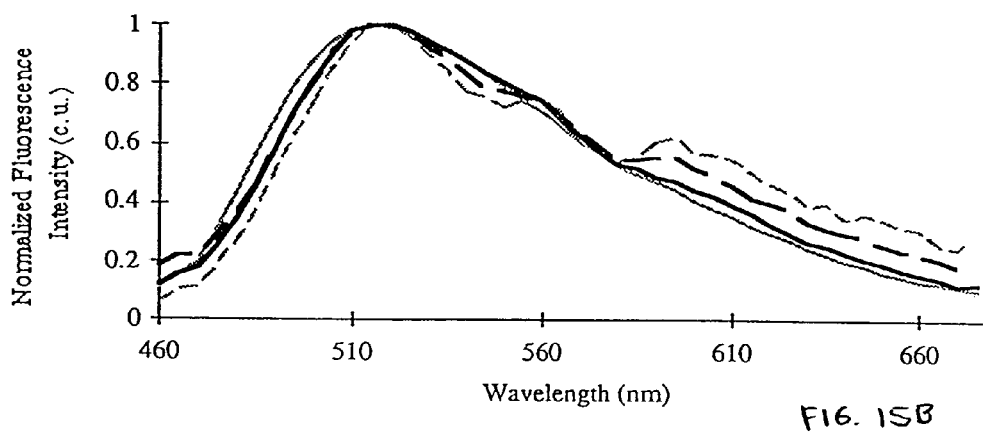
FIG. 15B shows the corresponding normalized spectra.
Figure 15C:
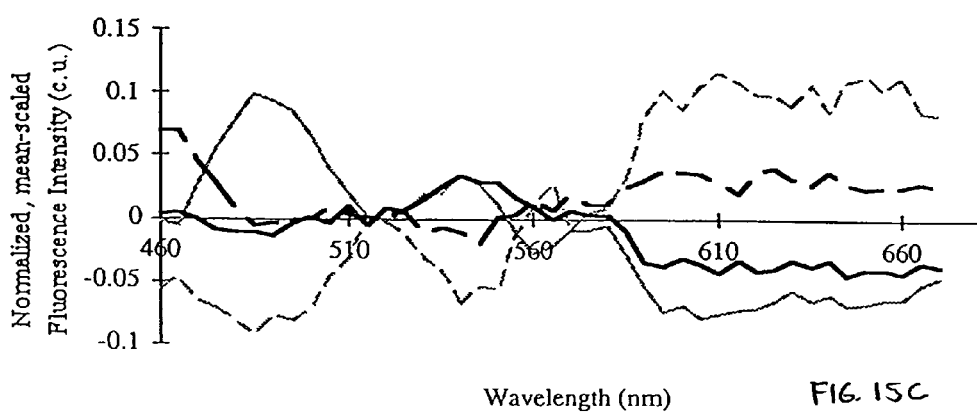
FIG. 15C shows the normalized, mean-scaled spectra at 460 nm excitation from the same patient.

FIGS. 15A, 15B and 15C illustrate original, normalized and normalized, mean-scaled spectra, respectively at 460 nm excitation from the same patient. Evaluation of FIG. 15A indicates that the fluorescence intensity of SILs is less than that of the corresponding normal squamous tissue and greater than that of the corresponding normal columnar sample over the entire emission spectrum. Evaluation of normalized spectra at this excitation wavelength (FIG. 15B) demonstrates that below 510 nm, the fluorescence intensity of SILs is less than that of the normal squamous tissue and greater than that of the corresponding normal columnar tissue. Above, 580 nm, the normalized fluorescence intensity of SILs is less than that of the normal columnar tissue and greater then that of normal squamous tissue. Note that there are spectral line shape differences between the low grade SIL and high grade SIL between 580 and 660 nm; the normalized fluorescence intensity of the low grade SIL is greater than that of the high grade SIL. The normalized, mean-scaled spectra shown in FIG. 15C reflects the differences observed in the normalized spectra relative to the average normalized spectrum of this patient. Below 510 nm, the fluorescence intensity of the normal squamous tissue is greater than the mean, while that of the normal columnar tissue is less than the mean. Above 580 nm, the opposite phenomenon is observed. The fluorescence intensity of the SILs lies between those of the two normal tissue types. Above 580 nm, the fluorescence intensity of the low grade SIL is greater than the mean and that of the high grade SIL is less than the mean.

Figure 16:
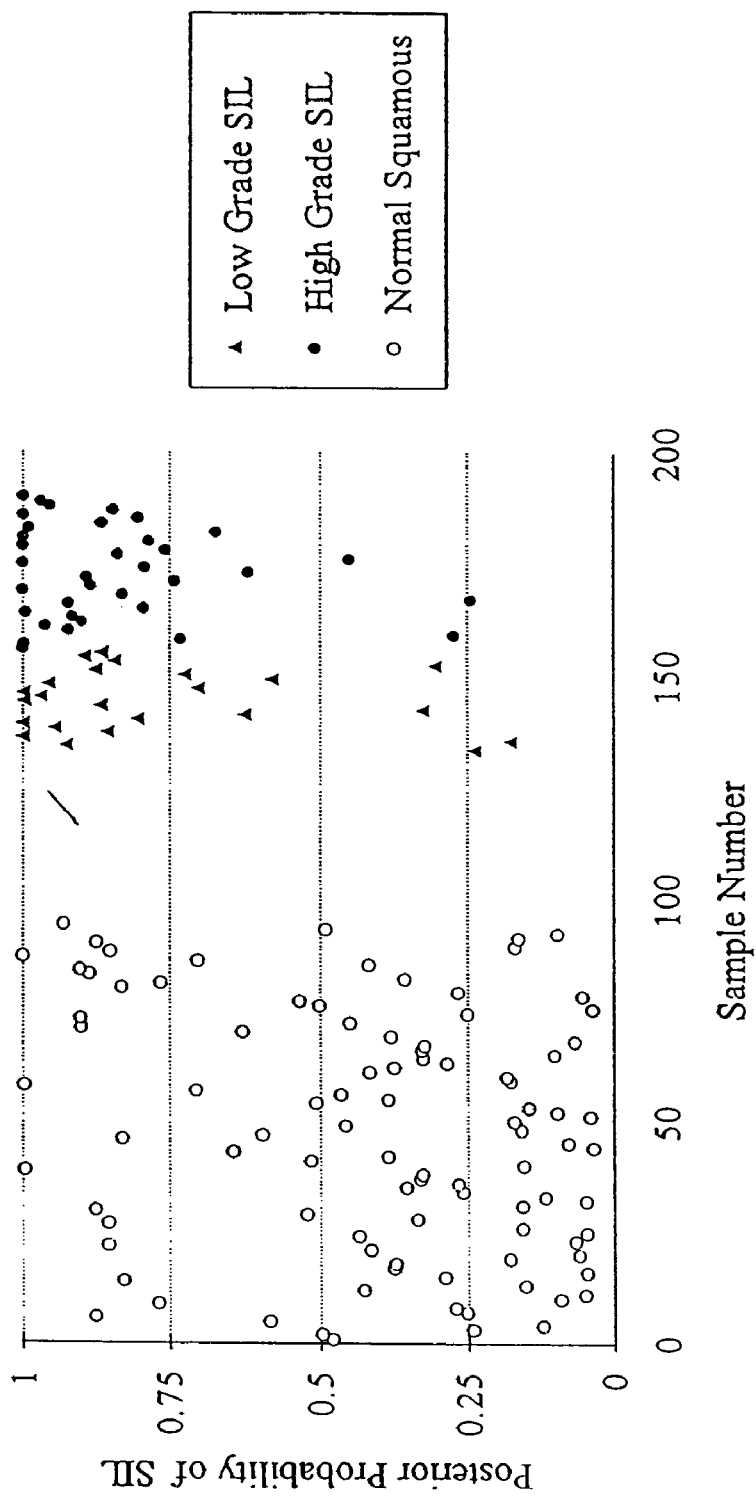
FIG. 16 is a plot of the posterior probability of belonging to the SIL category of all SILs and normal squamous epithelia from the calibration set. Evaluation of the misclassified SILs indicates that one samples with CIN III, two with CIN II, two with CIN I and two with HPV are incorrectly classified.

Principal Component Analysis and Logistic Discrimination: Constituent algorithm (1) which differentiates SILs from normal squamous tissues. A constituent algorithm based on normalized spectra arranged in series at all three excitation wavelengths provided the greatest discrimination between SILs and normal squamous tissues. The algorithm demonstrated an incremental improvement in sensitivity without sacrificing specificity relative to the previously developed constituent algorithm (1) that employed normalized, mean-scaled spectra at 337 nm excitation only. Multivariate statistical analysis of normalized tissue spectra at all three excitation wavelengths, indicated three principal components show statistically significant differences between SILs and normal squamous tissues (Table 7). These three principal components account collectively for 65% of the total variance of the spectral data set. Logistic discrimination was used to develop a classification algorithm to discriminate between SILs and normal squamous epithelia based on these three informative principal components. Prior probabilities were determined by calculating the percentage of each tissue type from the data set: 62% normal squamous tissues and 38% SILs. The cost of misclassification of SIL was optimized at 0.7. Posterior probabilities of belonging to each tissue type were calculated for all samples from the data set, using the known prior probabilities, cost of misclassification of SILs and the conditional joint probabilities calculated from the normal probability density function. FIG. 16 illustrates the retrospective accuracy of the algorithm applied to the calibration data set. The posterior probability of being classified into the SIL category is plotted for all SILs and normal squamous epithelia. FIG. 16 indicates that 92% of high grade SILs and 83% of low grade SILs are correctly classified with a posterior probability greater than 0.5. Approximately 70% of colposcopically normal squamous epithelia are correctly classified with a posterior probability less than 0.5.

The confusion matrix in Table 8 compares the retrospective accuracy of constituent algorithm (1) on the calibration data set to its prospective accuracy on the prediction set. In the confusion matrix, the first row corresponds to the histopathologic classification and the first column corresponds to the spectroscopic classification of the samples. A prospective evaluation of the algorithm's accuracy indicates that there is a small increase in the proportion of correctly classified low grade SILs and no change in the proportion of correctly classified low grade SILs or normal squamous tissues. Note that the majority of normal columnar tissues and samples with inflammation from both calibration and prediction sets are misclassified as SIL using this algorithm. Evaluation of the misclassified SILs from the calibration set indicates that one sample with CIN III, two with CIN II, two with CIN I and two with HPV are incorrectly classified. From the prediction set, two samples with CIN III, one with CIN II, two with CIN I and one with HPV are incorrectly classified as non-SIL.

TABLE 8

| | Normal Squamous | Normal Columnar | Inflammation | LG SIL | HG SIL |
| --- | --- | --- | --- | --- | --- |
| Classification in Calibration Set | | | | | |
| Non SIL | 68% | 8% | 7% | 17% | 9% |
| SIL | 32% | 92% | 93% | 83% | 91% |
| Classification in Prediction Set | | | | | |
| Non SIL | 68% | 29% | 21% | 12% | 9% |
| SIL | 32% | 71% | 79% | 88% | 91% |

Figure 17:
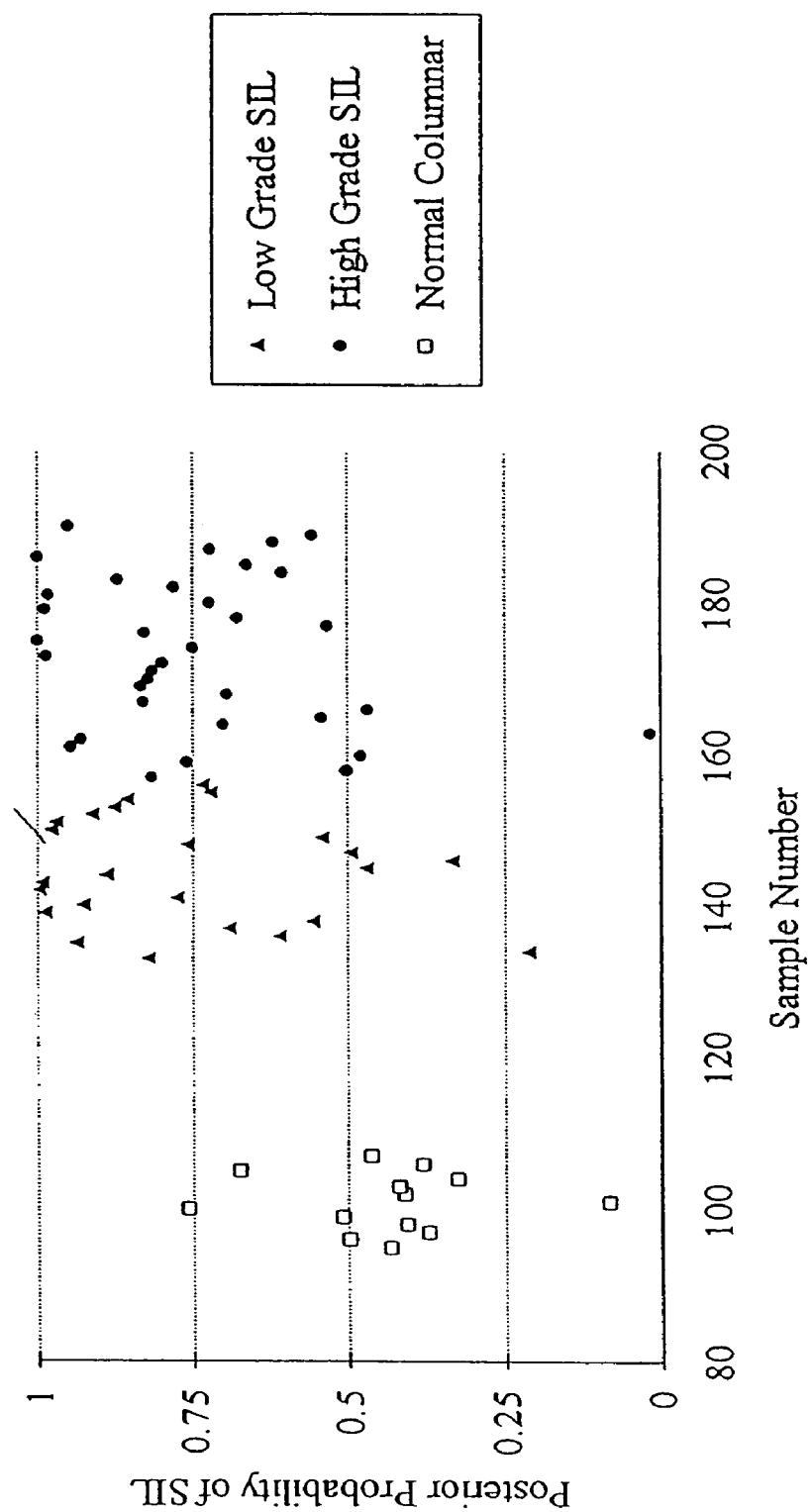
FIG. 17 is a plot of the posterior probability of belonging to the SIL category of all SILs and normal columnar epithelia from the calibration data set. Evaluation of the misclassified SILs indicates that three samples with CIN II, three with CIN I and one with HPV are incorrectly classified.

Constituent algorithm (2) which differentiates SILs from normal columnar tissues. The greatest discrimination between SILs and normal columnar epithelia was achieved using a constituent algorithm based on normalized, mean-scaled spectra at all three excitation wavelengths. This algorithm demonstrated a substantially improved sensitivity for a similar specificity relative to the previously developed constituent algorithm (2) which used normalized, mean-scaled spectra at 380 nm excitation, only. Multivariate statistical analysis of a combination of normalized, mean-scaled tissue spectra at all three excitation wavelengths resulted in four principal components that demonstrate statistically significant differences between SILs and normal columnar epithelia (Table 7). These four principal components collectively account for 80% of the total variance of the spectral data set. Logistic discrimination was employed to develop a classification algorithm to discriminate between SILs and normal columnar epithelia. The prior probabilities were determined to be: 28% normal columnar tissues and 72% SILs. The optimized cost of misclassification of SIL was equal to 0.58. Posterior probabilities of belonging to each tissue type were calculated for all samples from the data set. FIG. 17 illustrates the retrospective accuracy of the algorithm applied to the calibration data set. The posterior probability of being classified into the SIL category is plotted for all SILs and normal columnar samples examined. FIG. 17 graphically indicates that 91% of high grade SILs and 83% of low grade SILs have a posterior probability that is greater than 0.5. 76% of colposcopically normal columnar epithelia are correctly classified with a posterior probability less than 0.5.

The confusion matrix in Table 9 compares the retrospective accuracy of constituent algorithm (2) on the calibration data set to its prospective accuracy on the prediction set. The first column corresponds to the spectroscopic classification and the first row corresponds to the histo-pathologic classification. The prospective accuracy of the algorithm (Table 9) indicates that there is a small increase in the proportion of correctly classified low grade SILs and a small decrease in the proportion of correctly classified high grade SILs; there is approximately a 10% decrease in the proportion of correctly classified normal columnar tissues. Note that the majority of normal squamous tissues and samples with inflammation from both the calibration and prediction sets are misclassified as SIL using this algorithm. Evaluation of the misclassified SILs from the calibration set indicates that three samples with CIN II, three with CIN I and one with HPV are incorrectly classified. From the prediction set, two samples with CIN III, three with CIN II, and three with CIN I are incorrectly classified.

TABLE 9

| | Normal Squamous | Normal Columnar | Inflammation | LG SIL | HG SIL |
|---|---|---|---|---|---|
| Classification in Calibration Set | | | | | |
| Non SIL | 7% | 77% | 27% | 17% | 9% |
| SIL | 93% | 23% | 73% | 83% | 91% |
| Classification in Prediction Set | | | | | |
| Non SIL | 5% | 64% | 27% | 13% | 14% |
| SIL | 95% | 36% | 73% | 87% | 86% |

Figure 18:
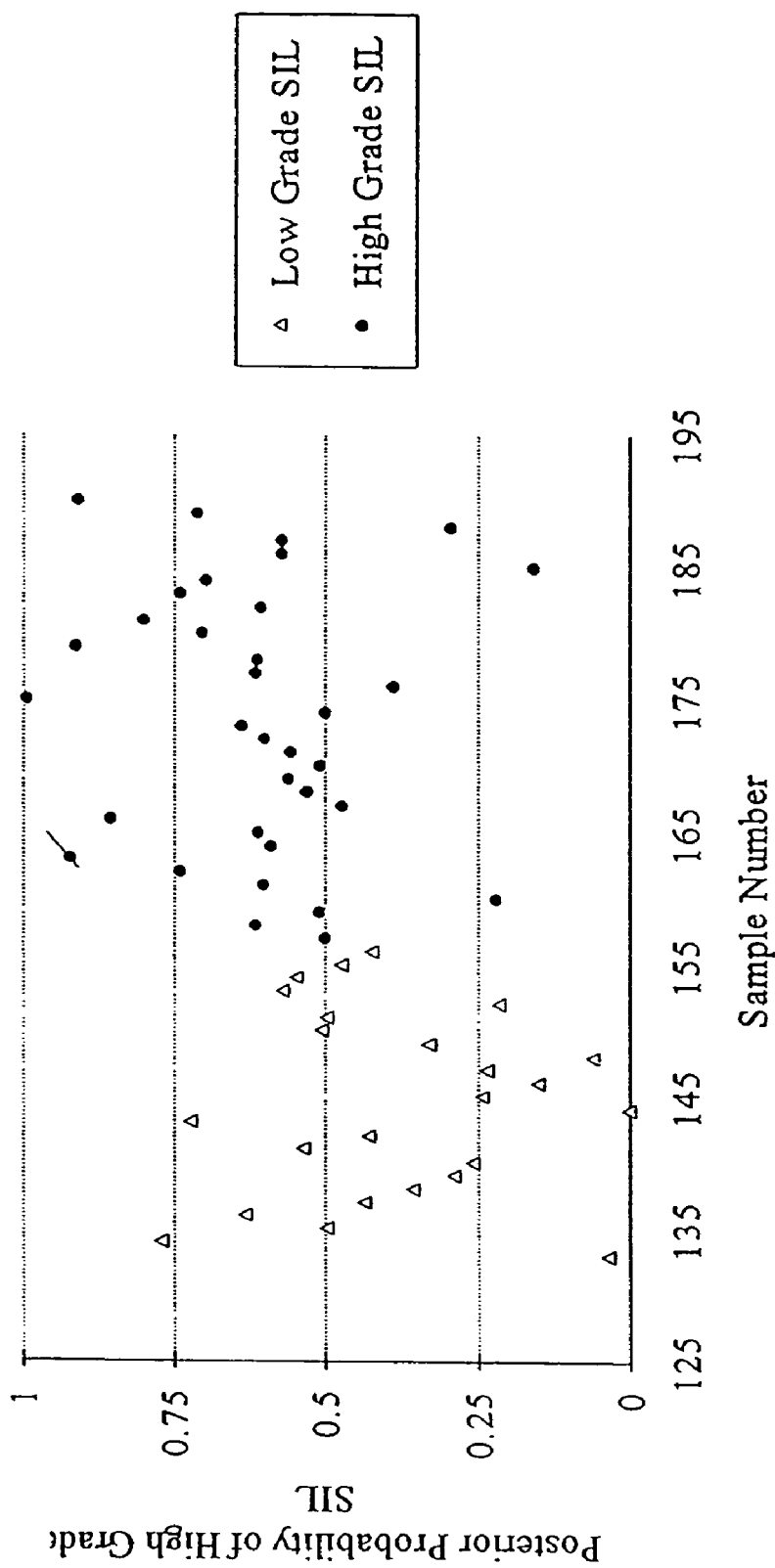
FIG. 18 is a plot of the posterior probability of belonging to the HG SIL category of all SILs from the calibration set. Evaluation of the misclassified HG SILs indicates that three samples with CIN III and three with CIN are incorrectly classified as LG SILs; five samples with CIN I and two with HPV are misclassified as HG SIL.

Constituent algorithm (3) which differentiates High Grade SILs and Low Grade SILs. A combination of normalized spectra at all three excitation wavelengths significantly enhanced the accuracy of the previously developed constituent algorithm (3) which differentiated high SILs from low grade SILs using normalized spectra at 460 nm excitation. Multivariate statistical analysis of normalized spectra at all three excitation wavelengths resulted in four statistically significant principal components, that account collectively for 67% of the total variance of the spectral data set (Table 7). Again, a probability based classification algorithm was developed to differentiate high grade SILs from low grade SILs. The prior probability was: 40% low grade SILs and 60% high grade SILs. The optimal cost of misclassification of high grade SIL was equal to 0.51. Posterior probabilities of belonging to each tissue type were calculated. FIG. 18 illustrates the retrospective accuracy of the algorithm applied to the calibration data set. The posterior probability of being classified into the high grade SIL category is plotted for all SILs evaluated. FIG. 18 indicates that 83% of high grade SILs have a posterior probability greater than 0.5, and 70% of low grade SILs have a posterior probability less than 0.5.

The confusion matrix in Table 10 compares the retrospective accuracy of constituent algorithm (3) on the calibration set to its prospective accuracy on the prediction set. The first column corresponds to the spectroscopic classification and the first row corresponds to the histo-pathologic classification. Its prospective accuracy indicates that there is a 5% decrease in the proportion of correctly classified low grade SILs and no change in the proportion of correctly classified high grade SILs. From the calibration set, six high grade SILs are misclassified; three samples with CIN III and three with CIN II are misclassified as low grade SIL. The misclassified low grade SILs comprise of five samples with CIN I and two with HPV. From the prediction set, five high grade SILs are misclassified; two have CIN III and three have CIN II. Of the ten misclassified low grade SILs from the prediction set, seven have CIN I and three have HPV.

TABLE 10

| | LG SIL | HG SIL |
|---|---|---|
| Classification in Calibration Set | | |
| LG SIL | 69% | 17% |
| HG SIL | 31% | 83% |
| Classification in Prediction Set | | |
| LG SIL | 63% | 19% |
| HG SIL | 37% | 81% |

"Full-parameter" composite screening and diagnostic algorithms. A composite screening algorithm was developed to differentiate SILs and non-SILs (normal squamous and columnar epithelia and inflammation) and a composite diagnostic algorithm was developed to differentiate high grade SILs from non-high grade SILs (low grade SILs, normal epithelia and inflammation). The effective accuracy of both composite algorithms were compared to those of the constituent algorithms from which they were developed and to the accuracy of current detection modalities; see Appendix A, References 5 and 9.

A composite screening algorithm which discriminates between SILs and non SILs. A composite screening algorithm to differentiate SILs from non-SILs was developed using a combination of the two constituent algorithms: algorithm (1) which differentiates SILs from normal squamous tissues and algorithm (2) which differentiates SILs from normal columnar epithelia. The optimal cost of misclassification of SIL was equal to 0.66 for constituent algorithm (1) and 0.64 for constituent algorithm (2). Only the costs of misclassification of SIL of the two constituent algorithms was altered for the development of the composite screening algorithm. These costs were selected to minimize the total number of misclassified samples.

The accuracy of the composite screening algorithm on the calibration and prediction data sets is illustrated in the confusion matrix in Table 11. The first column corresponds to the spectroscopic classification and the first row corresponds to the histo-pathologic classification. Examination of the confusion matrix indicates that the algorithm correctly classifies approximately 90% of high grade SILs and 75% of low grade SILs from the calibration data set. Furthermore, approximately, 80% of normal squamous tissues and 70% of normal columnar epithelia from the calibration set are correctly classified. Evaluation of the prediction set indicates that there is a small change in the proportion of correctly classified high grade SILs and low grade SILs. There is a negligible change in the correct classification of normal squamous and columnar tissues. Note that while 80% of samples with inflammation from the calibration set are incorrectly classified as SIL, only 43% of these samples from the prediction set are incorrectly classified.

TABLE 11

|  | Normal Squamous | Normal Columnar | Inflammation | LG SIL | HG SIL |
| --- | --- | --- | --- | --- | --- |
| Classification in Calibration Set |  |  |  |  |  |
| Non SIL | 79% | 69% | 20% | 26% | 11% |
| SIL | 21% | 31% | 80% | 74% | 89% |
| Classification in Prediction Set |  |  |  |  |  |
| Non SIL | 75% | 69% | 57% | 25% | 14% |
| SIL | 25% | 31% | 43% | 75% | 86% |

A comparison of the accuracy of the composite screening algorithm (Table 11) to that of each of the constituent algorithms (1) (Table 8) and (2) (Table 9) on the same spectral data set indicates that in general, there is less than a 10% decrease in the proportion of correctly classified SILs using the composite screening algorithm relative to using either of the constituent algorithms independently. Note, however, that the proportion of correctly classified normal (squamous and columnar) epithelia is substantially higher using the composite algorithm relative to using either of the constituent algorithms independently. These results confirm that utilization of a combination of the two constituent algorithms, significantly reduces the false-positive rate relative to that using each algorithm independently. Evaluation of the spectroscopically misclassified SILs from the calibration set (Table 6) indicates that only one sample with CIN III, three with CIN II, two with CIN I and four with HPV are incorrectly classified. From the prediction data set (Table 6), two samples with CIN III, four with CIN II, three with CIN I and one sample with HPV are incorrectly classified.

A composite diagnostic algorithm which differentiates High Grade SILs from non-High Grade SILs. A composite diagnostic algorithm which differentially detects high grade SILs was developed using a combination of all three constituent algorithms: algorithm (1) which differentiates SILs from normal squamous tissues, algorithm (2) which differentiates SILs from normal columnar epithelia, and algorithm (3) which differentiates high grade SILs from low grade SILs. The optimal costs of misclassification of SIL was equal to 0.87 for algorithm (1) and 0.65 for algorithm (2); the optimal cost of misclassification of high grade SIL was equal to 0.49 for algorithm (3). Only the costs of misclassification of SIL of constituent algorithms (1) and (2) and the cost of misclassification of high grade SIL of constituent algorithm (3) were altered during development of the composite diagnostic algorithm. These costs were selected to minimize the total number of misclassified samples.

The results of the composite diagnostic algorithm on the calibration and prediction sets are shown in the confusion matrix in Table 12. The first column corresponds to the spectroscopic classification and the first row corresponds to the histo-pathologic classification. The algorithm correctly classifies 80% of high grade SILs, 74% of low grade SILs and more than 80% of normal epithelia. Evaluation of the prediction set using this composite algorithm indicates that there is only a 3% decrease in the proportion of correctly classified high grade SILs and a 7% decrease in the proportion of correctly classified low grade SILs. There is less than a 10% decrease in the proportion of correctly classified normal epithelia. A comparison between the calibration and prediction sets indicates that while more than 70% of samples with inflammation from the calibration data set are incorrectly classified as high grade SIL, only 14% of samples with inflammation from the prediction set are incorrectly identified. Due to the relatively small number of samples examined in this histo-pathologic category, the results presented here do not conclusively establish if the algorithm is capable of correctly identifying inflammation.

TABLE 12

|  | Normal Squamous | Normal Columnar | Inflammation | LG SIL | HG SIL |
| --- | --- | --- | --- | --- | --- |
| Classification in Calibration Set |  |  |  |  |  |
| Non HG SIL | 84% | 77% | 27% | 74% | 20% |
| HG SIL | 16% | 23% | 73% | 26% | 80% |
| Classification in Prediction Set |  |  |  |  |  |
| Non HG SIL | 85% | 69% | 86% | 67% | 23% |
| HG SIL | 15% | 31% | 14% | 33% | 77% |

A comparison of the accuracy of the composite diagnostic algorithm to that of constituent algorithm (3) which differentiates high grade SILs from low grade SILs (Table 10) indicates there is less than a 5% decrease in the proportion of correctly classified high grade SILs and a 5% increase in the proportion of correctly classified low grade SILs using the composite diagnostic algorithm relative to using the constituent algorithm (3). Evaluation of the high grade SILs from the calibration set (Table 12) that were incorrectly classified indicates that three samples with CIN III and four with CIN I are incorrectly classified. From the prediction set, four samples with CIN III and five with CIN II are incorrectly classified.

THIRD EXAMPLE

A goal of the analysis in this third example is to determine if fluorescence intensities at a reduced number of excitation-emission wavelength pairs can be used to re-develop constituent and composite algorithms that can achieve classification with a minimum decrease in predictive ability. A significant reduction in the number of required fluorescence excitation-emission wavelength pairs could enhance the development of a cost-effective clinical fluorimeter. The accuracy of the constituent and composite algorithms based on the reduced emission variables was compared to the accuracy of those that utilize entire fluorescence emission spectra.

Instrumentation

The fluorescence emission spectra obtained with the instrumentation of the Second Example were used to demonstrate the method of this Third Example.

Method

Figure 19A:
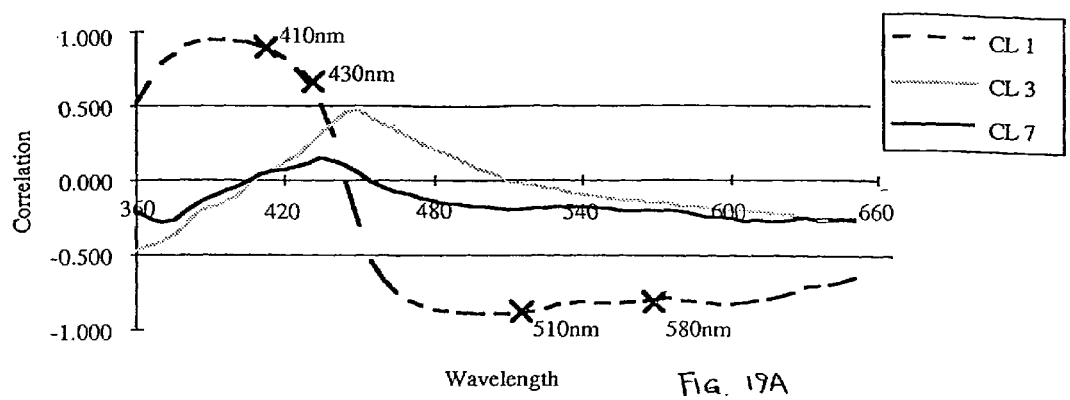
FIGS. 19A, 19B and 19C show component loadings (CL) of diagnostic principal components of constituent algorithm (1), obtained from normalized spectra at 337, 380 and 460 nm excitation, respectively.
Figure 19B:
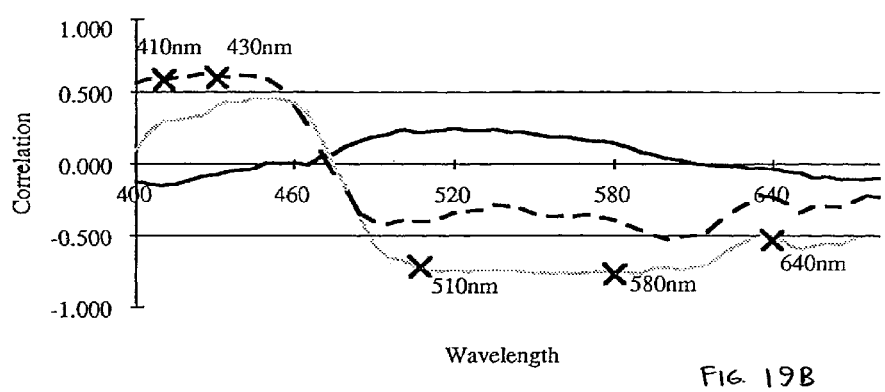
Figure 19C:
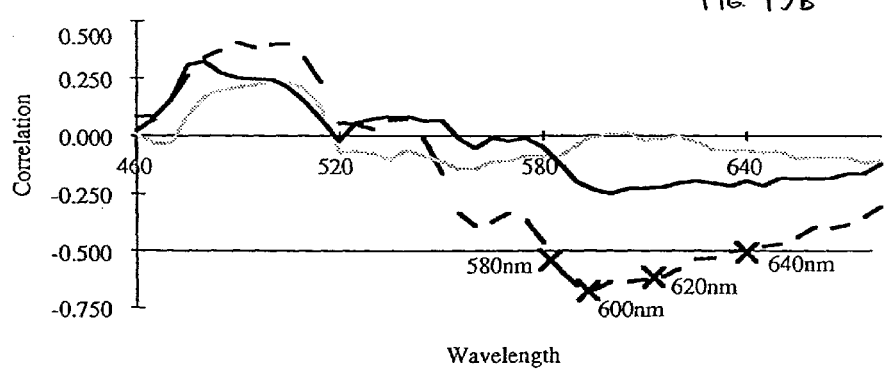
Figure 20A:
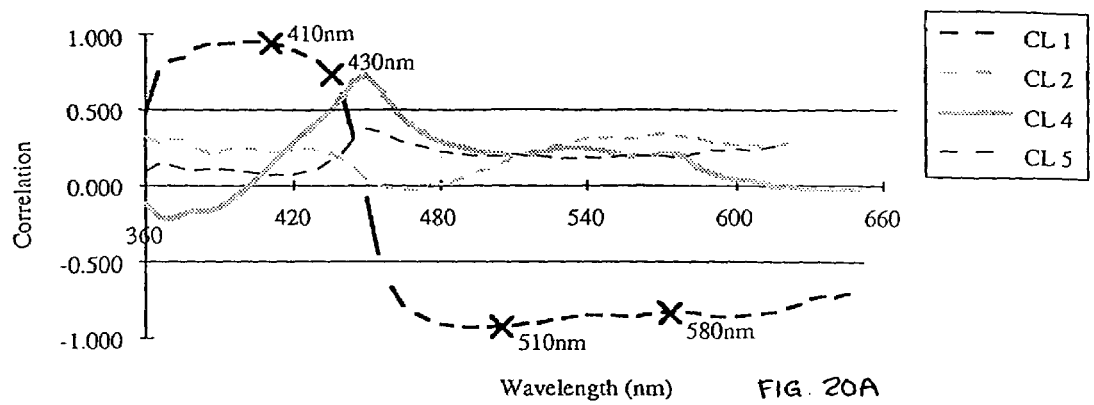
FIGS. 20A, 20B and 20C show component loadings (CL) of diagnostic principal components of constituent algorithm (2), obtained from normalized, mean-scaled spectra at 337, 380 and 460 nm excitation, respectively.
Figure 20B:
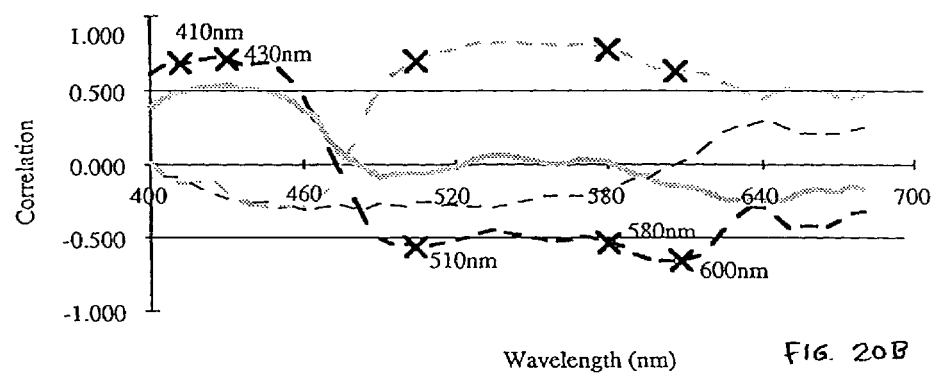
Figure 20C:
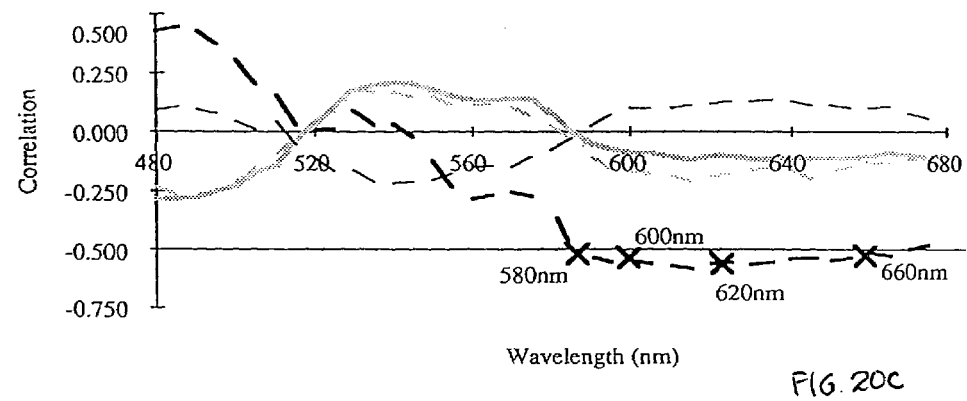

"Reduced-parameter" composite screening and diagnostic algorithms: Component Loadings. A component loading represents the correlation between each principal component and the original pre-processed fluorescence emission spectra at a particular excitation wavelength. FIGS. 19A, 19B and 19C illustrate component loadings of the diagnostically relevant principal components of constituent algorithm (1) obtained from normalized spectra at 337, 380 and 460 nm excitation, respectively. FIGS. 20A, 20B and 20C display component loadings that correspond to the diagnostically relevant principal components of constituent algorithm (2) obtained from normalized, mean-scaled spectra at 337, 380 and 460 nm excitation, respectively. Finally, FIGS. 21A, 21B and 21C display the component loadings corresponding to the diagnostically relevant principal components of constituent algorithm (3), obtained from normalized spectra at 337, 380 and 460 nm excitation, respectively. In each graph shown, the abscissa corresponds to the emission wavelength range at a particular excitation wavelength and the ordinate corresponds to the correlation coefficient of the component loading. Correlation coefficients of the component loading above 0.5 and below −0.5 are considered to be significant.

Figure 21A:
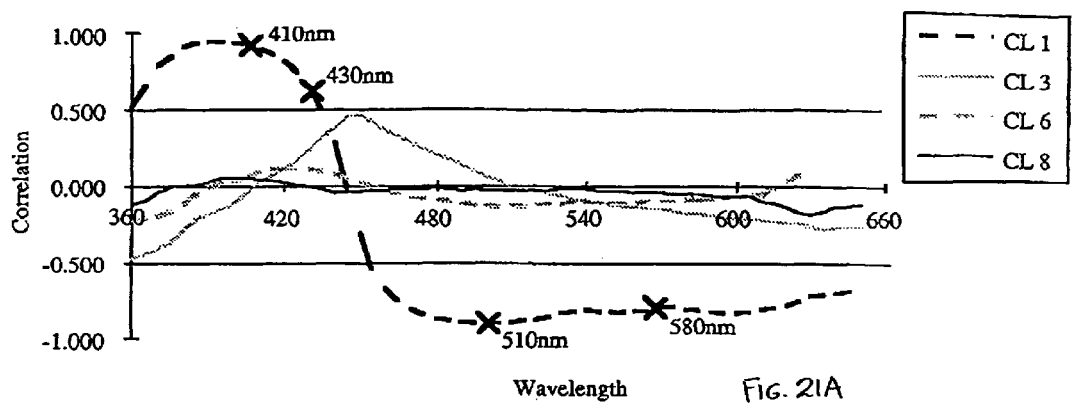
FIGS. 21A, 21B and 21C show component loadings (CL) of diagnostic principal components of constituent algorithm (3), obtained from normalized spectra at 337, 380 and 460 nm excitation, respectively.

FIGS. 19A, 20A and 21A display component loadings of principal components of constituent algorithms (1), (2) and (3), respectively, obtained from pre-processed spectra at 337 nm excitation. A closer examination indicates that component loading 1 is nearly identical for all three algorithms. Evaluation of this loading indicates that it is positively correlated with corresponding emission spectra over the wavelength range 360-440 nm and negatively correlated with corresponding emission spectra over the wavelength range 460–660 nm. All remaining principal components of all three algorithms display a correlation between −0.5 and 0.5, except component loading 4 of algorithm (2) (FIG. 20A) which displays a positive correlation of 0.75 with the corresponding emission spectra at 460 nm.

Figure 21B:
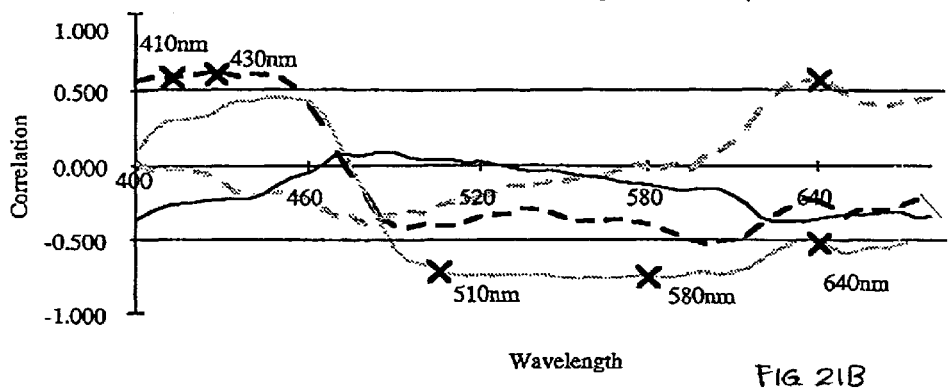

FIGS. 19B, 20B and 21B display component loadings that correspond to the diagnostically relevant principal components of constituent algorithms (1), (2) and (3), respectively obtained from pre-processed spectra at 380 nm excitation. Component loading 1 of all three algorithms is positively correlated with corresponding emission spectra over the wavelength range, 400-450 nm. Between 500-600 nm, only component loading 1 of algorithm (2) (FIG. 20B) is correlated negatively with corresponding emission spectra. However, examination of component loading 3 of algorithm (1) (FIG. 19B) and algorithm (3) (FIG. 21B) indicates that they are also negatively correlated with corresponding emission spectra from 500-600 nm. Only component loading 2 of algorithm (2) (FIG. 20B) is positively correlated with corresponding emission spectra from 500-600 nm. Also note that component loading 3 of algorithm (1) (FIG. 19B) and component loadings 3 and 6 of algorithm (3) (FIG. 21B) display a positive correlation with corresponding emission spectra at approximately 640 nm.

Figure 21C:
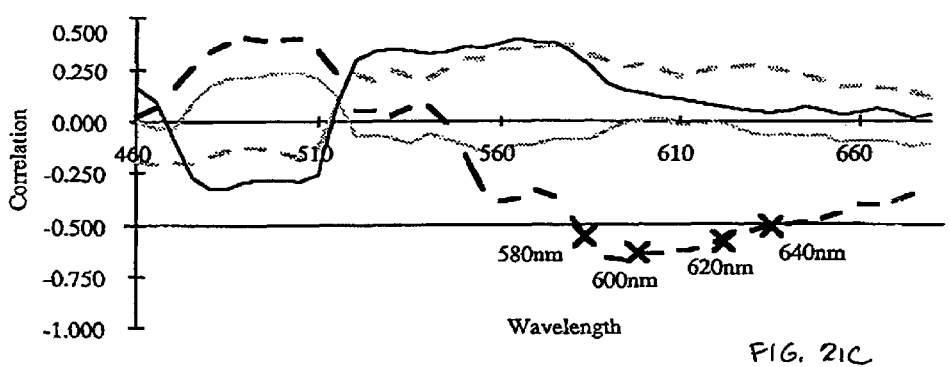

FIGS. 19C, 20C and 21C display component loadings that correspond to the diagnostic principal components of constituent algorithms (1), (2) and (3), respectively obtained from pre-processed spectra at 460 nm excitation. Note that only component loading 1 displays a negative correlation (<−0.5) with corresponding emission spectra for all three algorithms. This component loading is correlated with corresponding emission spectra over the wavelength range 580-660 nm. The remaining principal components of all three algorithms display a correlation between −0.5 and 0.5.

The component loadings at all three excitation wavelengths of all three constituent algorithms were evaluated to select fluorescence intensities at a minimum number of excitation-emission wavelength pairs required for the previously developed constituent and composite algorithms to perform with a minimal decrease in classification accuracy. Portions of the component loadings of the three constituent algorithms most highly correlated (correlation >0.5 or <−0.5) with corresponding emission spectra at each excitation wavelength were selected and the reduced data matrix was then used to regenerate and evaluate the constituent and composite algorithms. It was iteratively determined that fluorescence intensities at a minimum of 15 excitation-emission wavelength pairs are required to re-develop constituent and composite algorithms that demonstrate a minimum decrease in classification accuracy. At 337 nm excitation, fluorescence intensities at two emission wavelengths between 360-450 nm and intensities at two emission wavelengths between 460-660 nm were selected. At 380 nm excitation, intensities at two emission wavelengths between 400-450 nm and intensities at four emission wavelengths between 500-640 nm were selected. Finally, at 460 nm excitation, fluorescence intensities at five emission wavelengths over the range 580-660 nm was selected.

Table 13A lists 18 excitation-emission wavelength pairs needed to re-develop the three constituent algorithms (1), (2) and (3) with a minimal decrease in classification accuracy. These excitation-emission wavelength pairs are also indicated on the component loading plots in FIGS. 19, 20 and 21. The bandwidth at each emission wavelength is 10 nm.

TABLE 13A

| Algorithm (1) ($\lambda_{exc}$, $\lambda_{emm}$) | Algorithm (2) ($\lambda_{exc}$, $\lambda_{emm}$) | Algorithm (3) ($\lambda_{exc}$, $\lambda_{emm}$) |
| --- | --- | --- |
| 337, 410 nm | 337, 410 nm | 337, 410 nm |
| 337, 430 nm | 337, 430 nm | 337, 430 nm |
| 337, 460 nm | 337, 460 nm | 337, 460 nm |
| 337, 510 nm | 337, 510 nm | 337, 510 nm |
| 337, 580 nm | 337, 580 nm | 337, 580 nm |
| 380, 410 nm | 380, 410 nm | 380, 410 nm |
| 380, 430 nm | 380, 430 nm | 380, 430 nm |
| 380, 460 nm | 380, 460 nm | 380, 460 nm |
| 380, 510 nm | 380, 510 nm | 380, 510 nm |
| 380, 580 nm | 380, 580 nm | 380, 580 nm |
| 380, 640 nm | 380, 600 nm | 380, 640 nm |
| 460, 510 nm | 460, 510 nm | 460, 510 nm |
| 460, 580 nm | 460, 580 nm | 460, 580 nm |
| 460, 600 nm | 460, 600 nm | 460, 600 nm |
| 460, 620 nm | 460, 620 nm | 460, 620 nm |
| 460, 640 nm | 460, 660 nm | 460, 640 nm |

Reduced-parameter composite algorithms. Using the fluorescence intensities only at the selected excitation-emission wavelength pairs, the three constituent algorithms were re-developed using the same formal analytical process as was done previously using the entire fluorescence emission spectra at all three excitation wavelengths (FIG. 12). The three constituent algorithms were then independently optimized using the calibration set and tested prospectively on the prediction data set. They were combined as described previously into composite screening and diagnostic algorithms. The effective accuracy of these reduced-parameter composite algorithms were compared to that of the full-parameter composite algorithms developed previously using fluorescence emission spectra at all three excitation wavelengths.

Table 13B contains fluorescence intensities at 15 of the previous 18 excitation-emission wavelength pairs needed to redevelop the three constituent algorithms with a minimal decrease in classification accuracy. This table indicates that three variables are eliminated and the bandwidths of intensities at four excitation-emission wavelength pairs are increased by approximately a factor of four. These results establish that a further reduction in the number of emission variables and an increase in bandwidth minimally affect the classification accuracy of the algorithms. The benefit of eliminating the three emission variables and increasing the bandwidth of four emission variables is that it can reduce the total integration time needed to measure the fluorescence parameters from the tissue.

TABLE 13B

| Excitation, Emission | Old Bandwidth (nm) | New Bandwidth (nm) |
|---|---|---|
| 337 nm, 410 nm | 10 | 80 |
| 337 nm, 430 nm | 10 | Eliminated |
| 337 nm, 460 nm | 10 | 20 |
| 337 nm, 510 nm | 10 | 60 |
| 337 nm, 580 nm | 10 | 60 |
| 380 nm, 410 nm | 10 | Eliminated |
| 380 nm, 430 nm | 10 | Eliminated |
| 380 nm, 510 nm | 10 | 60 |
| 380 nm, 460 nm | 10 | 20 |
| 380 nm, 580 nm | 10 | 10 |
| 380 nm, 600 nm | 10 | 10 |
| 380 nm, 640 nm | 10 | 10 |
| 460 nm, 510 nm | 10 | 10 |
| 460 nm, 580 nm | 10 | 10 |
| 460 nm, 600 nm | 10 | 10 |
| 460 nm, 620 nm | 10 | 10 |
| 460 nm, 640 nm | 10 | 10 |
| 460 nm, 660 nm | 10 | 10 |

Table 14 displays the accuracy of the reduced-parameter composite screening algorithm (based on fluorescence intensities at 15 excitation-emission wavelength pairs) which discriminates between SILs and non-SILs applied to the calibration and prediction sets. The first column corresponds to the spectroscopic classification and the first row corresponds to the histo-pathologic classification. A comparison between the calibration and prediction data sets indicates that there is less than a 10% decrease in the proportion of correctly classified SILs and normal squamous tissues from the prediction set. Note however that there is a 20% increase in the proportion of correctly classified normal columnar epithelia and a 40% increase in the proportion of correctly classified samples with inflammation from the prediction set.

TABLE 14

| | Normal Squamous | Normal Columnar | Inflammation | LG SIL | HG SIL |
|---|---|---|---|---|---|
| Classification in Calibration Set | | | | | |
| Non SIL | 73% | 46% | 13% | 17% | 15% |
| SIL | 27% | 54% | 87% | 83% | 85% |
| Classification in Prediction Set | | | | | |
| Non SIL | 72% | 64% | 50% | 25% | 11% |
| SIL | 28% | 36% | 50% | 75% | 89% |

The accuracy of the reduced-parameter composite screening algorithm (Table 14) was compared to that of the full-parameter composite screening algorithm (Table 11) applied to the same spectral data set. A comparison indicates that in general there is less than a 10% decrease in the accuracy of the reduced-parameter composite algorithm relative to that of the full-parameter composite screening algorithm, except for a 20% decrease in the proportion of correctly classified normal columnar epithelia from the calibration set tested using the reduced-parameter composite screening algorithm (Table 14).

Table 15 displays the accuracy of the reduced-parameter composite diagnostic algorithm that differentially identifies high grade SILs from the calibration and prediction sets. The first column corresponds to the spectroscopic classification and the first row corresponds to the histo-pathologic classification. A comparison of sample classification between the calibration and prediction data sets indicates that there is negligible change in the proportion of correctly classified high grade, low grade SILs and normal squamous epithelia. Note that there is approximately a 20% increase in the proportion of correctly classified normal columnar epithelia and samples with inflammation from the prediction set.

TABLE 15

| | Normal Squamous | Normal Columnar | Inflammation | LG SIL | HG SIL |
|---|---|---|---|---|---|
| Classification in Calibration Set | | | | | |
| Non HG SIL | 79% | 62% | 40% | 65% | 23% |
| HG SIL | 21% | 38% | 60% | 35% | 77% |
| Classification in Prediction Set | | | | | |
| Non HG SIL | 82% | 86% | 64% | 63% | 20% |
| HG SIL | 18% | 14% | 36% | 37% | 80% |

A comparison of the composite diagnostic algorithm based on the reduced emission variables (Table 15) to that using fluorescence emission spectra at all three excitation wavelengths (Table 12) applied to the same spectral data set indicates that in general, the accuracy of the reduced-parameter composite diagnostic algorithm is within 10% of that reported for the full-parameter composite diagnostic algorithm. However, a comparison between Tables 12 and 15 indicates that there is approximately a 15% decrease and a 20% increase in the proportion of correctly classified normal columnar epithelia from the calibration and prediction sets (Table 15), respectively which were tested using the reduced-parameter composite diagnostic algorithm. The opposite trend is observed for samples with inflammation tested using the reduced-parameter composite diagnostic algorithm (Table 15).

Table 16 compares the sensitivity and specificity of the full-parameter and reduced-parameter composite algorithms to that of Pap smear screening, see Appendix A, Reference 5, and colposcopy in expert hands, see Appendix A, Reference 9. Table 16 indicates that the composite screening algorithms have a similar specificity and a significantly improved sensitivity relative to Pap smear screening. A comparison of the sensitivity of the composite screening algorithms to that of colposcopy in expert hands for differentiating SILs from non SILs indicates that these algorithms demonstrate a 10% decrease in sensitivity, but a 20% improvement in specificity. The composite diagnostic algorithms and colposcopy in expert hands discriminate high grade SILs from non-high grade SILs with a very similar sensitivity and specificity. A comparison between the full-parameter and reduced-parameter composite algorithms indicates that the algorithms based on the reduced emission variables demonstrate a similar classification accuracy relative to those that employ fluorescence emission spectra at all three excitation wavelengths.

TABLE 16

| Classification | SILs vs. NON SILs | | HG SIL vs. Non HG SIL | |
|---|---|---|---|---|
| | Sensitivity | Specificity | Sensitivity | Specificity |
| Pap Smear | 62% ± 23 | 68% ± 21 | N/A | N/A |
| Colposcopy in Expert Hands | 94% ± 6 | 48% ± 23 | 79% ± 23 | 76% ± 13 |
| Original Composite Algorithm | 82% ± 1.4 | 68% ± 0.0 | 79% ± 2 | 78% ± 6 |
| Reduced Composite Algorithm | 84% ± 1.5 | 65% ± 2 | 78% ± 0.7 | 74% ± 2 |

FOURTH EXAMPLE

Instrumentation and methods suitable for characterizing tissue of epithelial lined viscus including, for example, the endocervical canal, are now described. It is known that a typical colposcopic tissue patterns occur with some frequency at the transformation zone between the squamous and columnar epithelium in the endocervical canal; see Burke L, Antonioli D A and Ducatman B S. *Colposcopy, Text and Atlas*, pp. 47, 48, 61 and 62, Appleton and Large, Norwalk Conn. (1991). In many women, this transformation zone (also known as the squamocolumnar junction) is located well within the endocervical canal and is not easily subjected to colposcopy or fluorescence spectroscopy with systems that are intended primarily to assess the ectocervix. In addition, cervical lesions that exist on the ectocervix often extend into the endocervical canal, and characterization of the lesion within the endocervical canal is often an important matter. It is therefore desirable to provide a means to subject the endocervical canal, including the transformation zone, to fluorescence spectroscopy.

Referring now to FIGS. 22A through 22F, shown are simplified representations of the cross section of the os of the endocervical canal and surrounding tissue illustrating the locations of the squamous epithelium (SE), columnar epithelium (CE) and transformation zone (TZ) of the uterus at various stages of maturity and for various medical conditions. Specifically. FIG. 22A shows the neonate uterus, FIG. 13B shows the premenarchal uterus, FIG. 22C shows the menarchal uterus, FIG. 22D shows the menstruating uterus, FIG. 22E shows the menopausal uterus, and FIG. 22F shows the postmenopausal uterus. As can be seen, the transformation zone TZ can appear on the ectocervix (for example, menstruating, FIG. 3D), or well within the edocervical canal (for example, postmenopausal, FIG. 3F), or anywhere in between. Since the most common location for CIN and metaplasia is at or near the transformation zone, it is critical that the transformation zone be imaged when conducting fluorescence spectroscopy. This is of particular importance in menopause and postmenopause because most cervical carcinomas occur at this age, and this is when the transformation zone is most deeply within the endocervical canal.

Other general observations of the morphology of the endocervical canal are worthy of note. After the external os, which follows a funnel type opening, the endocervical canal enlarges and gets smaller again at the inner os. The uterus opens to its full size after the internal os by a small angle. The canal can be filled inside with non-neoplastic additional tissue like polyps and synechia. Polyps may fill the canal. Atrophy may be present, which results in an abnormal form of the wall (missing folds). In addition, it is known that stenosis may occur after LEEP treatments.

The folds of the columnar epithelium may typically be several centimeters deep with varying shapes. For example, in one uterus that was studied after removal by hysterectomy, the folds were a maximum of 7.83 mm with a mean depth of 3.38 mm. The folds were observed to have two main directions: axial and with an angle of approximately 30 degrees to the axis of the canal. The top of this pine tree-like form points outwards the canal. The folds are filled with mucus that sticks strongly to the tissue. Flushing with saline solution will not remove the mucus.

Figure 23:
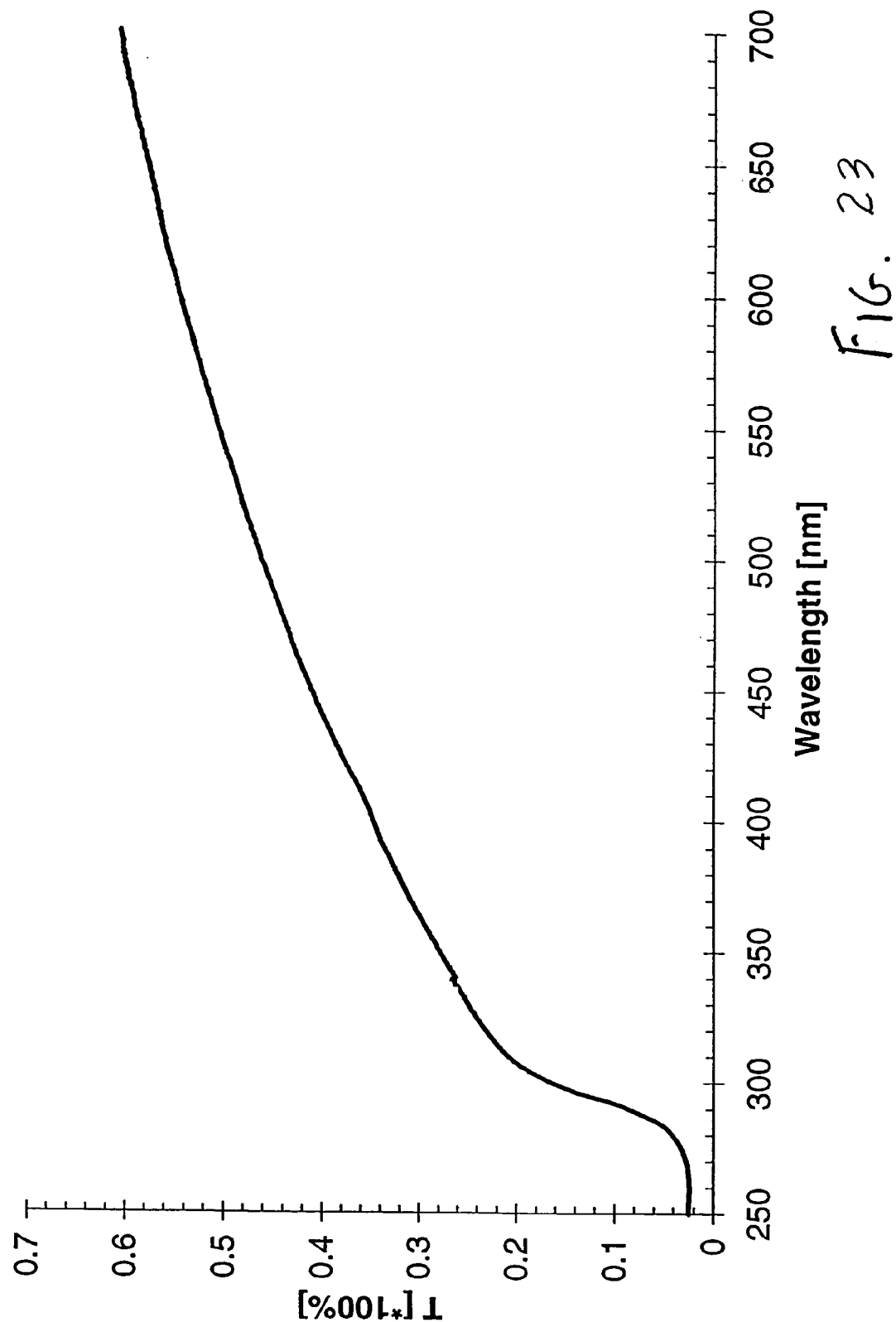
FIGS. 23 and 24 are graphs showing the optical transmission and excitation emission of cervical mucus.
Figure 24:
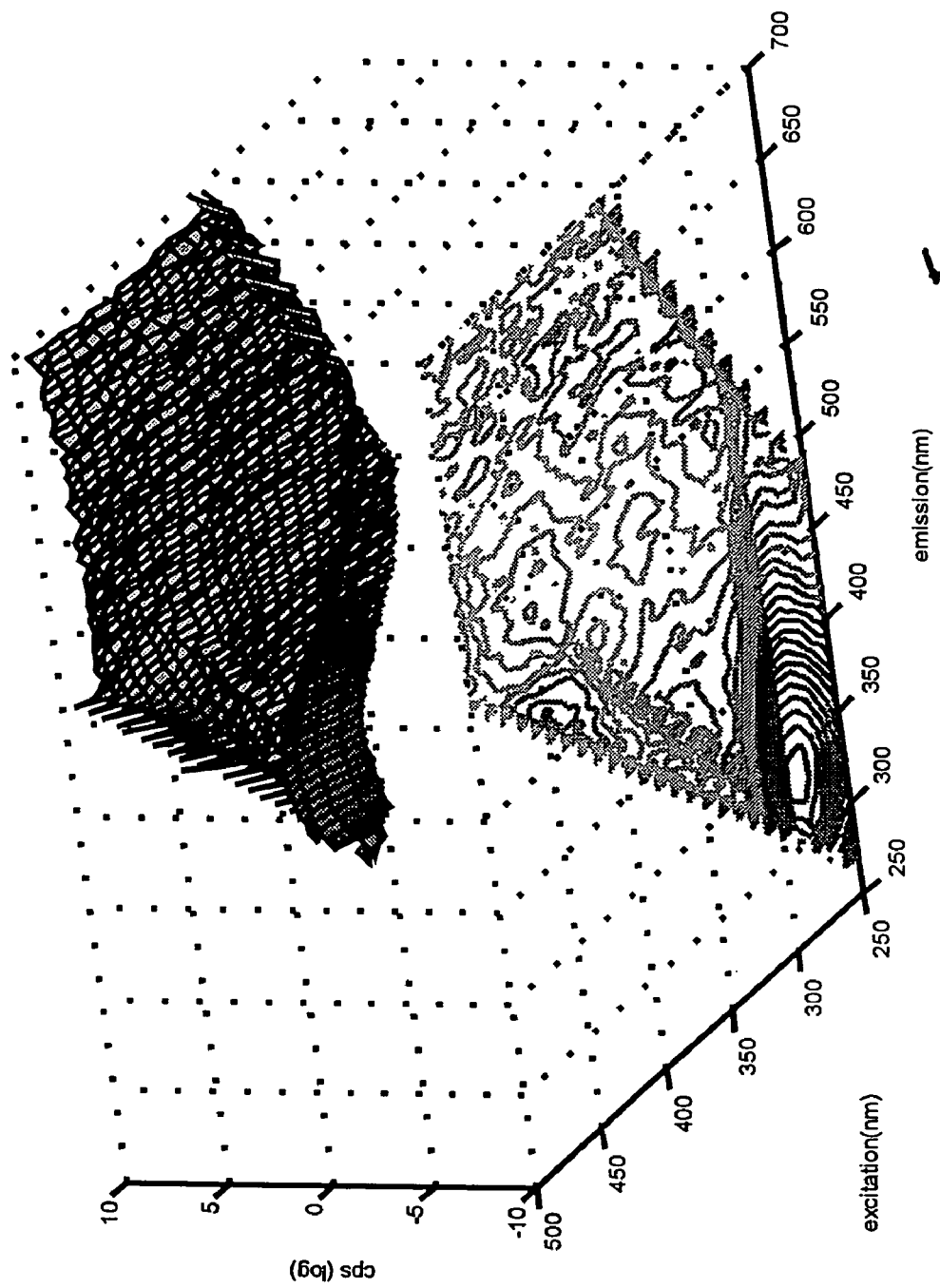

To determine the possible effects of mucus in the endocervical canal, the transmission and fluorescence of several samples of mucus was measured, and the results are presented in graphical form in FIGS. 23 and 24. To produce these graphs, small amounts of mucus were diluted in 10 ml of normal buffered saline solution and placed in a 1 cm pathlength.

As can be seen with reference to FIGS. 23 and 24, the strongest emission of mucus is at 340 nm emission with an excitation at 280 nm. This does not interfere with the measurements described in this example.

Instrumentation

Figure 25:
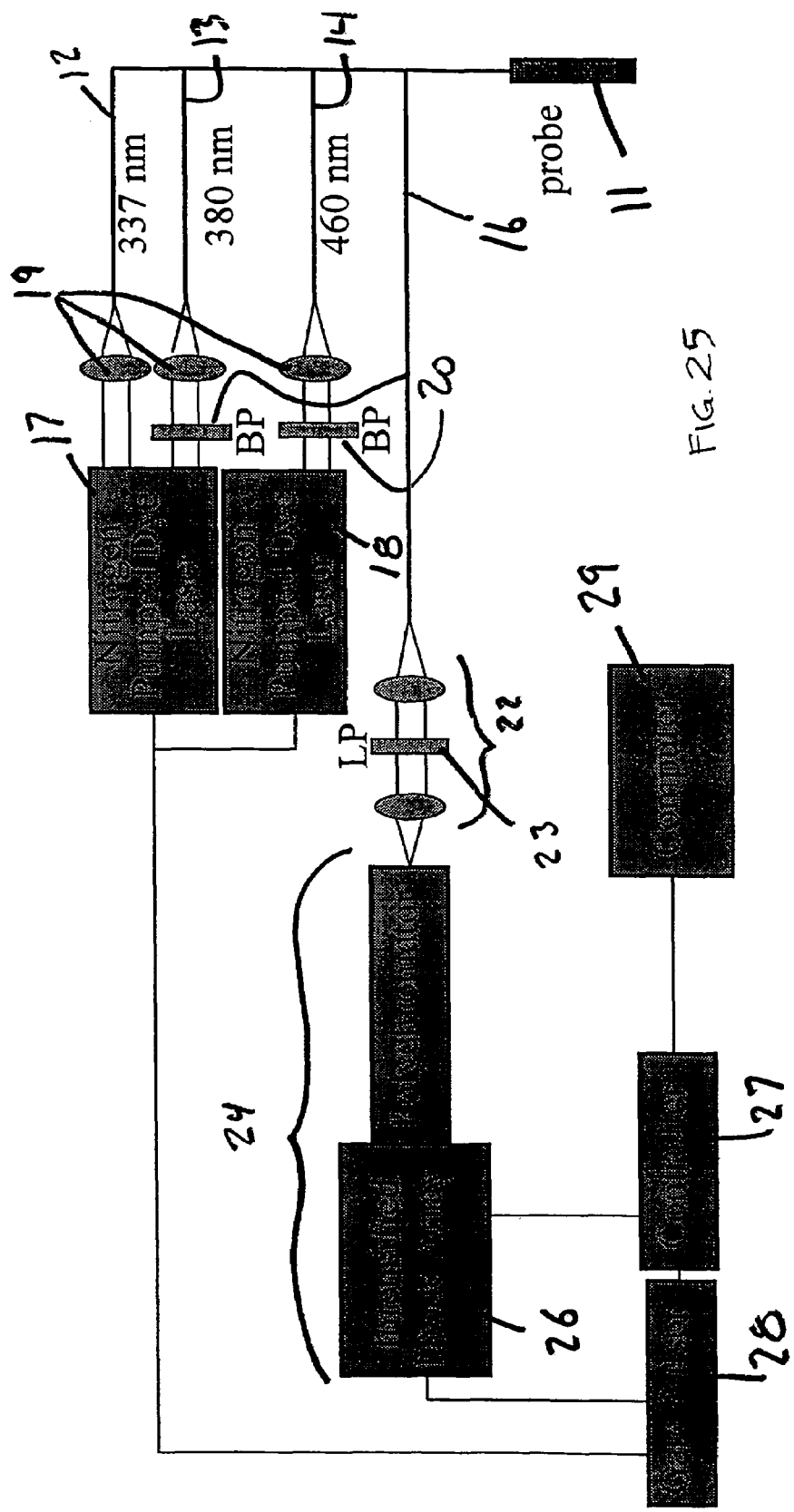
FIG. 25 is an exemplary apparatus usable to measure endocervical tissue fluorescence spectra at three excitation wavelengths.

Referring now to FIG. 25, an apparatus is disclosed using a single pixel optical probe. The apparatus includes endocervical probe 11 which incorporates a number of optical fibers including excitation fibers 12, 13 and 14 and collection fiber 16. The excitation fibers are connected to an illumination source which may be, for example, two nitrogen lasers 17, 18 (LN300C, Laser Photonics) with a dye module. Other illumination sources, for example a Xenon lamp and filter wheel (disclosed in more detail with reference to FIG. 24), may also be used. Other illumination sources may also be acceptable, including, for example, various types of lasers (for example, HeCd or Ag lasers) used with or without dye modules, and various types of so-called white light sources (for example, Xe, Hg, or XeHg lamps) used with filter wheels. This illumination source produces light at frequencies that have been selected for their ability to produce fluorescence in tissue that permits characterization of the tissue. For example light at approximately 337, 380 and 460 nanometers has proven useful. This light is coupled into excitation fibers 12, 13, 14. For coupling, standard Microbench components (Spindler Hoyer) and planoconvex lenses 19 were used. The light coming out of the two dye modules is bandpass filtered by bandpass filters 20 to minimize fluorescence from the dye being coupled into the excitation fibers 12, 13 and 14. Collection fiber 16 collects the fluorescence which is projected through a coupling optics 22 (for example, Microbench, magnification 50/30) into a detector 24, for example an F/3.8 spectrograph (Monospec 18, Thermo Jarrel Ash, Scientific Measurement Systems, Inc.). In the coupling optics 22, longpass filter 23 (for example, color glass filters, Schott) block the reflected excitation light from entering the detector. The spectrograph disperses the light onto an intensified diode array 26. Exemplary diode array 26, electronics and controller 27 are manufactured by Princeton Instruments. The system also includes gate pulser 28 which is used to control the operation of lasers 17 and 18. Lasers 17 and 18 may be controlled, for example at a 30 Hz repetition rate with a 5 nanosecond pulse duration, but other repetition rates and pulse durations may also be acceptable.

The apparatus also includes programmed computer 29 which operates to energize lasers 17 and 18 and to analyze the fluorescence spectra collected by collection fiber 16 in order to characterize the tissue sample under study. The programmed computer 29 is as described in the second example or the third example above.

Figure 26:
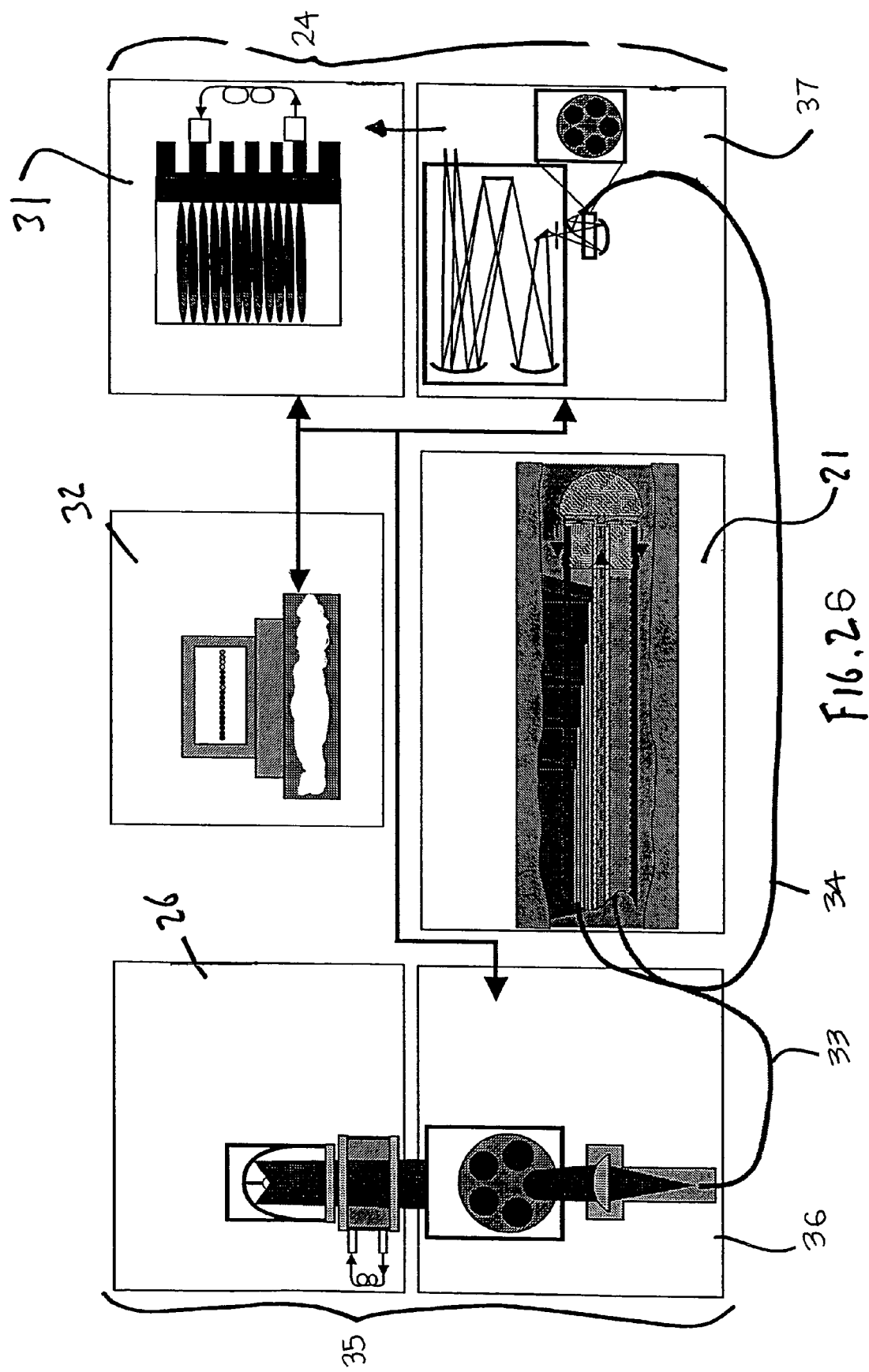
FIG. 26 is another exemplary apparatus usable to measure endocervical tissue fluorescence spectra at three excitation wavelengths.

Although a single pixel probe was used for this example, a multiple pixel optical probe is also useful. Referring now to FIG. 26, an apparatus is disclosed using a multiple pixel optical probe. The apparatus includes a multiple pixel optical probe 21 which incorporates excitation optical fibers 33 and collection optical fibers 34. Excitation optical fibers 33 are connected to receive light from illumination source 35 which may be, for example, a Xenon lamp 26 in combination with a filter wheel 36. Once again, other illumination sources, including for example, the laser source disclosed with reference to FIG. 1, would also be acceptable. As with the apparatus of FIG. 1, illumination source 35 produces light at frequencies that have been selected for their ability to produce fluorescence in tissue that permits characterization of the tissue.

Collection fibers 34 from probe 21 are connected to detector 24 which includes, for example, an imaging spectrograph 37 (for example, a Chromex 250 IS), and a CCD array 31 (for example, a thermoelectric cooled CCD Princeton Instruments EV 578×384). The output of detector 24 is applied to computer 32 which is programmed to control illumination source 35 and to analyze the fluorescence spectra collected by collection fibers 34 and detected by detector 24 using, for example, the analysis methods disclosed in the second example or the third example above.

Figure 27:
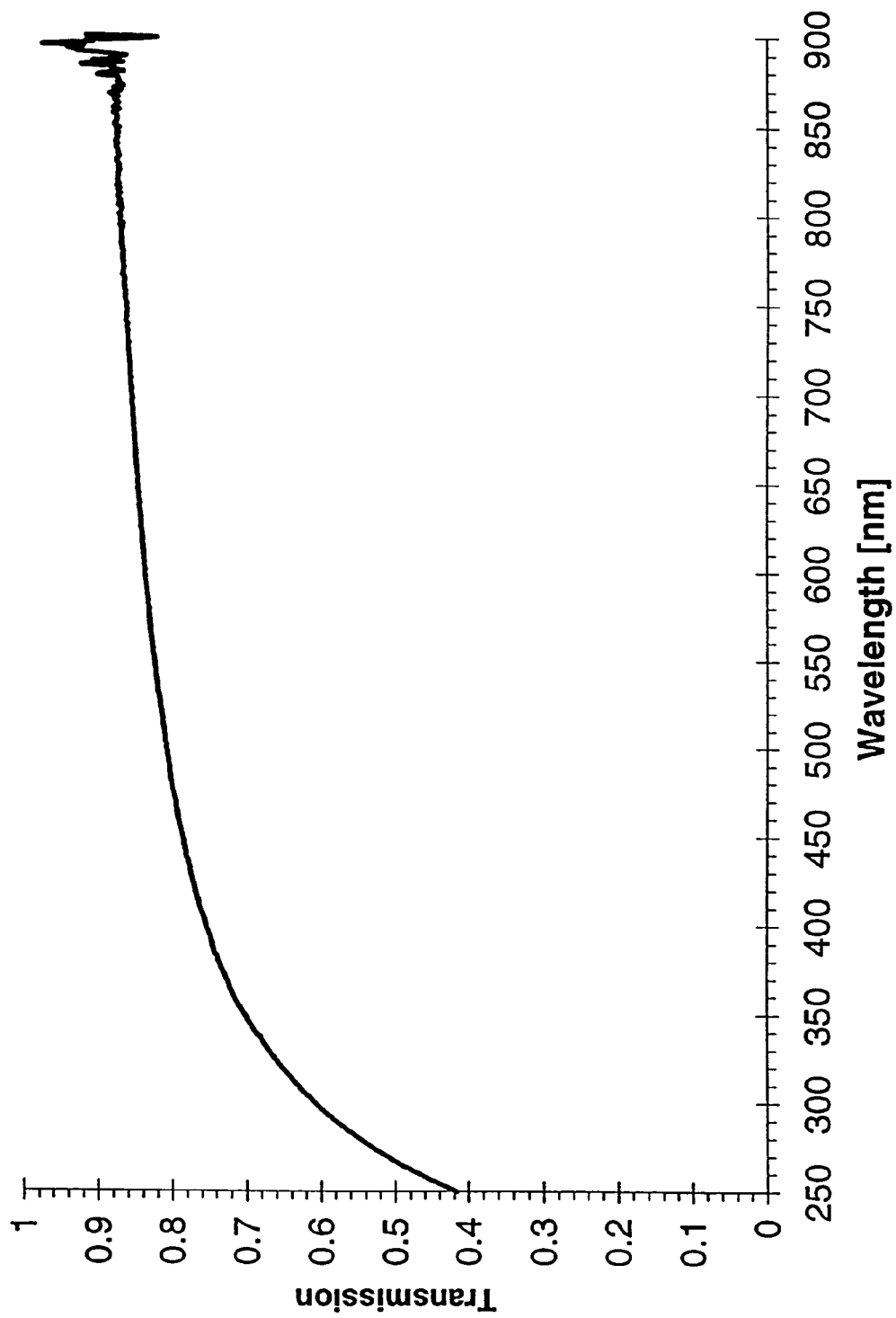
FIGS. 27 and 28 are graphs showing the optical transmission and excitation emission of fluorinated ethylene-propylene (FEP).
Figure 28:
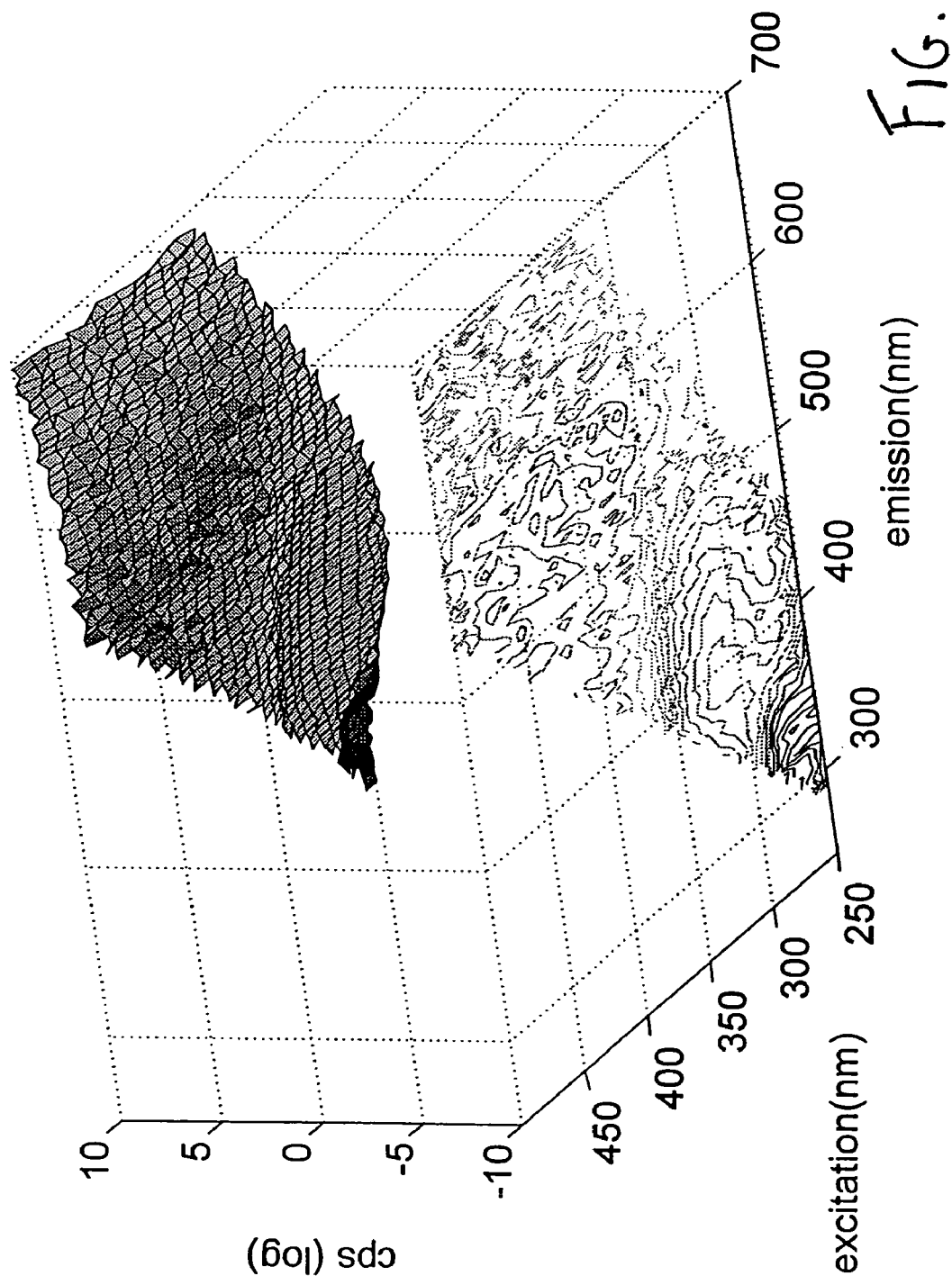

The transmission and fluorescence of FEP tubing, which is a presently preferred material for use as the housing for the probes, was measured and the results are presented in FIGS. 27 and 28. As can be seen with reference to FIGS. 27 and 28, the fluorescence of the FEP tubing is low. However the autofluorescence of the FEP tubing is about $\frac{1}{10}$ of the tissue fluorescence at 337 nm excitation. There is a main emission peak at 400 nm with 320 nm excitation. It was determined that this contribution could be accommodated during the probe calibration procedure discussed below.

Exemplary single and multiple pixel optical probes and various design criteria therefor are described in detail in U.S. patent application Ser. No. 08/693,471, Filed Aug. 2, 1996, which hereby is incorporated herein by reference in its entirety.

Method

In a clinical application, the method of this example has as its purpose the characterization of epithelial viscus tissue, such as, for example, tissue of the endocervical canal. In general, when applied to the characterization of endocervical tissue, the method has as its purposes to: a) identify lesions extending from the ectocervix into the endocervical canal; b) detect the position of the transformation zone if present inside the endocervical canal; and c) identify squamous lesions with columnar involvement inside the endocervical canal. In general, these purposes are accomplished by measuring fluorescence spectra at spatially resolved locations inside the endocervical canal over a substantially cylindrical area of the interior surface of the tissue of the canal, and using probability-based mathematical models to characterize that tissue as a function of the measured spectra. An accepted method to classify cervical tissues is the new Bethesda system as presented in Wright et al., "Pathology of the Female Genital Tract," 156-177, Springer-Verlag, (1994). In accordance with that system, lesions with HPV and CIN are classified as squamous intraepithelial lesions (SILs) where they may be further separated as high grade SIL (CIN II, CIN III, CIS) and low grade SIL (CIN I, HPV). Normal, metaplastic and non-specific inflammation tissues are classified as non-SILs.

Before beginning a clinical procedure, the measuring apparatus should be calibrated. To calibrate the instrumentation (as shown, for example in FIGS. 23 and 23), the background signals are obtained without any excitation which reflects the dark current of the device. This background is stored and is automatically subtracted from any fluorescence measurement. Next, the autofluorescence of the probe is determined, for example, by placing the probe in a brown bottle containing sterile $H_2O$ and measuring fluorescence spectra with the excitation light on. This signal is not subtracted from the tissue fluorescence, however it may be subtracted if desired. In order to confirm calibration, a standard rhodamine solution (OD 0.446725, (=550 nm, 1 cm pathlength) may be measured. Based on previous clinical work, Rhodamine has been shown to have approximately twice the intensity of squamous cervical tissue fluorescence.

During spectral measurement of tissue, if improvement in the signal to noise ratio is desired, the spectra may be accumulated 100 and 200 times, respectively at 380 and 460 nm At 337 nm 50 accumulations have proven sufficient. However, other methods to improve the signal to noise ratio may also be used. For all three wavelengths a different background subtraction file may be used with the corresponding accumulations.

During a clinical procedure, it is desired to obtain fluorescence spectra at preferably three excitation wavelengths along the substantially cylindrical surface of the entire endocervical canal with a spatial resolution of approximately 1.5 mm. This may be accomplished by use of either of the apparatus of FIG. 23 or 24 with any suitable optical probe, including a single pixel probe, ring probe, line probe, or area probe. During a procedure, the outer housing of the probe is placed and advanced to the internal os of the endocervical canal. Fluorescence measurement are then started. In the case of a single pixel probe, the single measuring pixel is advance both axially and angularly within the housing in order to image a sufficient number of pixels over the substantially cylindrical tissue surface. When using a ring probe, the measuring ring of pixels is advance axially in order to image a sufficient number of pixels over the substantially cylindrical tissue surface. When using a line probe, the measuring line of pixels is incremented angularly in order to image a sufficient number of pixels over the substantially cylindrical tissue surface; for example, four individual measurement may be taken, one each at 12, 3, 6, and 9 o'clock (i.e., every 90°). This procedure takes approximately 3 minutes to complete.

Either before or during a procedure, saline solution may be flushed over the tissue in order possibly to improve measurement accuracy by removing mucus or blood or loose tissue form the measurement site.

In general, if the margin of the first specimen at the endocervical side is free of dysplasia or cancer and the second specimen shows no changes it may be assumed that the canal is in a normal condition. If this margin is involved with changes it may be assumed that the first 5 mm of the canal are in an abnormal state. If the margin of the endocervical specimen contains no changes it may be assumed that the margins extend no deeper than 2 cm. If this specimen shows abnormal cells it may be assumed that the measurements in the canal were abnormal even after 5 mm. If the second specimen is marked as metaplasia it may be assumed that the transformation zone is inside the endocervical canal.

If the first specimen shows metaplasia the transformation zone is located around the os or on the ectocervix.

Figure 29:
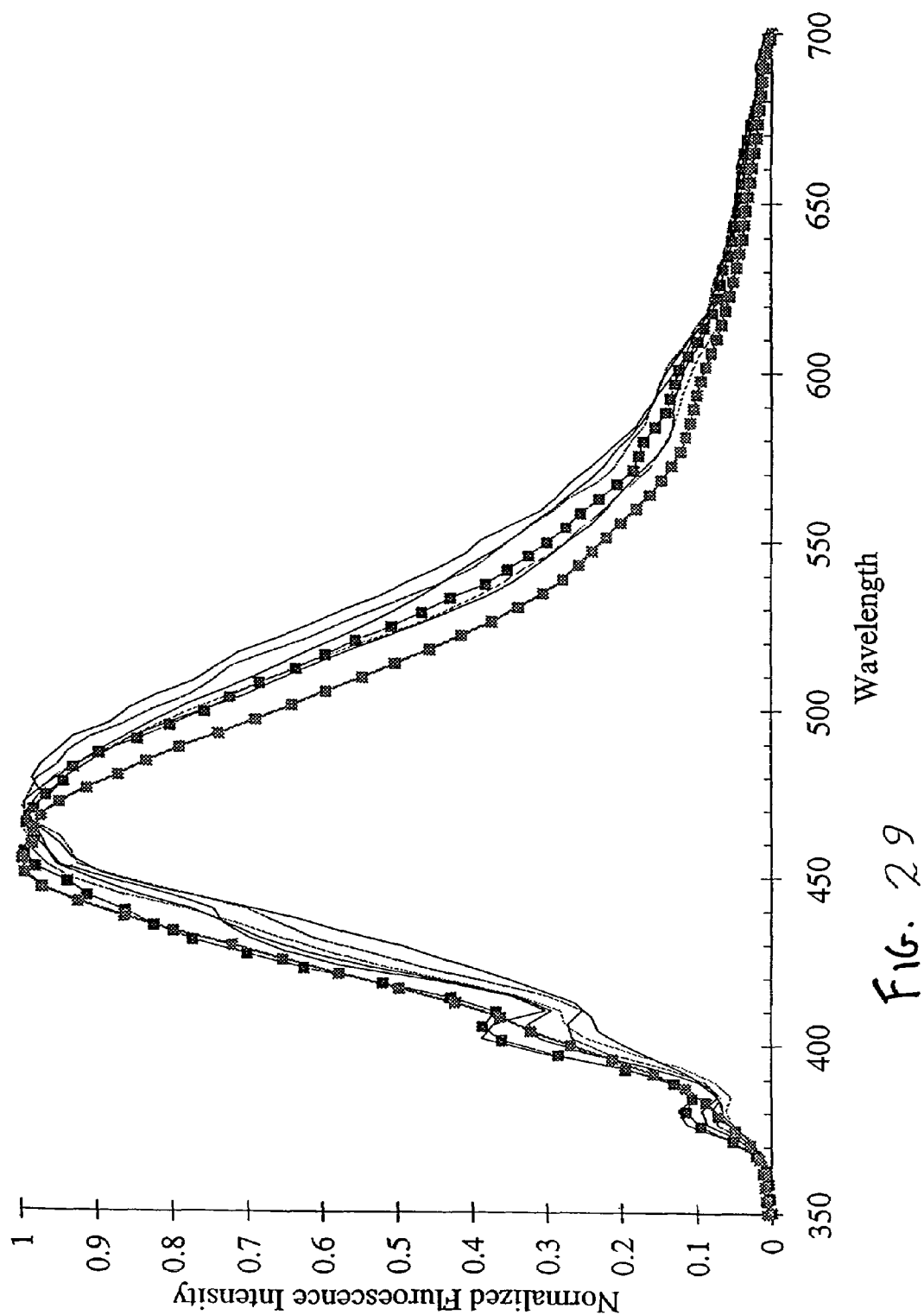
FIGS. 29, 30 and 31 are exemplary fluorescence spectra obtained from endocervical canal tissue.
Figure 30:
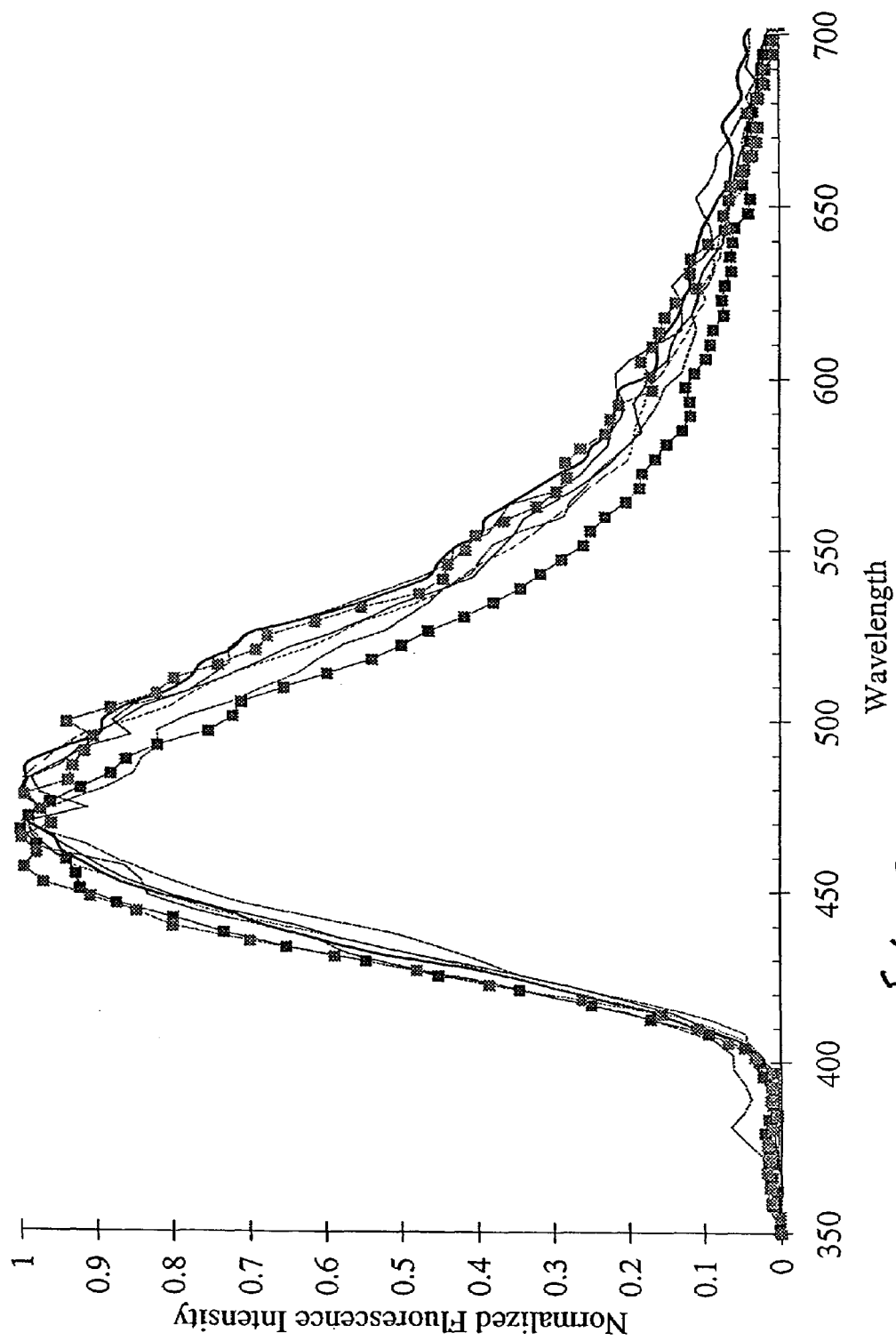
Figure 31:
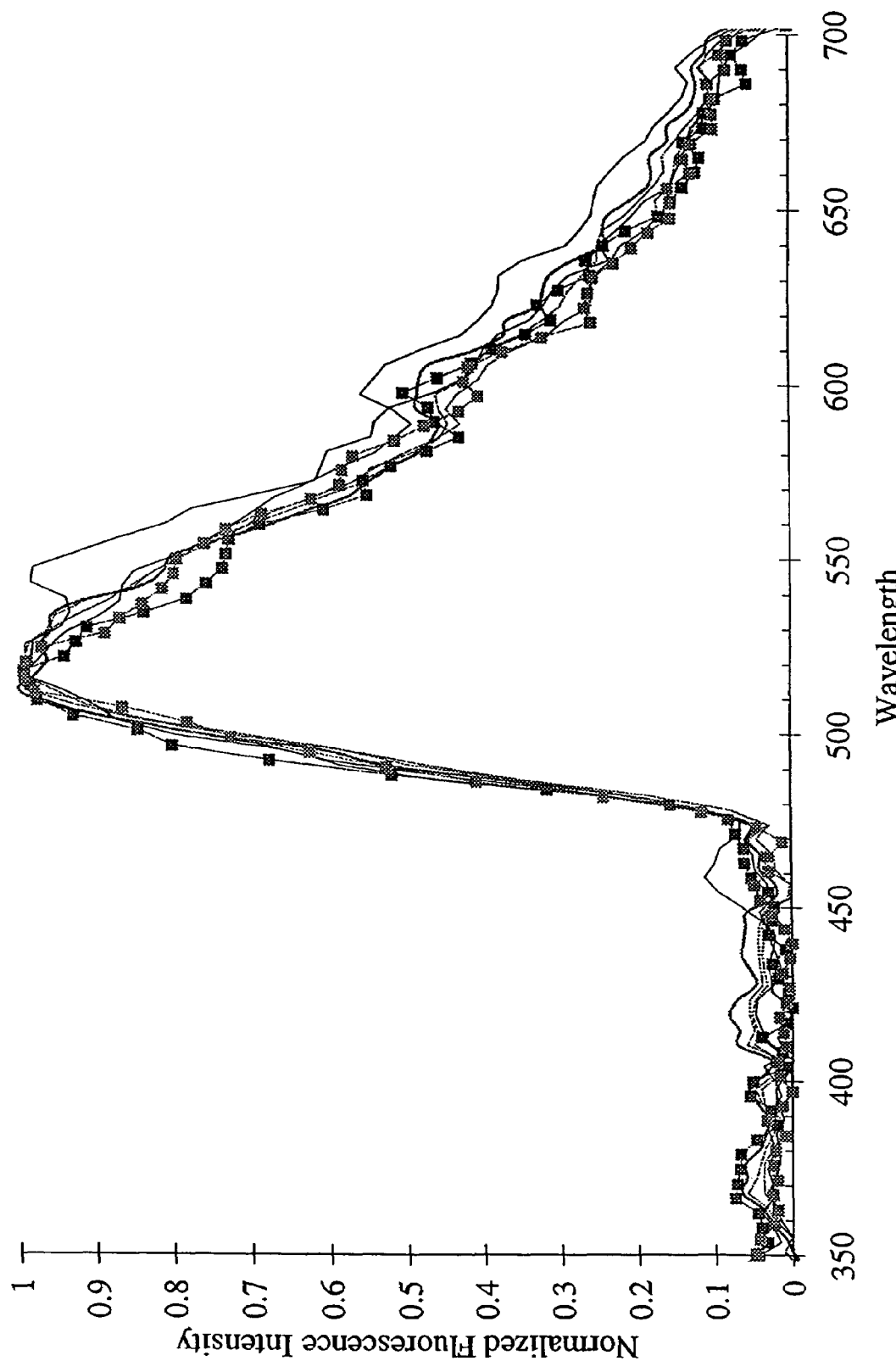

FIGS. 29, 30 and 31 present groups of normalized fluorescence intensity spectra obtained in vivo from endocervical canals of several different patients using the method and instrumentation of this example. In particular, FIG. 29 is a group of normalized fluorescence intensity spectra obtained with 337 nm excitation, FIG. 30 is a group of fluorescence intensity spectra obtained using 380 nm excitation, and FIG. 31 is a group of normalized fluorescence intensity spectra obtained using 460 nm excitation.

Clinical Methods for Performing the Composite Screening Algorithms of Examples 2, 3 and 4

In a clinical setting, the following exemplary steps are carried out to perform the composite screening algorithm of Examples 2, 3 and 4 above.

The instrument is turned on and calibrated. Next, the prior probability that the patient to be measured has SIL is entered. This probability may be derived from statistics from the general population, or may be derived from patient-specific data collected, for example, from a prior colposcopy. Next, a speculum is inserted and the cervix is observed. Acetic acid may be applied to the cervix, if desired.

The probe is directed to the cervix, ensuring that areas desired for screening will be illuminated. Multiple placements of the probe may be necessary. Using the probe, the cervix is illuminated with excitation at approximately 337 nm, 380 nm and 460 nm. The probe will record resulting fluorescence data.

Data from each spatial location assessed is analyzed to indicate whether the tissue is SIL or not. Analysis steps carried out include the following.

1. Data recorded from each spatial location on the cervix is pre-processed in two ways: normalization, and normalization followed by mean scaling. Similarly pre-processed data obtained at each excitation wavelength are concatenated into a vector for each spatial location assessed.
2. The normalized data vector from each site (Dn') is multiplied by the reduced eigenvector matrix stored in memory (Cn'). Cn' contained only those eigenvectors which displayed statistically significant differences for samples to be classified by constituent algorithm 1.
3. The posterior probabilities that a sample is SIL or normal squamous epithelium are calculated using Bayes theorem. In this calculation, the mean values and standard deviations of the PC scores for normal squamous epithelium and SILs and optimal costs of misclassification stored in memory and the entered prior probability are used.
4. The normalized, mean-scaled prediction data vector (Dnm') is multiplied by the reduced eigenvector matrix from normalized, mean-scaled spectral data stored in memory (Cnm'). Cnm' contains only those eigenvectors which displayed statistically significant differences for samples to be classified by constituent algorithm 2.
5. The posterior probabilities that a sample is SIL or normal columnar epithelium are calculated using Bayes theorem. In this calculation, the mean values and standard deviations of the PC scores for normal columnar epithelium and SILs and optimal costs of misclassification stored in memory and entered prior probabilities are used.
6. Using constituent algorithm 1, sites with a posterior probability of being normal squamous epithelium greater than a threshold value are classified as non-SIL. Remaining sites are classified based on the output of constituent algorithm 2. Using constituent algorithm 2, sample with a posterior probability of being normal columnar epithelium greater than a threshold are classified as non-SIL. The remaining samples are classified as SIL. These tissue classifications may then be displayed in an easily understandable way, for example, by displaying an image of the cervix with the different tissue types displayed as different colors.

To use the composite diagnostic algorithm in clinical practice, the following exemplary steps are carried out.

The instrument is turned on and calibrated. The prior probability that the patient to be measured has SIL and HGSIL is entered. Once again, this probability may be derived from statistics from the general population, or may be derived from patient-specific data collected, for example, from a prior colposcopy. Next, a speculum is inserted and the cervix is observed. Acetic acid may be applied to the cervix, if desired.

The probe is directed to the cervix, ensuring that areas desired for screening will be illuminated. Multiple placements of the probe may be necessary. Using the probe, the cervix is illuminated with excitation at approximately 337 nm, 380 nm and 460 nm. The probe will record resulting fluorescence data.

Data from each spatial location assessed is analyzed to indicate whether the tissue is HGSIL or not. Analysis steps carried out include:

1. Data recorded from each spatial location on the cervix is pre-processed in two ways: normalization, and normalization followed by mean scaling. Similarly pre-processed data obtained at each excitation wavelength are concatenated into a vector for each spatial location assessed.
2. The normalized data vector from each site (Dn') is multiplied by the reduced eigenvector matrix stored in memory (Cn'). Cn' contained only those eigenvectors which displayed statistically significant differences for samples to be classified by constituent algorithm 1.
3. The posterior probabilities that a sample is SIL or normal squamous epithelium are calculated using Bayes theorem. In this calculation, the mean values and standard deviations of the PC scores for normal squamous epithelium and SILs and optimal costs of misclassification stored in memory and the entered prior probability are used.
4. The normalized, mean-scaled prediction data vector (Dnm') is multiplied by the reduced eigenvector matrix from normalized, mean-scaled spectral data stored in memory (Cnm'). Cnm' contains only those eigenvectors which displayed statistically significant differences for samples to be classified by constituent algorithm 2.
5. The posterior probabilities that a sample is SIL or normal columnar epithelium are calculated using Bayes theorem. In this calculation, the mean values and standard deviations of the PC scores for normal columnar epithelium and SILs and optimal costs of misclassification stored in memory and entered prior probabilities are used.
6. The normalized prediction data vector (Dn') is multiplied by the reduced eigenvector matrix from normalized spectral data of the calibration set (Cn'). Cn' contains only those eigenvectors which displayed statistically significant differences for samples to be classified by constituent algorithm 3.

7. The posterior probabilities that a sample HGSIL or LGSIL are calculated using Bayes theorem. In this calculation, the mean values and standard deviations of the PC scores for HGSILs and LGSILs and optimal costs of misclassification stored in memory and entered prior probabilities are used.

8. Using constituent algorithm 1, sample with a posterior probability of being normal squamous epithelium greater than a threshold are classified as non-SIL. Remaining samples are classified based on the output of constituent algorithm 2. Using constituent algorithm 2, sample with a posterior probability of being normal columnar epithelium greater than a threshold are classified as non-SIL. Remaining samples are classified based on the output of constituent algorithm 3. Using constituent algorithm 3, samples with a posterior probability of being LGSIL greater than a threshold are classified as LGSIL. The remaining samples are classified as HGSIL. These tissue classifications may then be displayed in an easily understandable way, for example, by displaying an image of the cervix with the different tissue types displayed as different colors.

The previous examples and clinical methods are included to demonstrate specific embodiments. It will be appreciated by those of skill in the art that the techniques disclosed in the examples and the clinical methods represent techniques discovered by the inventors to function well in the practice of the technology, and thus can be considered to constitute specific modes for its practice. Those of skill in the art will also appreciate in light of the present disclosure, that variations and modifications of the methods and apparatus disclosed herein are possible, and that practical alternatives to and equivalents of the various elements of the methods and apparatus may be practiced without departing from the scope and spirit of the invention. Accordingly, the description and applications as set forth herein are illustrative and are not intended to limit the scope of the invention, which is defined in the following claims.

APPENDIX A

1. Wright T. C., Kurman R. J., Ferenczy A. (1994) Cervical Intraepithelial Neoplasia. In *Pathology of the Female Genital Tract*. (Edited by A. Blaustein), New York.
2. American Cancer Society (1995) Cancer Facts and Figures, 12.
3. Kurman R. J., Henson D. E., Herbst A. L., Noller K. L., Schiffman M. H. (1994) Interim guidelines of management of abnormal cervical cytology. JAMA 271, 1866-1869.
4. World Health Organization, Geneva (1988) Cytological Screening in the Control of Cervical Cancer: Technical Guidelines.
5. Fahey M. T., Irwig L., Macaskill P. (1995) Meta-analysis of Pap test accuracy. American J Epidemiology 141(7), 680-689.
6. Wilkinson E. J. (1990) Pap Smears and screening for cervical neoplasia. Clin Obstet Gynecol 33, 817-825.
7. Koss L. G. (1989) The Papanicolaou test for cervical cancer detection: a triumph and a tragedy. JAMA, 737-743.
8. Burke L., Ducatman B. S. (1991) Colposcopy, text and atlas. Appleton and Large, Norwalk, Conn.
9. Mitchell M F. (1994) Accuracy of Colposcopy. Consultations in Obstetrics and Gynecology 6(1), 70-73.
10. Richards-Kortum R. R., Rava R. P., Fitzmaurice M., Sivak M. V. (1991) Spectroscopic diagnosis of colonic dysplasia. Photochemistry and Photobiology 53, 777-786.
11. Kapadia C. R., Cutruzzola F. W., O'Brien K. M., Stetz M. L., Enriquez R., Deckelbaum L. I. (1990) Laser-induced fluorescence spectroscopy of human colonic mucosa, Gastroenterology 99, 150-157.
12. Marchesini R., Brambilla M., Pignoli E., Bottiroli G., Croce A. C., Dal Fante M., Spinelli P., Di Palma S. (1992) Light-induced fluorescence spectroscopy of adenomas, adenocarcinomas and non-neoplastic mucosa in human colon, J Photochemistry and Photobiology 14(3), 219-30.
13. Cothren R. M., Richards-Kortum R. R., Rava R. P., Boyce G. A., Doxtader M., Blackman R., Ivanc T., Hayes G. B., Feld M. S., Petras R. E. (1990) Gastrointestinal tissue diagnosis by laser induced fluorescence spectroscopy at endoscopy. Gastrointestinal Endoscopy 36, 105–111.
14. Schomacker K. T., Frisoli J. K., Compton C. C., Flotte T. J., Richter J. M., Nishioka N. S., Deutsch T. F. (1992) Ultraviolet laser induced fluorescence of colonic tissue: basic biology and diagnostic potential. Lasers in Surgery and Medicine 12, 63-78.
15. Hung J., Lam S., LeRiche J. C., Palcic B. (1991) Autofluorescence of normal and malignant bronchial tissue. Lasers in Surgery and Medicine 11(2), 99-105.
16. Lam S., Hung J. Y. C., Kennedy S. M., Leriche J. C., Vedal R., Nelems B., Macaulay C. E., Palcic B. (1992) Detection of dysplasia and carcinoma in situ by ratio fluorimetry. Am Rev Dis 146, 1458-1461.
17. Lam S., Macaulay C., Palcic B. (1993) Detection and localization of early lung cancer by imaging techniques. Chest 103, 12s-14s.
18. Yuanlong Y., Yanming Y., Fuming L., Yufen L., Paozhong M. (1987) Characteristic autofluorescence for cancer diagnosis and its origin, Lasers in Surgery and Medicine 7, 528–532.
19. Montan S., Stromblad L. G. (1987) Spectral characterization of brain tumors utilizing laser-induced fluorescence. Lasers in Life Sciences 1(4), 275-285.
20. Liu C. H., Das B. B., Sha Glassman W. L., Tang G. C., Yoo K. M., Zhu H. R., Akins D. L., Lubicz S. S., Cleary J., Prudente R. (1992) Raman, fluorescence and time-resolved light scattering as optical diagnostic techniques to separate diseased and normal biomedical media. J Photochemistry and Photobiology 16(2), 187-209.
21. Glassman W. S. Liu C. H., Tang G. C., Lubicz S., Alfano R. R. (1992) Ultraviolet excited fluorescence spectra from non-malignant and malignant tissues of the gynecologic tract. Lasers in Life Sciences 5, 49-58.
22. Lohmann W., Mußmann J., Lohmann C., Kunzel W. (1989) Fluorescence of the cervix uteri as a marker for dysplasia and invasive carcinoma. European Journal of Obstetrics and Gynecology and Reproductive Biology 131, 249-253.
23. Mahadevan A., Mitchell M., Silva E., Thomsen S., Richards-Kortum R. R. (1993) Study of the fluorescence properties of normal and neoplastic human cervical tissue. Lasers in Surgery and Medicine 13, 647-655.
24. Braichotte D. R., Wagnieres G. A., Bays R., Monnier P., Van den Bergh H. E. (Jun. 1, 1995) Clinical pharmacokinetic studies of photofrin by fluorescence spectroscopy in the oral cavity, the esophagus and the bronchi. Cancer 75(11), 2768-78.

25. Gray M. J., Lipson R., Maeck J. V. S., Parker L., Romeyn D. (1967) Use of hematoporphyrin derivative in detection and management of cervical cancer. Am J Obst & Gynec, 766-770.
26. Kennedy J. C. Pottier R. H. (1992) Endogenous protoporphyrin IX, a clinical useful photosensitizer for photodynamic therapy. J Photochem Photobiol B:Biol 14, 275-292.
27. Loh C. S., MacRobert A. J., Bedwell J., Regula J., Krasner N., Bown S. G. (1993) Oral versus intravenous administration of 5-aminolaevulinic acid for photodynamic therapy. British Journal of Cancer 68(1), 41-51.
28. Dillon R. W., Goldstein M. (1984) *Multivariate Analysis: Methods and Applications*. John Wiley and Sons, New York.
29. Walpole R. E., Myers R. H. (1987) *Probability and Statistics for Engineers and Scientists*. Decker, New York.
30. Albert A., Harris E. K. (1987) *Multivariate Interpretation of Clinical Laboratory Data*. Marcel Dekker, New York.
31. Devore J. L. (1992) Probability and Statistics for Engineering and the Science. Brooks/Cole, Pacific Grove.

APPENDIX B

1. Wright T C, Kurman R J, and Ferenczy A in *Pathology of the Female Genital Tract* (eds. A. Blaustein), 156-177, Springer-Verlag, New York (1994).
2. Barron B A, Richart R M, "Statistical model of the natural history of cervical carcinoma: II. Estimates of the transition time from dysplasia to carcinoma in situ," JNCI 45: 1025-1030 (1970).
3. Burke L, Antonioli D A and Ducatman B S., *Colposcopy, Text and Atlas*, Appleton and Large, Norwalk Conn. (1991).
4. Mitchell M F, "Diagnosis and Treatment of Preinvasive Disease of the Female Lower Genital Tract" The Cancer Bulletin. 42: 71-76 (1990).
5. Reid R, Stanhope C R, Herschman B R, Crum C P, Agronow S J, "Genital warts and Cervical cancer," Am J Obstet Gynecol, IV: 815-823 (1984).
6. Reid R, Scalzi P, "Genital Warts and Cervical Cancer," Am J Obstet Gynecol, 153(6): 611-618 (1985).
7. Barrasso R, Coupez F, Ionesco M, DeBrux J, "Human Papilloma Viruses and Cervical Intraepithelial Neoplasia: The Role of Colposcopy," Gynecologic Oncology, 27: 197-207 (1987).
8. Alfano R R, Pradhan A and Tang C G, "Optical spectroscopic diagnosis of cancer in normal and breast tissues," J Optic Soc Am B, 6: 1015-1023 (1989).
9. Andersson E S, Johansson J, Svanberg K and Svanberg S, "Fluorescence imaging and point measurements of tissue: applications to the demarcation of malignant tumors and atherosclerotic lesions from normal tissue," Photochem Photobiol, 53: 807-14 (1991).
10. Richards-Kortum R R, Rava R P, Petras R E, Fitzmaurice M, Sivak M V and Feld M S, "Spectroscopic diagnosis of colonic dysplasia," Photochem Photobiol, 53: 777-786 (1991).
11. Rava R P, Richards-Kortum R R, Fitzmaurice M, Cothren R M, Petras R E, Sivak M and Feld M S, "Early detection of dysplasia in colon and urinary bladder tissue using laser-induced fluorescence", Optical methods for tumor treatment and early diagnosis: mechanisms and technique, SPIE 1426: 68-78 (1991).
12. Wong P T T, Wong R K, Caputo T A, Godwin T A and Rigas B, "Infrared spectroscopy of human cervical cells: Evidence of extensive structural changes during carcinogenesis," Proc Natl Acad Sci USA, 88: 10988-10992 (1991).
13. Alfano R R, Lui C H, Sha W L, Zhu H R, Akins D L, Cleary J, Prudente R and Cellmer E, "Human breast tissues studied by IR fourier transform Raman spectroscopy," Lasers in Life Sc, 4: 23-28 (1991).
14. Baraga J J, Feld M S and Rava R P, "Rapid near-infrared Raman spectroscopy of human tissue with a spectrograph and CCD detector." Appl. Spectr, 46: 187-190 (1992).
15. Schomacker K T, Frisoli J K, Compton C C, Flotte T J, Richter J M, Nishioka N S and Deutsch T F, "Ultraviolet laser-induced fluorescence of colonic tissue: Basic biology and diagnostic potential," Lasers in Surg Med, 12: 63-78 (1992).
16. Mahadevan A, Mitchell M F, Thomsen S, Silva E and Richards-Kortum R R, "A study of the fluorescence properties of normal and neoplastic human cervical tissue," Lasers Surg Med 13:647-655, (1993).
17. Ramanujam N, Mitchell M F, Mahadevan A, Thomsen S, Malpica A, Wright T C, Atkinson, N and Richards-Kortum; In Vivo Diagnosis of Cervical Intraepithelial Neoplasia Using 337 Excitation, PNAS 91:10193, 1994.
18. Ramanujam N, Mitchell M F, Mahadevan A, Thomsen S, Richards-Kortum R R, "Spectroscopic Diagnosis of Cervical Intraepithelial Neoplasia (CIN) in vivo Using Laser Induced Fluorescence Spectra at Multiple Excitation Wavelengths," Lasers Surg Med, (in press) (1996).
19. Brookner C K, Agrawal A, Trujillo E V, Mitchell M F and Richards-Kortum R R, "Relative Risk of UV-Fluorescence Spectroscopy and Endoscopy are comparable," 24th. Annual Meeting of the American Society for Photobiology, Photochem Photobiol Supp. (in press) (1996)

APPENDIX C: PRINCIPAL COMPONENTS

Principal Components of Full-Parameter Constituent Algorithm 1 which differentiates SILs from Normal Squamous Tissues. Results reported for calibration set:

| Legend | PC1 | PC3 | PC7 |
| --- | --- | --- | --- |
| 1 | 0.630 | −0.576 | 0.288 |
| 1 | 0.590 | −0.460 | 0.294 |
| 1 | 0.902 | −0.849 | −0.034 |
| 1 | 1.150 | −0.678 | −0.104 |
| 1 | −0.413 | −0.179 | −0.150 |
| 1 | −1.190 | −0.171 | −0.225 |
| 1 | 0.489 | −0.049 | −0.138 |
| 1 | 0.200 | −0.163 | −0.130 |
| 1 | −0.889 | −0.457 | −0.104 |
| 1 | 1.060 | −0.256 | −0.253 |
| 1 | 1.290 | −0.360 | −0.143 |
| 1 | −0.113 | −0.220 | −0.162 |
| 1 | 0.610 | −0.108 | −0.031 |
| 1 | −1.460 | −0.554 | −0.129 |
| 1 | 0.468 | −0.314 | −0.262 |
| 1 | 1.290 | −0.422 | −0.093 |
| 1 | 0.174 | −0.690 | −0.156 |
| 1 | 0.428 | −0.798 | −0.225 |
| 1 | 1.290 | −0.742 | −0.362 |
| 1 | 1.410 | −0.530 | −0.154 |
| 1 | 0.284 | −0.518 | −0.331 |
| 1 | 2.220 | −1.400 | −0.137 |
| 1 | 1.160 | −0.191 | −0.116 |
| 1 | 0.231 | −0.099 | −0.247 |
| 1 | 1.640 | −0.271 | −0.249 |
| 1 | 0.538 | −0.179 | −0.112 |
| 1 | −0.864 | 0.032 | 0.118 |
| 1 | 0.130 | −0.273 | −0.135 |

-continued

| Legend | PC1 | PC3 | PC7 |
|---|---|---|---|
| 1 | 0.152 | 0.029 | −0.010 |
| 1 | −0.978 | −0.702 | 0.095 |
| 1 | 0.635 | −0.120 | −0.079 |
| 1 | 1.660 | −0.683 | 0.002 |
| 1 | 0.934 | −0.401 | −0.150 |
| 1 | 0.692 | 0.015 | 0.144 |
| 1 | 0.018 | −0.363 | −0.094 |
| 1 | 0.401 | −0.085 | 0.071 |
| 1 | 0.187 | −0.146 | −0.043 |
| 1 | 0.132 | −0.142 | −0.175 |
| 1 | −0.593 | −1.260 | −0.103 |
| 1 | 1.140 | −0.565 | −0.353 |
| 1 | −0.349 | −0.423 | −0.147 |
| 1 | 0.717 | −0.084 | −0.373 |
| 1 | −0.128 | 0.065 | −0.141 |
| 1 | 1.570 | −0.223 | −0.171 |
| 1 | 1.500 | −0.661 | 0.034 |
| 1 | −1.210 | −0.545 | −0.126 |
| 1 | −0.009 | −0.104 | −0.175 |
| 1 | 0.553 | −0.169 | −0.117 |
| 1 | 0.247 | 0.010 | 0.125 |
| 1 | 0.502 | −0.182 | −0.039 |
| 1 | 1.620 | −0.247 | −0.210 |
| 1 | 1.350 | −0.546 | −0.311 |
| 1 | 0.940 | −0.690 | −0.236 |
| 1 | −0.258 | −0.276 | −0.033 |
| 1 | 0.369 | −0.385 | −0.347 |
| 1 | −0.185 | −0.227 | −0.011 |
| 1 | 0.602 | −0.642 | −0.358 |
| 1 | 0.890 | −0.963 | −0.797 |
| 1 | 0.864 | −0.463 | −0.326 |
| 1 | 1.090 | −0.548 | −0.336 |
| 1 | 0.003 | −0.152 | −0.122 |
| 1 | 0.087 | −0.153 | −0.161 |
| 1 | 0.182 | −0.315 | −0.114 |
| 1 | 0.666 | −0.437 | −0.389 |
| 1 | 1.470 | −0.874 | −0.148 |
| 1 | 0.055 | −0.492 | −0.119 |
| 1 | 1.200 | −0.728 | −0.438 |
| 1 | 1.430 | −0.442 | −0.285 |
| 1 | 0.991 | −0.580 | −0.409 |
| 1 | −0.454 | −0.600 | −0.174 |
| 1 | 0.659 | −0.931 | −0.505 |
| 1 | 0.225 | −0.266 | −0.351 |
| 1 | −1.110 | −0.519 | −0.184 |
| 1 | 1.060 | −0.390 | −0.392 |
| 1 | 1.650 | −0.584 | −0.146 |
| 1 | 0.026 | −0.048 | −0.140 |
| 1 | 0.112 | −0.466 | −0.318 |
| 1 | 1.710 | −0.561 | −0.275 |
| 1 | 1.630 | −0.918 | −0.353 |
| 1 | 0.624 | −0.490 | −0.182 |
| 1 | 0.051 | −0.922 | −0.164 |
| 1 | 0.197 | −0.004 | 0.003 |
| 1 | −0.814 | −0.239 | 0.066 |
| 1 | −1.510 | −0.399 | 0.135 |
| 1 | 0.403 | −0.161 | −0.281 |
| 1 | 0.043 | −0.967 | −0.132 |
| 1 | −1.940 | −1.510 | −0.130 |
| 1 | −0.980 | −0.603 | 0.107 |
| 1 | 0.468 | −0.327 | −0.141 |
| 1 | 0.174 | −1.140 | 0.033 |
| 1 | 1.220 | −0.413 | −0.340 |
| 1 | 1.110 | −0.272 | −0.135 |
| 1 | 0.096 | −0.299 | −0.195 |
| 1 | −1.190 | −0.083 | −0.324 |
| 2 | −0.642 | −0.115 | −0.100 |
| 2 | −0.421 | −0.074 | −0.194 |
| 2 | −0.170 | −0.293 | −0.344 |
| 2 | −1.680 | −1.210 | −0.469 |
| 2 | −0.828 | −0.215 | −0.426 |
| 2 | −0.327 | −0.096 | −0.287 |
| 2 | −1.690 | −0.350 | −0.090 |
| 2 | −1.330 | −0.709 | −0.367 |
| 2 | −0.481 | 0.261 | −0.238 |
| 2 | −0.623 | −0.126 | 0.095 |
| 2 | 0.035 | −0.325 | −0.319 |

-continued

| Legend | PC1 | PC3 | PC7 |
|---|---|---|---|
| 2 | −0.809 | −0.255 | −0.329 |
| 2 | −0.764 | −0.153 | −0.095 |
| 3 | −1.850 | −1.730 | 0.225 |
| 3 | −0.299 | −0.487 | 0.162 |
| 3 | −0.205 | −0.496 | −0.077 |
| 3 | 1.990 | −1.760 | −0.094 |
| 3 | −0.612 | −0.292 | −0.084 |
| 3 | −1.110 | −1.070 | −0.083 |
| 3 | −1.300 | −0.330 | −0.103 |
| 3 | −0.176 | −0.114 | 0.061 |
| 3 | −1.460 | −0.228 | −0.519 |
| 3 | −0.435 | −0.881 | −0.072 |
| 4 | −0.286 | −0.057 | 0.141 |
| 4 | −1.080 | −0.546 | −0.247 |
| 4 | −1.140 | −0.573 | −0.438 |
| 4 | −0.649 | −0.848 | 0.010 |
| 4 | −1.770 | −1.110 | −0.186 |
| 4 | −1.140 | −0.881 | −0.392 |
| 4 | 1.940 | −1.980 | 0.130 |
| 4 | −0.839 | −0.500 | −0.069 |
| 4 | −1.550 | −0.608 | −0.328 |
| 4 | −0.263 | −0.158 | −0.309 |
| 4 | 1.590 | −0.250 | −0.311 |
| 4 | −1.030 | −0.353 | −0.182 |
| 4 | −1.420 | −0.641 | −0.278 |
| 4 | −0.864 | −0.313 | −0.018 |
| 4 | −0.095 | −0.982 | 0.087 |
| 5 | 0.415 | −0.346 | −0.154 |
| 5 | −1.320 | −0.560 | −0.359 |
| 5 | 0.716 | −0.066 | 0.068 |
| 5 | −1.010 | −0.403 | −0.571 |
| 5 | −0.057 | −1.040 | −0.162 |
| 5 | 0.067 | −0.471 | −0.615 |
| 5 | 0.702 | −1.080 | −0.830 |
| 5 | 0.297 | −0.568 | 0.185 |
| 5 | −0.403 | −0.508 | −0.164 |
| 5 | 1.060 | −1.030 | −0.079 |
| 5 | −0.971 | −0.624 | −0.294 |
| 5 | −1.300 | −0.254 | −0.693 |
| 5 | −1.200 | −0.041 | −0.474 |
| 5 | −0.276 | 0.347 | −0.453 |
| 5 | 0.183 | −0.273 | −0.343 |
| 5 | −0.616 | −0.661 | −0.506 |
| 5 | −0.318 | −0.323 | −0.240 |
| 5 | −0.406 | −0.773 | −0.154 |
| 5 | −0.451 | −0.297 | −0.447 |
| 5 | 0.557 | −0.088 | −0.262 |
| 5 | −0.208 | −0.863 | −0.223 |
| 5 | −0.258 | 0.027 | −0.437 |
| 5 | −0.400 | −0.813 | −0.122 |
| 6 | −0.382 | −1.460 | 0.152 |
| 6 | −1.370 | −0.247 | −0.609 |
| 6 | −0.616 | −0.256 | −0.112 |
| 6 | 0.390 | −0.182 | −0.235 |
| 6 | −0.546 | −0.424 | −0.129 |
| 6 | 0.768 | −1.170 | −0.515 |
| 6 | −0.770 | −0.906 | −0.002 |
| 6 | −1.810 | −0.883 | −0.097 |
| 6 | 0.026 | −1.210 | −0.334 |
| 6 | −1.060 | −0.393 | −0.111 |
| 6 | −1.370 | −0.783 | −0.251 |
| 6 | 0.880 | −0.476 | −0.368 |
| 6 | −0.589 | −0.346 | −0.384 |
| 6 | 0.662 | −1.040 | −0.347 |
| 6 | −0.292 | −0.048 | −0.470 |
| 6 | −0.106 | −0.239 | −0.073 |
| 6 | −1.020 | −0.816 | −0.129 |
| 6 | −0.484 | −0.425 | −0.207 |
| 6 | −0.834 | −0.521 | −0.006 |
| 6 | −1.340 | −1.860 | −0.283 |
| 6 | −0.084 | −0.197 | −0.125 |
| 6 | −0.733 | −0.689 | −0.253 |
| 6 | −0.788 | −0.409 | −0.028 |
| 6 | −1.280 | −1.410 | −0.298 |
| 6 | −0.816 | −0.099 | −0.078 |
| 6 | −1.160 | −1.060 | 0.185 |
| 6 | −0.434 | −0.092 | −0.075 |

| Legend | PC1 | PC3 | PC7 |
|---|---|---|---|
| 6 | −0.139 | −1.300 | −0.195 |
| 6 | −0.768 | 0.120 | −0.300 |
| 6 | −0.951 | −0.441 | −0.219 |
| 6 | −0.392 | −0.307 | −0.727 |
| 6 | −0.015 | 0.071 | −0.171 |
| 6 | −1.430 | −0.619 | −0.127 |
| 6 | −1.110 | −1.070 | −0.104 |
| 6 | −1.360 | −0.504 | −0.699 |

Principal Components of Full-Parameter Constituent Algorithm 2 which differentiates SILs from Normal Columnar Tissues. Results reported for calibration set:

| L | PC1 | PC2 | PC4 | PC5 |
|---|---|---|---|---|
| 1 | 0.413 | −0.096 | −0.067 | −0.134 |
| 1 | 0.763 | −0.119 | −0.089 | 0.078 |
| 1 | 0.674 | 0.403 | −0.184 | 0.040 |
| 1 | 1.100 | 0.472 | −0.308 | 0.210 |
| 1 | 0.381 | 0.166 | 0.253 | −0.064 |
| 1 | −0.309 | −0.278 | −0.048 | −0.080 |
| 1 | 0.664 | −0.169 | −0.038 | −0.021 |
| 1 | −0.083 | −0.204 | 0.161 | −0.003 |
| 1 | −1.210 | −0.193 | −0.096 | −0.109 |
| 1 | 0.053 | −0.105 | 0.207 | 0.083 |
| 1 | 0.258 | −0.055 | 0.162 | −0.217 |
| 1 | 0.021 | −0.009 | −0.110 | 0.127 |
| 1 | 0.357 | 0.091 | 0.072 | 0.112 |
| 1 | −1.020 | −0.412 | −0.765 | −0.043 |
| 1 | −0.089 | −0.065 | −0.025 | 0.045 |
| 1 | 0.842 | 0.141 | −0.168 | −0.017 |
| 1 | 0.020 | 0.016 | 0.009 | 0.047 |
| 1 | 0.263 | 0.199 | 0.016 | 0.127 |
| 1 | 1.190 | 0.055 | −0.406 | −0.087 |
| 1 | 0.913 | 0.102 | −0.215 | −0.359 |
| 1 | 0.685 | 0.127 | 0.152 | 0.159 |
| 1 | 0.224 | −0.241 | 0.032 | 0.071 |
| 1 | 1.070 | 0.314 | −0.017 | −0.022 |
| 1 | 0.914 | −0.262 | 0.391 | −0.103 |
| 1 | 1.790 | −0.233 | −0.561 | −0.166 |
| 1 | 0.557 | 0.127 | −0.101 | 0.017 |
| 1 | −0.310 | −0.323 | −0.217 | −0.136 |
| 1 | 0.422 | 0.134 | 0.046 | 0.005 |
| 1 | 0.164 | −0.325 | 0.074 | 0.010 |
| 1 | −1.050 | 0.274 | −0.081 | −0.224 |
| 1 | 0.845 | −0.057 | −0.089 | 0.163 |
| 1 | 0.733 | −0.462 | −0.653 | −0.422 |
| 1 | 0.084 | −0.271 | 0.128 | 0.041 |
| 1 | 0.792 | −0.338 | 0.092 | −0.166 |
| 1 | 0.560 | 0.264 | 0.209 | −0.040 |
| 1 | 0.535 | 0.180 | 0.189 | 0.013 |
| 1 | 0.318 | 0.209 | 0.133 | 0.137 |
| 1 | 0.521 | 0.174 | 0.058 | 0.179 |
| 1 | 0.067 | 0.747 | −0.188 | 0.072 |
| 1 | 1.300 | −0.134 | −0.288 | −0.060 |
| 1 | −0.049 | 0.134 | 0.312 | −0.153 |
| 1 | 0.494 | 0.152 | 0.079 | 0.033 |
| 1 | 0.183 | −0.462 | 0.144 | 0.071 |
| 1 | 1.420 | 0.051 | −0.340 | −0.033 |
| 1 | 1.300 | −0.384 | −0.421 | −0.279 |
| 1 | −0.383 | 0.239 | −0.255 | −0.165 |
| 1 | 0.341 | −0.111 | −0.067 | 0.114 |
| 1 | 0.443 | 0.169 | 0.408 | 0.132 |
| 1 | 0.289 | −0.053 | 0.099 | 0.016 |
| 1 | 1.210 | −0.378 | 0.141 | 0.187 |
| 1 | 1.060 | 0.199 | −0.337 | −0.096 |
| 1 | 0.631 | −0.161 | −0.164 | −0.054 |
| 1 | 0.795 | 0.417 | −0.069 | 0.166 |
| 1 | 0.209 | 0.189 | 0.050 | 0.012 |
| 1 | 1.080 | −0.132 | 0.267 | −0.027 |
| 1 | 0.425 | 0.065 | 0.001 | 0.217 |
| 1 | 0.079 | 0.044 | −0.094 | 0.066 |
| 1 | 0.275 | 0.053 | −0.175 | −0.043 |
| 1 | 0.843 | 0.151 | −0.142 | 0.129 |
| 1 | 1.550 | 0.030 | −0.181 | 0.243 |
| 1 | 0.626 | −0.096 | 0.135 | 0.033 |
| 1 | 0.482 | −0.093 | 0.075 | 0.070 |
| 1 | 0.599 | −0.019 | 0.143 | 0.048 |
| 1 | 0.849 | 0.389 | −0.038 | 0.100 |
| 1 | 0.494 | −0.108 | −0.082 | −0.002 |
| 1 | 0.505 | −0.274 | 0.209 | −0.007 |
| 1 | 1.470 | −0.026 | −0.380 | −0.059 |
| 1 | 1.050 | 0.296 | −0.017 | −0.050 |
| 1 | 0.845 | −0.148 | −0.065 | −0.001 |
| 1 | −0.030 | 0.380 | 0.107 | −0.095 |
| 1 | 0.405 | 0.217 | −0.119 | 0.186 |
| 1 | 0.563 | −0.104 | 0.039 | 0.131 |
| 1 | −0.809 | −0.244 | −0.451 | 0.206 |
| 1 | 0.552 | 0.085 | −0.066 | 0.107 |
| 1 | 1.070 | −0.184 | −0.589 | −0.234 |
| 1 | 0.312 | −0.133 | −0.028 | 0.084 |
| 1 | 0.183 | 0.048 | 0.129 | 0.003 |
| 1 | 1.410 | 0.112 | −0.637 | −0.194 |
| 1 | 0.852 | −0.304 | −0.304 | −0.381 |
| 1 | 0.508 | −0.419 | 0.008 | −0.018 |
| 1 | 0.257 | 0.368 | −0.054 | 0.018 |
| 1 | 0.573 | 0.077 | −0.080 | 0.010 |
| 1 | −0.156 | −0.155 | −0.338 | 0.124 |
| 1 | −0.885 | −0.231 | −0.527 | −0.055 |
| 1 | 0.313 | −0.447 | 0.072 | 0.271 |
| 1 | 0.103 | 0.574 | 0.086 | 0.037 |
| 1 | 0.151 | 0.359 | 0.135 | −0.162 |
| 1 | 0.129 | 0.140 | 0.188 | −0.140 |
| 1 | −0.081 | −0.156 | 0.219 | 0.155 |
| 1 | 0.093 | 0.716 | −0.151 | −0.032 |
| 1 | 0.265 | −0.348 | 0.374 | 0.251 |
| 1 | 0.674 | −0.365 | −0.125 | −0.049 |
| 1 | 0.457 | −0.110 | 0.050 | 0.070 |
| 1 | 0.089 | −0.378 | −0.401 | 0.031 |
| 1 | −0.616 | −0.363 | −0.106 | 0.101 |
| 1 | −0.258 | −0.340 | −0.080 | −0.043 |
| 1 | −0.543 | −0.072 | −0.197 | −0.002 |
| 1 | −1.190 | 0.109 | −0.003 | 0.020 |
| 2 | −0.407 | −0.526 | 0.177 | −0.005 |
| 2 | −0.123 | −0.199 | 0.107 | 0.142 |
| 2 | −0.813 | −0.344 | −0.523 | 0.010 |
| 2 | −1.180 | −0.174 | 0.041 | −0.079 |
| 2 | −0.677 | −0.544 | −0.032 | −0.061 |
| 2 | −0.603 | −0.250 | −0.259 | 0.088 |
| 2 | −0.323 | 0.114 | 0.197 | 0.061 |
| 2 | −1.290 | −0.338 | 0.078 | −0.082 |
| 2 | −0.968 | −0.028 | 0.228 | 0.046 |
| 3 | −0.714 | 0.263 | −0.224 | 0.128 |
| 3 | −0.432 | −0.297 | 0.090 | −0.260 |
| 3 | −0.246 | 0.003 | 0.116 | 0.079 |
| 3 | −0.045 | 0.128 | 0.036 | 0.090 |
| 3 | −0.087 | 0.367 | 0.180 | 0.018 |
| 3 | −0.988 | 0.348 | 0.061 | −0.227 |
| 3 | −1.470 | −0.567 | −0.515 | −0.060 |
| 3 | −0.260 | −0.288 | 0.266 | −0.152 |
| 3 | −1.800 | −0.666 | −0.386 | −0.044 |
| 3 | −0.163 | 0.543 | 0.082 | −0.165 |
| 4 | −0.446 | −0.511 | 0.187 | −0.238 |
| 4 | −0.224 | 0.330 | 0.114 | 0.034 |
| 4 | −1.030 | 0.176 | −0.054 | 0.084 |
| 4 | −0.730 | 0.394 | 0.214 | −0.147 |
| 4 | −1.440 | 0.154 | −0.394 | −0.036 |
| 4 | −0.771 | 0.256 | 0.054 | 0.055 |
| 4 | −0.127 | 0.288 | −0.166 | 0.085 |
| 4 | −0.672 | 0.244 | 0.185 | −0.124 |
| 4 | −0.671 | 0.193 | −0.103 | 0.078 |
| 4 | 0.060 | −0.285 | 0.133 | 0.006 |
| 4 | 1.020 | 0.142 | −0.438 | −0.001 |
| 4 | −0.425 | −0.080 | −0.119 | 0.006 |
| 4 | −0.999 | 0.142 | −0.198 | 0.047 |
| 4 | 0.268 | −0.186 | 0.184 | −0.075 |
| 4 | −0.717 | 0.356 | −0.096 | 0.030 |
| 5 | 0.240 | −0.121 | 0.021 | 0.126 |
| 5 | −0.593 | 0.039 | −0.421 | 0.007 |

-continued

| L | PC1 | PC2 | PC4 | PC5 |
|---|---|---|---|---|
| 5 | 0.372 | −0.086 | −0.063 | −0.200 |
| 5 | −1.480 | −0.321 | −0.188 | 0.232 |
| 5 | −0.954 | 0.501 | 0.298 | 0.105 |
| 5 | −0.442 | −0.102 | 0.232 | 0.014 |
| 5 | −0.073 | 0.109 | 0.100 | 0.315 |
| 5 | 0.265 | 0.389 | 0.032 | −0.144 |
| 5 | −0.276 | 0.371 | 0.166 | −0.075 |
| 5 | −0.055 | 0.431 | −0.243 | −0.376 |
| 5 | −0.451 | −0.360 | 0.221 | −0.354 |
| 5 | −1.040 | −0.285 | −0.166 | 0.302 |
| 5 | −0.642 | −0.475 | 0.058 | 0.085 |
| 5 | −0.755 | −0.254 | 0.592 | 0.010 |
| 5 | −0.490 | −0.434 | 0.179 | 0.045 |
| 5 | 0.063 | −0.043 | 0.092 | 0.089 |
| 5 | −0.327 | −0.135 | 0.005 | −0.019 |
| 5 | 0.043 | 0.292 | 0.345 | −0.252 |
| 5 | −0.109 | −0.355 | 0.106 | 0.298 |
| 5 | 1.010 | −0.267 | −0.130 | 0.085 |
| 5 | −0.457 | 0.147 | 0.117 | −0.196 |
| 5 | 0.130 | 0.181 | 0.331 | 0.119 |
| 5 | −0.551 | 0.157 | 0.103 | −0.121 |
| 6 | −0.668 | 1.010 | 0.133 | 0.016 |
| 6 | −0.601 | −0.219 | −0.273 | 0.268 |
| 6 | −0.488 | −0.070 | −0.079 | −0.058 |
| 6 | 0.045 | 0.046 | 0.046 | −0.072 |
| 6 | −0.278 | 0.004 | −0.230 | −0.055 |
| 6 | −0.156 | 0.620 | 0.129 | 0.208 |
| 6 | −0.553 | 0.533 | 0.069 | −0.216 |
| 6 | −1.190 | −0.493 | −0.774 | 0.083 |
| 6 | −0.735 | 0.701 | 0.163 | −0.019 |
| 6 | −0.619 | 0.066 | −0.068 | −0.078 |
| 6 | −0.926 | 0.028 | 0.101 | −0.023 |
| 6 | 0.361 | 0.116 | −0.041 | −0.064 |
| 6 | −0.339 | 0.180 | 0.181 | −0.054 |
| 6 | 0.488 | 0.172 | −0.086 | 0.000 |
| 6 | −0.271 | −0.517 | 0.171 | 0.199 |
| 6 | 0.269 | −0.207 | 0.095 | −0.099 |
| 6 | −0.136 | 0.233 | 0.077 | −0.103 |
| 6 | 0.066 | −0.330 | 0.455 | −0.310 |
| 6 | −0.660 | 0.283 | 0.093 | −0.132 |
| 6 | −1.400 | 1.460 | −0.371 | 0.665 |
| 6 | 0.296 | 0.131 | −0.031 | 0.090 |
| 6 | −0.235 | −0.047 | −0.327 | 0.147 |
| 6 | −0.529 | −0.019 | 0.127 | −0.117 |
| 6 | −1.510 | 0.623 | 0.091 | 0.344 |
| 6 | 0.064 | −0.064 | −0.030 | −0.076 |
| 6 | −0.373 | 1.040 | −0.099 | −0.280 |
| 6 | −0.075 | −0.130 | 0.077 | −0.130 |
| 6 | 0.479 | 0.206 | −0.047 | 0.080 |
| 6 | −0.092 | −0.433 | 0.087 | 0.045 |
| 6 | −0.364 | 0.010 | −0.046 | 0.126 |
| 6 | −1.220 | −0.321 | 0.804 | 0.698 |
| 6 | −0.196 | −0.155 | 0.300 | 0.123 |
| 6 | −0.347 | −0.111 | −0.024 | −0.097 |
| 6 | −0.479 | −0.206 | 0.047 | −0.080 |
| 6 | −0.078 | 0.406 | 0.047 | 0.227 |

Principal Components of Full-Parameter Constituent Algorithm 3 which differentiates HG SILs from LG SILs. Results reported for calibration set.

| L | PC1 | PC3 | PC6 | PC8 |
|---|---|---|---|---|
| 1 | 0.630 | −0.576 | −0.733 | −0.127 |
| 1 | 0.590 | −0.460 | −0.800 | −0.113 |
| 1 | 0.902 | −0.849 | −0.480 | −1.080 |
| 1 | 1.150 | −0.678 | −1.070 | −0.601 |
| 1 | −0.413 | −0.179 | −0.777 | −0.231 |
| 1 | −1.190 | −0.171 | −0.859 | −0.273 |
| 1 | 0.489 | −0.049 | −0.676 | −0.292 |
| 1 | 0.200 | −0.163 | −0.819 | −0.476 |
| 1 | −0.889 | −0.457 | −0.883 | −0.420 |

-continued

| L | PC1 | PC3 | PC6 | PC8 |
|---|---|---|---|---|
| 1 | 1.060 | −0.256 | −0.807 | −0.268 |
| 1 | 1.290 | −0.360 | −0.860 | −0.321 |
| 1 | −0.113 | −0.220 | −0.879 | −0.511 |
| 1 | 0.610 | −0.108 | −0.927 | −0.446 |
| 1 | −1.460 | −0.554 | −1.050 | −0.356 |
| 1 | 0.468 | −0.314 | −1.010 | −0.557 |
| 1 | 1.290 | −0.422 | −0.800 | −0.340 |
| 1 | 0.174 | −0.690 | −0.966 | −0.505 |
| 1 | 0.428 | −0.798 | −0.975 | −0.517 |
| 1 | 1.290 | −0.742 | −0.809 | −0.214 |
| 1 | 1.410 | −0.530 | −0.942 | −0.253 |
| 1 | 0.284 | −0.518 | −0.950 | −0.454 |
| 1 | 2.220 | −1.400 | −0.802 | −0.765 |
| 1 | 1.160 | −0.191 | −0.919 | −0.652 |
| 1 | 0.231 | −0.099 | −0.907 | −0.476 |
| 1 | 1.640 | −0.271 | −0.678 | −0.411 |
| 1 | 0.538 | −0.179 | −0.942 | −0.693 |
| 1 | −0.864 | 0.032 | −0.905 | −0.388 |
| 1 | 0.130 | −0.273 | −1.110 | −0.464 |
| 1 | 0.152 | 0.029 | −0.958 | −0.725 |
| 1 | −0.978 | −0.702 | −1.240 | −0.666 |
| 1 | 0.635 | −0.120 | −0.823 | −0.554 |
| 1 | 1.660 | −0.683 | −0.848 | −0.439 |
| 1 | 0.934 | −0.401 | −0.956 | −0.532 |
| 1 | 0.692 | 0.015 | −0.850 | −0.492 |
| 1 | 0.018 | −0.363 | −0.938 | −0.491 |
| 1 | 0.401 | −0.085 | −0.984 | −0.561 |
| 1 | 0.187 | −0.146 | −1.030 | −0.532 |
| 1 | 0.132 | −0.142 | −1.050 | −0.625 |
| 1 | −0.593 | −1.260 | −1.070 | −0.557 |
| 1 | 1.140 | −0.565 | −0.758 | −0.378 |
| 1 | −0.349 | −0.423 | −0.766 | −0.458 |
| 1 | 0.717 | −0.084 | −0.918 | −0.529 |
| 1 | −0.128 | 0.065 | −0.820 | −0.553 |
| 1 | 1.570 | −0.223 | −0.801 | −0.474 |
| 1 | 1.500 | −0.661 | −0.754 | −0.278 |
| 1 | −1.210 | −0.545 | −0.776 | −0.353 |
| 1 | −0.009 | −0.104 | −0.816 | −0.518 |
| 1 | 0.553 | −0.169 | −0.939 | −0.618 |
| 1 | 0.247 | 0.010 | −0.968 | −0.611 |
| 1 | 0.502 | −0.182 | −1.010 | −0.522 |
| 1 | 1.620 | −0.247 | −0.887 | −0.497 |
| 1 | 1.350 | −0.546 | −0.791 | −0.528 |
| 1 | 0.940 | −0.690 | −1.040 | −0.574 |
| 1 | −0.258 | −0.276 | −1.020 | −0.645 |
| 1 | 0.369 | −0.385 | −0.836 | −0.745 |
| 1 | −0.185 | −0.227 | −1.060 | −0.527 |
| 1 | 0.602 | −0.642 | −0.865 | −0.293 |
| 1 | 0.890 | −0.963 | −1.510 | −0.591 |
| 1 | 0.864 | −0.463 | −1.050 | −0.461 |
| 1 | 1.090 | −0.548 | −0.932 | −0.358 |
| 1 | 0.003 | −0.152 | −0.927 | −0.361 |
| 1 | 0.087 | −0.153 | −0.861 | −0.595 |
| 1 | 0.182 | −0.315 | −0.965 | −0.411 |
| 1 | 0.666 | −0.437 | −0.994 | −0.330 |
| 1 | 1.470 | −0.874 | −0.725 | −0.089 |
| 1 | 0.055 | −0.492 | −1.000 | −0.383 |
| 1 | 1.200 | −0.728 | −0.907 | −0.348 |
| 1 | 1.430 | −0.442 | −0.902 | −0.446 |
| 1 | 0.991 | −0.580 | −0.889 | −0.315 |
| 1 | −0.454 | −0.600 | −1.040 | −0.611 |
| 1 | 0.659 | −0.931 | −0.672 | −0.599 |
| 1 | 0.225 | −0.266 | −0.918 | −0.373 |
| 1 | −1.110 | −0.519 | −0.988 | −0.279 |
| 1 | 1.060 | −0.390 | −0.991 | −0.485 |
| 1 | 1.650 | −0.584 | −0.973 | −0.558 |
| 1 | 0.026 | −0.048 | −0.880 | −0.406 |
| 1 | 0.112 | −0.466 | −0.980 | −0.447 |
| 1 | 1.710 | −0.561 | −0.755 | −0.408 |
| 1 | 1.630 | −0.918 | −1.230 | −0.470 |
| 1 | 0.624 | −0.490 | −0.944 | −0.599 |
| 1 | 0.051 | −0.922 | −0.990 | −0.450 |
| 1 | 0.197 | −0.004 | −0.908 | −0.510 |
| 1 | −0.814 | −0.239 | −0.815 | −0.289 |
| 1 | −1.510 | −0.399 | −0.932 | −0.328 |
| 1 | 0.403 | −0.161 | −1.000 | −0.616 |
| 1 | 0.043 | −0.967 | −0.972 | −0.665 |

-continued

| L | PC1 | PC3 | PC6 | PC8 |
|---|---|---|---|---|
| 1 | -1.940 | -1.510 | -0.728 | -0.651 |
| 1 | -0.980 | -0.603 | -0.988 | -0.440 |
| 1 | 0.468 | -0.327 | -0.855 | -0.442 |
| 1 | 0.174 | -1.140 | -0.843 | -0.627 |
| 1 | 1.220 | -0.413 | -0.873 | -0.518 |
| 1 | 1.110 | -0.272 | -0.801 | -0.410 |
| 1 | 0.096 | -0.299 | -0.956 | -0.524 |
| 1 | -1.190 | -0.083 | -0.928 | -0.501 |
| 1 | -0.642 | -0.115 | -0.891 | -0.659 |
| 1 | -0.421 | -0.074 | -0.746 | -0.336 |
| 1 | -0.170 | -0.293 | -0.999 | -0.479 |
| 1 | -1.680 | -1.210 | -0.052 | -0.787 |
| 2 | -0.828 | -0.215 | -0.730 | -0.495 |
| 2 | -0.327 | -0.096 | -0.893 | -0.541 |
| 2 | -1.690 | -0.350 | -1.570 | 0.044 |
| 2 | -1.330 | -0.709 | -0.869 | -0.413 |
| 2 | -0.481 | 0.261 | -0.864 | -0.420 |
| 2 | -0.623 | -0.126 | -0.913 | -0.550 |
| 2 | 0.035 | -0.325 | -0.990 | -0.496 |
| 2 | -0.809 | -0.255 | -0.765 | -0.478 |
| 2 | -0.764 | -0.153 | -0.959 | -0.573 |
| 3 | -1.850 | -1.730 | -1.060 | -1.300 |
| 3 | -0.299 | -0.487 | -0.796 | -0.542 |
| 3 | -0.205 | -0.496 | -0.880 | -0.481 |
| 3 | 1.990 | -1.760 | -0.752 | -0.609 |
| 3 | -0.612 | -0.292 | -1.150 | -0.562 |
| 3 | -1.110 | -1.070 | -0.996 | -0.604 |
| 3 | -1.300 | -0.330 | -1.240 | -0.852 |
| 3 | -0.176 | -0.114 | -0.995 | -0.616 |
| 3 | -1.460 | -0.228 | -1.110 | -0.520 |
| 3 | -0.435 | -0.881 | -1.090 | -0.533 |
| 4 | -0.286 | -0.057 | -0.928 | -0.711 |
| 4 | -1.080 | -0.546 | -0.964 | -0.488 |
| 4 | -1.140 | -0.573 | -1.030 | -0.261 |
| 4 | -0.649 | -0.848 | -1.060 | -0.411 |
| 4 | -1.770 | -1.110 | -0.822 | -0.476 |
| 4 | -1.140 | -0.881 | -0.894 | -0.408 |
| 4 | 1.940 | -1.980 | -0.856 | -0.521 |
| 4 | -0.839 | -0.500 | -0.955 | -0.571 |
| 4 | -1.550 | -0.608 | -1.180 | -0.232 |
| 4 | -0.263 | -0.158 | -0.744 | -0.297 |
| 4 | 1.590 | -0.250 | -0.869 | -0.474 |
| 4 | -1.030 | -0.353 | -0.739 | -0.284 |
| 4 | -1.420 | -0.641 | -1.030 | -0.377 |
| 4 | -0.864 | -0.313 | -1.090 | -0.495 |
| 4 | -0.095 | -0.982 | -1.050 | -0.451 |
| 5 | 0.415 | -0.346 | -0.649 | -0.850 |
| 5 | -1.320 | -0.560 | -0.940 | -0.282 |
| 5 | 0.716 | -0.066 | -0.872 | -0.464 |
| 5 | -1.010 | -0.403 | -1.070 | -0.492 |
| 5 | -0.057 | -1.040 | -1.090 | -0.594 |
| 5 | 0.067 | -0.471 | -1.020 | -0.277 |
| 5 | 0.702 | -1.080 | -1.610 | -0.545 |
| 5 | 0.297 | -0.568 | -1.020 | -0.626 |
| 5 | -0.403 | -0.508 | -0.966 | -0.386 |
| 5 | 1.060 | -1.030 | -1.030 | -0.227 |
| 5 | -0.971 | -0.624 | -0.731 | -0.284 |
| 5 | -1.300 | -0.254 | -1.590 | -0.970 |
| 5 | -1.200 | -0.041 | -1.020 | -0.759 |
| 5 | -0.276 | 0.347 | -0.762 | -0.781 |
| 5 | 0.183 | -0.273 | -0.794 | -0.676 |
| 5 | -0.616 | -0.661 | -0.989 | -0.818 |
| 5 | -0.318 | -0.323 | -1.130 | -0.570 |
| 5 | -0.406 | -0.773 | -0.981 | -0.286 |
| 5 | -0.451 | -0.297 | -1.050 | -0.430 |
| 5 | 0.557 | -0.088 | -0.927 | -0.665 |
| 5 | -0.208 | -0.863 | -0.967 | -0.484 |
| 5 | -0.258 | 0.027 | -0.908 | -0.372 |
| 5 | -0.400 | -0.813 | -0.967 | -0.583 |
| 6 | -0.382 | -1.460 | -0.829 | -0.076 |
| 6 | -1.370 | -0.247 | -0.950 | -0.132 |
| 6 | -0.616 | -0.256 | -0.867 | -0.432 |
| 6 | 0.390 | -0.182 | -0.796 | -0.355 |
| 6 | -0.546 | -0.424 | -1.200 | -0.654 |
| 6 | 0.768 | -1.170 | -1.140 | -0.381 |
| 6 | -0.770 | -0.906 | -0.862 | -0.358 |
| 6 | -1.810 | -0.883 | -1.110 | -0.225 |
| 6 | 0.026 | -1.210 | -0.959 | -0.584 |
| 6 | -1.060 | -0.393 | -0.945 | -0.578 |
| 6 | -1.370 | -0.783 | -0.837 | -0.544 |
| 6 | 0.880 | -0.476 | -0.936 | -0.372 |
| 6 | -0.589 | -0.346 | -1.040 | -0.451 |
| 6 | 0.662 | -1.040 | -0.993 | -0.515 |
| 6 | -0.292 | -0.048 | -0.985 | -0.457 |
| 6 | -0.106 | -0.239 | -0.796 | -0.440 |
| 6 | -1.020 | -0.816 | -0.936 | -0.213 |
| 6 | -0.484 | -0.425 | -0.757 | -0.417 |
| 6 | -0.834 | -0.521 | -1.000 | -0.586 |
| 6 | -1.340 | -1.860 | -0.571 | -0.439 |
| 6 | -0.084 | -0.197 | -1.010 | -0.541 |
| 6 | -0.733 | -0.689 | -1.050 | -0.421 |
| 6 | -0.788 | -0.409 | -0.958 | -0.358 |
| 6 | -1.280 | -1.410 | -1.210 | -0.353 |
| 6 | -0.816 | -0.099 | -0.780 | -0.370 |
| 6 | -1.160 | -1.060 | -1.060 | -0.531 |
| 6 | -0.434 | -0.092 | -0.785 | -0.477 |
| 6 | -0.139 | -1.300 | -0.827 | -0.555 |
| 6 | -0.768 | 0.120 | -0.628 | -0.568 |
| 6 | -0.951 | -0.441 | -1.110 | -0.085 |
| 6 | -0.392 | -0.307 | -0.411 | -0.213 |
| 6 | -0.015 | 0.071 | -0.829 | -0.420 |
| 6 | -1.430 | -0.619 | -1.150 | -0.767 |
| 6 | -1.110 | -1.070 | -0.843 | -0.648 |
| 6 | -1.360 | -0.504 | -0.251 | -0.591 |
|   | -1.940 | -1.980 | -1.610 | -1.300 |

Principal Components of Reduced-Parameter Constituent Algorithm 1 which differentiates SILs from Normal Squamous Tissues. Results reported for calibration set.

| L | PC1 | PC2 | PC3 | PC4 | PC6 |
|---|---|---|---|---|---|
| 1 | 0.748 | -1.370 | 0.432 | -0.128 | -0.580 |
| 1 | 0.747 | -1.380 | 0.432 | -0.128 | -0.602 |
| 1 | 0.857 | -1.490 | 0.644 | -0.281 | -0.410 |
| 1 | 0.937 | -1.410 | 0.678 | -0.111 | -0.615 |
| 1 | 0.513 | -1.310 | 0.791 | -0.172 | -0.572 |
| 1 | 0.150 | -1.190 | 0.803 | -0.165 | -0.552 |
| 1 | 0.828 | -1.280 | 0.772 | -0.179 | -0.553 |
| 1 | 0.768 | -1.370 | 0.870 | -0.187 | -0.568 |
| 1 | 0.334 | -1.350 | 0.819 | -0.183 | -0.606 |
| 1 | 0.929 | -1.340 | 0.657 | -0.183 | -0.589 |
| 1 | 0.989 | -1.300 | 0.676 | -0.143 | -0.577 |
| 1 | 0.584 | -1.320 | 0.789 | -0.170 | -0.590 |
| 1 | 0.807 | -1.300 | 0.716 | -0.165 | -0.584 |
| 1 | -0.221 | -1.050 | 0.509 | -0.117 | -0.515 |
| 1 | 0.729 | -1.360 | 0.699 | -0.146 | -0.575 |
| 1 | 0.969 | -1.320 | 0.646 | -0.158 | -0.575 |
| 1 | 0.701 | -1.450 | 0.734 | -0.056 | -0.563 |
| 1 | 0.773 | -1.490 | 0.722 | -0.071 | -0.577 |
| 1 | 0.878 | -1.270 | 0.697 | -0.173 | -0.622 |
| 1 | 0.766 | -1.120 | 0.535 | -0.141 | -0.550 |
| 1 | 0.645 | -1.370 | 0.690 | -0.125 | -0.534 |
| 1 | 0.741 | -0.828 | 0.386 | -0.060 | -0.589 |
| 1 | 0.972 | -1.270 | 0.761 | -0.146 | -0.541 |
| 1 | 0.680 | -1.260 | 0.774 | -0.179 | -0.578 |
| 1 | 0.993 | -1.100 | 0.718 | -0.213 | -0.566 |
| 1 | 0.848 | -1.340 | 0.819 | -0.130 | -0.508 |
| 1 | 0.316 | -1.180 | 0.794 | -0.125 | -0.533 |
| 1 | 0.579 | -1.310 | 0.730 | -0.077 | -0.535 |
| 1 | 0.738 | -1.250 | 0.851 | -0.083 | -0.509 |
| 1 | 0.303 | -1.370 | 0.816 | 0.046 | -0.575 |
| 1 | 0.862 | -1.290 | 0.736 | -0.124 | -0.524 |
| 1 | 0.975 | -1.140 | 0.635 | -0.116 | -0.564 |
| 1 | 0.935 | -1.330 | 0.763 | -0.065 | -0.530 |
| 1 | 0.897 | -1.270 | 0.703 | -0.111 | -0.528 |
| 1 | 0.697 | -1.380 | 0.821 | -0.085 | -0.551 |
| 1 | 0.789 | -1.300 | 0.724 | -0.075 | -0.523 |
| 1 | 0.701 | -1.320 | 0.700 | -0.073 | -0.536 |

-continued

| L | PC1 | PC2 | PC3 | PC4 | PC6 |
|---|---|---|---|---|---|
| 1 | 0.676 | −1.340 | 0.765 | −0.110 | −0.541 |
| 1 | 0.433 | −1.540 | 0.666 | 0.109 | −0.541 |
| 1 | 0.910 | −1.340 | 0.776 | −0.315 | −0.621 |
| 1 | 0.557 | −1.370 | 0.781 | −0.099 | −0.481 |
| 1 | 0.923 | −1.300 | 0.873 | −0.105 | −0.514 |
| 1 | 0.628 | −1.210 | 0.845 | −0.101 | −0.473 |
| 1 | 1.060 | −1.170 | 0.705 | −0.141 | −0.543 |
| 1 | 0.897 | −1.140 | 0.598 | −0.167 | −0.600 |
| 1 | 0.143 | −1.310 | 0.845 | −0.269 | −0.687 |
| 1 | 0.635 | −1.310 | 0.807 | −0.185 | −0.568 |
| 1 | 0.867 | −1.360 | 0.763 | −0.069 | −0.531 |
| 1 | 0.771 | −1.250 | 0.769 | −0.051 | −0.472 |
| 1 | 0.763 | −1.330 | 0.681 | −0.114 | −0.552 |
| 1 | 1.060 | −1.170 | 0.697 | −0.135 | −0.522 |
| 1 | 1.040 | −1.330 | 0.754 | −0.143 | −0.568 |
| 1 | 0.898 | −1.430 | 0.724 | −0.096 | −0.574 |
| 1 | 0.558 | −1.330 | 0.789 | −0.059 | −0.487 |
| 1 | 0.668 | −1.340 | 0.771 | −0.192 | −0.536 |
| 1 | 0.582 | −1.320 | 0.713 | 0.020 | −0.537 |
| 1 | 0.771 | −1.440 | 0.656 | −0.164 | −0.597 |
| 1 | 0.635 | −1.280 | 0.691 | −0.059 | −0.559 |
| 1 | 0.854 | −1.400 | 0.686 | −0.126 | −0.585 |
| 1 | 0.876 | −1.360 | 0.640 | −0.142 | −0.599 |
| 1 | 0.679 | −1.260 | 0.784 | 0.006 | −0.511 |
| 1 | 0.690 | −1.320 | 0.834 | −0.146 | −0.491 |
| 1 | 0.711 | −1.340 | 0.753 | −0.096 | −0.524 |
| 1 | 0.694 | −1.300 | 0.677 | −0.099 | −0.546 |
| 1 | 0.812 | −1.160 | 0.545 | −0.188 | −0.640 |
| 1 | 0.671 | −1.390 | 0.754 | −0.054 | −0.556 |
| 1 | 0.869 | −1.300 | 0.844 | −0.337 | −0.660 |
| 1 | 1.000 | −1.300 | 0.724 | −0.160 | −0.568 |
| 1 | 0.860 | −1.350 | 0.693 | −0.166 | −0.576 |
| 1 | 0.476 | −1.340 | 0.738 | 0.152 | −0.500 |
| 1 | 0.804 | −1.500 | 0.728 | −0.141 | −0.576 |
| 1 | 0.729 | −1.330 | 0.790 | −0.069 | −0.509 |
| 1 | 0.167 | −1.360 | 0.671 | −0.096 | −0.558 |
| 1 | 0.929 | −1.330 | 0.733 | −0.087 | −0.542 |
| 1 | 0.933 | −1.110 | 0.651 | −0.113 | −0.562 |
| 1 | 0.581 | −1.270 | 0.710 | −0.182 | −0.577 |
| 1 | 0.655 | −1.370 | 0.765 | −0.077 | −0.570 |
| 1 | 0.921 | −1.070 | 0.652 | −0.187 | −0.548 |
| 1 | 0.753 | −1.010 | 0.620 | −0.111 | −0.522 |
| 1 | 0.730 | −1.320 | 0.687 | −0.124 | −0.546 |
| 1 | 0.615 | −1.430 | 0.692 | −0.014 | −0.552 |
| 1 | 0.640 | −1.150 | 0.655 | −0.012 | −0.445 |
| 1 | 0.155 | −1.200 | 0.583 | −0.225 | −0.573 |
| 1 | −0.120 | −1.140 | 0.592 | −0.191 | −0.573 |
| 1 | 0.694 | −1.280 | 0.727 | −0.123 | −0.544 |
| 1 | 0.556 | −1.460 | 0.645 | −0.043 | −0.506 |
| 1 | −0.245 | −1.390 | 0.594 | −0.170 | −0.560 |
| 1 | 0.126 | −1.310 | 0.639 | −0.083 | −0.486 |
| 1 | 0.726 | −1.330 | 0.668 | −0.131 | −0.559 |
| 1 | 0.633 | −1.490 | 0.669 | −0.076 | −0.568 |
| 1 | 0.879 | −1.260 | 0.732 | −0.224 | −0.559 |
| 1 | 0.898 | −1.260 | 0.606 | −0.183 | −0.567 |
| 1 | 0.641 | −1.290 | 0.788 | −0.113 | −0.552 |
| 1 | −0.132 | −0.941 | 0.564 | −0.168 | −0.439 |
| 2 | 0.407 | −1.260 | 0.803 | −0.116 | −0.546 |
| 2 | 0.494 | −1.260 | 0.841 | −0.228 | −0.586 |
| 2 | 0.474 | −1.350 | 0.762 | −0.273 | −0.653 |
| 2 | 0.009 | −1.650 | 0.734 | −0.455 | −0.352 |
| 2 | 0.254 | −1.280 | 0.903 | −0.364 | −0.616 |
| 2 | 0.496 | −1.250 | 0.868 | −0.143 | −0.534 |
| 2 | −0.170 | −1.120 | 0.642 | 0.053 | −0.728 |
| 2 | 0.179 | −1.460 | 0.977 | −0.370 | −0.650 |
| 2 | 0.490 | −1.170 | 0.905 | −0.200 | −0.513 |
| 2 | 0.383 | −1.240 | 0.739 | −0.193 | −0.555 |
| 2 | 0.585 | −1.320 | 0.819 | −0.163 | −0.569 |
| 2 | 0.376 | −1.310 | 0.890 | −0.186 | −0.557 |
| 2 | 0.403 | −1.230 | 0.785 | −0.018 | −0.471 |
| 3 | −0.201 | −1.510 | 0.489 | −0.004 | −0.466 |
| 3 | 0.590 | −1.380 | 0.739 | −0.071 | −0.536 |
| 3 | 0.593 | −1.380 | 0.751 | −0.082 | −0.539 |
| 3 | 0.658 | −0.962 | 0.373 | −0.144 | −0.665 |
| 3 | 0.520 | −1.370 | 0.890 | −0.003 | −0.508 |
| 3 | 0.279 | −1.550 | 0.839 | −0.186 | −0.608 |
| 3 | −0.062 | −1.080 | 0.662 | −0.004 | −0.488 |

| L | PC1 | PC2 | PC3 | PC4 | PC6 |
|---|---|---|---|---|---|
| 3 | 0.657 | −1.310 | 0.849 | −0.085 | −0.530 |
| 3 | −0.090 | −1.100 | 0.788 | −0.163 | −0.527 |
| 3 | 0.533 | −1.490 | 0.769 | 0.040 | −0.530 |
| 4 | 0.549 | −1.290 | 0.801 | −0.188 | −0.538 |
| 4 | 0.270 | −1.390 | 0.864 | −0.182 | −0.633 |
| 4 | 0.241 | −1.450 | 0.882 | −0.166 | −0.635 |
| 4 | 0.455 | −1.470 | 0.764 | −0.005 | −0.613 |
| 4 | −0.119 | −1.380 | 0.636 | −0.180 | −0.601 |
| 4 | 0.162 | −1.460 | 0.753 | −0.179 | −0.605 |
| 4 | 0.610 | −1.010 | 0.285 | −0.158 | −0.690 |
| 4 | 0.394 | −1.360 | 0.826 | −0.039 | −0.551 |
| 4 | −0.007 | −1.290 | 0.706 | 0.034 | −0.564 |
| 4 | 0.494 | −1.260 | 0.818 | −0.195 | −0.556 |
| 4 | 0.999 | −1.150 | 0.673 | −0.154 | −0.518 |
| 4 | 0.243 | −1.310 | 0.784 | −0.140 | −0.667 |
| 4 | 0.102 | −1.290 | 0.656 | 0.177 | −0.501 |
| 4 | 0.176 | −1.190 | 0.687 | −0.058 | −0.504 |
| 4 | 0.444 | −1.430 | 0.540 | −0.059 | −0.606 |
| 5 | 0.731 | −1.380 | 0.721 | −0.247 | −0.437 |
| 5 | 0.004 | −1.260 | 0.744 | −0.204 | −0.625 |
| 5 | 0.864 | −1.330 | 0.667 | −0.177 | −0.579 |
| 5 | −0.023 | −1.140 | 0.653 | −0.274 | −0.600 |
| 5 | 0.671 | −1.540 | 0.729 | 0.059 | −0.539 |
| 5 | 0.622 | −1.400 | 0.823 | −0.079 | −0.534 |
| 5 | 0.495 | −1.230 | 0.677 | −0.069 | −0.513 |
| 5 | 0.759 | −1.440 | 0.780 | −0.097 | −0.608 |
| 5 | 0.581 | −1.450 | 0.835 | −0.080 | −0.588 |
| 5 | 0.782 | −1.360 | 0.539 | −0.088 | −0.662 |
| 5 | 0.242 | −1.380 | 0.812 | −0.253 | −0.647 |
| 5 | −0.019 | −1.210 | 0.932 | −0.074 | −0.532 |
| 5 | 0.194 | −1.230 | 0.990 | −0.170 | −0.529 |
| 5 | 0.682 | −1.160 | 1.080 | −0.110 | −0.391 |
| 5 | 0.750 | −1.330 | 0.848 | −0.108 | −0.485 |
| 5 | 0.274 | −1.370 | 0.748 | −0.135 | −0.538 |
| 5 | 0.510 | −1.360 | 0.785 | −0.090 | −0.560 |
| 5 | 0.533 | −1.440 | 0.781 | −0.053 | −0.590 |
| 5 | 0.468 | −1.350 | 0.903 | −0.216 | −0.532 |
| 5 | 0.747 | −1.160 | 0.733 | 0.027 | −0.441 |
| 5 | 0.593 | −1.450 | 0.746 | 0.072 | −0.555 |
| 5 | 0.570 | −1.230 | 0.841 | −0.065 | −0.504 |
| 5 | 0.451 | −1.430 | 0.709 | −0.052 | −0.607 |
| 6 | 0.499 | −1.670 | 0.458 | 0.002 | −0.634 |
| 6 | 0.015 | −1.220 | 0.779 | −0.226 | −0.605 |
| 6 | 0.427 | −1.310 | 0.809 | −0.164 | −0.589 |
| 6 | 0.760 | −1.390 | 0.745 | −0.267 | −0.633 |
| 6 | 0.262 | −1.270 | 0.734 | −0.141 | −0.603 |
| 6 | 0.825 | −1.540 | 0.724 | −0.006 | −0.617 |
| 6 | 0.389 | −1.470 | 0.767 | −0.072 | −0.623 |
| 6 | −0.249 | −1.250 | 0.494 | −0.049 | −0.592 |
| 6 | 0.698 | −1.590 | 0.770 | 0.038 | −0.580 |
| 6 | 0.255 | −1.360 | 0.910 | −0.258 | −0.648 |
| 6 | 0.178 | −1.460 | 0.854 | −0.178 | −0.598 |
| 6 | 0.857 | −1.340 | 0.784 | −0.122 | −0.570 |
| 6 | 0.402 | −1.320 | 0.813 | −0.063 | −0.534 |
| 6 | 0.677 | −1.460 | 0.632 | −0.088 | −0.583 |
| 6 | 0.485 | −1.190 | 0.900 | −0.112 | −0.512 |
| 6 | 0.610 | −1.260 | 0.765 | −0.104 | −0.553 |
| 6 | 0.271 | −1.440 | 0.752 | −0.104 | −0.621 |
| 6 | 0.498 | −1.390 | 0.801 | −0.156 | −0.573 |
| 6 | 0.405 | −1.380 | 0.790 | 0.034 | −0.527 |
| 6 | 0.165 | −1.830 | 0.499 | −0.127 | −0.531 |
| 6 | 0.582 | −1.320 | 0.755 | −0.166 | −0.580 |
| 6 | 0.352 | −1.410 | 0.689 | −0.041 | −0.538 |
| 6 | 0.413 | −1.340 | 0.805 | −0.068 | −0.574 |
| 6 | 0.065 | −1.510 | 0.689 | 0.089 | −0.554 |
| 6 | 0.364 | −1.240 | 0.845 | −0.212 | −0.586 |
| 6 | 0.261 | −1.440 | 0.720 | 0.055 | −0.573 |
| 6 | 0.538 | −1.270 | 0.802 | −0.074 | −0.507 |
| 6 | 0.526 | −1.580 | 0.615 | −0.049 | −0.606 |
| 6 | 0.397 | −1.150 | 0.778 | 0.019 | −0.473 |
| 6 | 0.292 | −1.310 | 0.758 | 0.000 | −0.584 |
| 6 | 0.433 | −1.370 | 0.797 | −0.322 | −0.716 |
| 6 | 0.635 | −1.190 | 0.803 | −0.116 | −0.483 |
| 6 | −0.064 | −1.230 | 0.813 | −0.203 | −0.636 |
| 6 | 0.254 | −1.530 | 0.733 | −0.091 | −0.587 |
| 6 | 0.037 | −1.230 | 0.671 | −0.260 | −0.454 |

Principal Components of Reduced-Parameter Constituent Algorithm 2 which differentiates SILs from Normal Columnar Tissues. Results reported for calibration set:

| L | PC1 | PC2 | PC5 |
|---|---|---|---|
| 1 | 0.118 | 0.022 | 0.021 |
| 1 | 0.238 | 0.021 | −0.035 |
| 1 | 0.190 | −0.095 | 0.056 |
| 1 | 0.275 | −0.114 | 0.013 |
| 1 | 0.195 | −0.053 | 0.002 |
| 1 | −0.127 | 0.084 | 0.008 |
| 1 | 0.222 | 0.044 | 0.000 |
| 1 | 0.003 | 0.056 | −0.018 |
| 1 | −0.429 | 0.065 | 0.027 |
| 1 | 0.088 | 0.007 | −0.042 |
| 1 | 0.146 | 0.031 | 0.032 |
| 1 | −0.017 | −0.012 | −0.005 |
| 1 | 0.174 | −0.022 | −0.028 |
| 1 | −0.542 | 0.127 | 0.036 |
| 1 | −0.044 | 0.029 | 0.007 |
| 1 | 0.249 | −0.052 | −0.006 |
| 1 | 0.007 | −0.005 | −0.016 |
| 1 | 0.079 | −0.046 | −0.015 |
| 1 | 0.267 | 0.051 | 0.074 |
| 1 | 0.247 | −0.009 | 0.039 |
| 1 | 0.248 | −0.052 | −0.085 |
| 1 | 0.083 | 0.050 | −0.048 |
| 1 | 0.340 | −0.073 | 0.011 |
| 1 | 0.342 | 0.089 | 0.057 |
| 1 | 0.463 | 0.124 | 0.095 |
| 1 | 0.166 | −0.026 | 0.027 |
| 1 | −0.170 | 0.089 | 0.018 |
| 1 | 0.155 | −0.058 | −0.047 |
| 1 | 0.079 | 0.084 | −0.009 |
| 1 | −0.370 | −0.067 | 0.062 |
| 1 | 0.272 | 0.012 | −0.021 |
| 1 | 0.110 | 0.177 | 0.131 |
| 1 | 0.060 | 0.062 | −0.019 |
| 1 | 0.280 | 0.087 | 0.026 |
| 1 | 0.268 | −0.086 | −0.002 |
| 1 | 0.239 | −0.068 | −0.024 |
| 1 | 0.151 | −0.084 | −0.042 |
| 1 | 0.186 | −0.063 | −0.034 |
| 1 | −0.004 | −0.200 | 0.026 |
| 1 | 0.353 | 0.058 | 0.026 |
| 1 | 0.087 | −0.044 | 0.019 |
| 1 | 0.179 | −0.028 | 0.005 |
| 1 | 0.092 | 0.130 | −0.046 |
| 1 | 0.390 | 0.011 | 0.028 |
| 1 | 0.334 | 0.147 | 0.086 |
| 1 | −0.201 | −0.065 | 0.108 |
| 1 | 0.098 | 0.024 | −0.007 |
| 1 | 0.249 | −0.036 | −0.036 |
| 1 | 0.123 | 0.008 | −0.024 |
| 1 | 0.425 | 0.087 | −0.039 |
| 1 | 0.277 | −0.047 | 0.043 |
| 1 | 0.172 | 0.061 | 0.032 |
| 1 | 0.237 | −0.106 | −0.018 |
| 1 | 0.077 | −0.071 | −0.037 |
| 1 | 0.396 | 0.027 | −0.057 |
| 1 | 0.146 | −0.042 | −0.037 |
| 1 | 0.025 | −0.034 | −0.002 |
| 1 | 0.029 | 0.016 | 0.025 |
| 1 | 0.239 | −0.038 | −0.004 |
| 1 | 0.449 | −0.020 | −0.026 |
| 1 | 0.243 | 0.026 | −0.016 |
| 1 | 0.187 | 0.024 | −0.015 |
| 1 | 0.243 | 0.002 | −0.015 |
| 1 | 0.261 | −0.106 | −0.007 |
| 1 | 0.149 | 0.042 | −0.006 |
| 1 | 0.209 | 0.071 | 0.000 |
| 1 | 0.363 | 0.059 | 0.063 |
| 1 | 0.346 | −0.066 | 0.022 |
| 1 | 0.257 | 0.043 | 0.004 |
| 1 | 0.013 | −0.115 | 0.011 |
| 1 | 0.092 | −0.062 | 0.014 |
| 1 | 0.184 | 0.042 | −0.029 |
| 1 | −0.373 | 0.015 | −0.060 |
| 1 | 0.164 | −0.035 | −0.018 |
| 1 | 0.207 | 0.125 | 0.111 |
| 1 | 0.114 | 0.006 | −0.034 |
| 1 | 0.081 | −0.019 | −0.004 |
| 1 | 0.284 | 0.057 | 0.120 |
| 1 | 0.240 | 0.125 | 0.079 |
| 1 | 0.175 | 0.140 | 0.039 |
| 1 | 0.086 | −0.106 | 0.021 |
| 1 | 0.171 | −0.018 | 0.027 |
| 1 | −0.129 | 0.000 | −0.033 |
| 1 | −0.405 | 0.057 | 0.038 |
| 1 | 0.116 | 0.117 | −0.099 |
| 1 | 0.046 | −0.147 | −0.003 |
| 1 | 0.064 | −0.058 | 0.068 |
| 1 | 0.081 | −0.045 | −0.014 |
| 1 | 0.025 | 0.025 | −0.059 |
| 1 | 0.015 | −0.203 | 0.040 |
| 1 | 0.158 | 0.074 | −0.079 |
| 1 | 0.229 | 0.079 | 0.011 |
| 1 | 0.146 | 0.032 | −0.029 |
| 1 | −0.110 | 0.113 | −0.017 |
| 1 | −0.243 | 0.099 | −0.029 |
| 1 | −0.111 | 0.109 | 0.025 |
| 2 | −0.304 | 0.052 | 0.062 |
| 2 | −0.388 | −0.008 | 0.038 |
| 2 | −0.134 | 0.168 | 0.031 |
| 2 | −0.044 | 0.049 | −0.038 |
| 2 | −0.412 | 0.076 | 0.010 |
| 2 | −0.389 | 0.069 | 0.008 |
| 2 | −0.242 | 0.152 | −0.002 |
| 2 | −0.258 | 0.059 | 0.013 |
| 2 | −0.074 | −0.025 | 0.009 |
| 2 | −0.388 | 0.079 | 0.004 |
| 2 | −0.248 | −0.046 | −0.042 |
| 3 | −0.231 | −0.054 | 0.051 |
| 3 | −0.099 | 0.063 | 0.031 |
| 3 | −0.026 | −0.027 | −0.041 |
| 3 | −0.007 | −0.058 | −0.025 |
| 3 | 0.013 | −0.095 | 0.008 |
| 3 | −0.297 | −0.118 | 0.056 |
| 3 | −0.660 | 0.204 | 0.066 |
| 3 | 0.003 | 0.065 | −0.010 |
| 3 | −0.696 | 0.166 | 0.012 |
| 3 | −0.027 | −0.141 | 0.058 |
| 4 | −0.108 | 0.129 | −0.005 |
| 4 | −0.021 | −0.098 | 0.026 |
| 4 | −0.376 | −0.046 | −0.024 |
| 4 | −0.176 | −0.140 | 0.012 |
| 4 | −0.517 | −0.055 | 0.028 |
| 4 | −0.241 | −0.087 | −0.031 |
| 4 | −0.057 | −0.129 | −0.003 |
| 4 | −0.158 | −0.096 | 0.019 |
| 4 | −0.260 | −0.036 | −0.052 |
| 4 | 0.031 | 0.075 | −0.007 |
| 4 | 0.224 | −0.024 | 0.027 |
| 4 | −0.187 | 0.032 | 0.049 |
| 4 | −0.356 | −0.083 | −0.054 |
| 4 | 0.131 | 0.052 | −0.016 |
| 4 | −0.260 | −0.123 | 0.010 |
| 5 | 0.071 | 0.037 | −0.041 |
| 5 | −0.311 | 0.000 | 0.043 |
| 5 | 0.086 | 0.008 | 0.030 |
| 5 | −0.536 | 0.088 | 0.012 |
| 5 | −0.223 | −0.170 | −0.050 |
| 5 | −0.126 | 0.049 | −0.037 |
| 5 | −0.031 | −0.035 | −0.072 |
| 5 | 0.098 | −0.098 | 0.074 |
| 5 | −0.042 | −0.110 | 0.013 |
| 5 | −0.068 | −0.098 | 0.127 |
| 5 | −0.178 | 0.116 | 0.065 |
| 5 | −0.439 | 0.122 | −0.028 |
| 5 | −0.224 | 0.156 | 0.001 |
| 5 | −0.106 | 0.111 | −0.024 |
| 5 | −0.115 | 0.111 | −0.033 |
| 5 | −0.002 | −0.006 | −0.061 |
| 5 | −0.107 | 0.033 | 0.003 |
| 5 | 0.094 | −0.065 | 0.033 |

-continued

| L | PC1 | PC2 | PC5 |
|---|---|---|---|
| 5 | −0.038 | 0.052 | −0.144 |
| 5 | 0.300 | 0.072 | −0.012 |
| 5 | −0.122 | −0.060 | −0.001 |
| 5 | 0.092 | −0.012 | −0.002 |
| 5 | −0.145 | −0.052 | 0.026 |
| 6 | −0.157 | −0.274 | −0.011 |
| 6 | −0.295 | 0.073 | −0.065 |
| 6 | −0.173 | 0.017 | 0.006 |
| 6 | −0.021 | −0.002 | 0.017 |
| 6 | −0.157 | −0.009 | 0.046 |
| 6 | −0.066 | −0.166 | −0.028 |
| 6 | −0.165 | −0.151 | 0.059 |
| 6 | −0.581 | 0.115 | 0.014 |
| 6 | −0.190 | −0.212 | −0.011 |
| 6 | −0.226 | −0.014 | 0.047 |
| 6 | −0.259 | −0.011 | 0.013 |
| 6 | 0.092 | −0.019 | 0.013 |
| 6 | −0.079 | −0.032 | −0.007 |
| 6 | 0.112 | −0.015 | 0.036 |
| 6 | −0.116 | 0.187 | −0.076 |
| 6 | 0.117 | 0.048 | −0.009 |
| 6 | −0.028 | −0.079 | 0.007 |
| 6 | 0.075 | 0.072 | 0.009 |
| 6 | −0.197 | −0.081 | 0.022 |
| 6 | −0.477 | −0.439 | −0.113 |
| 6 | 0.097 | −0.037 | −0.012 |
| 6 | −0.157 | −0.019 | −0.019 |
| 6 | −0.133 | −0.010 | 0.015 |
| 6 | −0.525 | −0.174 | −0.121 |
| 6 | 0.025 | −0.008 | 0.011 |
| 6 | −0.100 | −0.314 | 0.069 |
| 6 | −0.003 | 0.034 | −0.007 |
| 6 | 0.137 | −0.049 | −0.018 |
| 6 | −0.024 | 0.142 | −0.038 |
| 6 | −0.143 | −0.011 | −0.045 |
| 6 | −0.232 | 0.011 | −0.195 |
| 6 | −0.007 | 0.023 | −0.085 |
| 6 | −0.110 | 0.073 | 0.136 |
| 6 | −0.137 | 0.049 | 0.018 |
| 6 | 0.035 | −0.101 | −0.044 |

Principal Components of Reduced-Parameter Constituent Algorithm 3 which differentiates HG SILs from LG SILs. Results reported for calibration set:

| L | PC1 | PC3 | PC4 | PC7 | PC8 |
|---|---|---|---|---|---|
| 1 | 0.748 | 0.432 | −0.128 | −0.304 | 0.052 |
| 1 | 0.747 | 0.432 | −0.128 | −0.281 | 0.032 |
| 1 | 0.857 | 0.644 | −0.281 | −0.223 | −0.014 |
| 1 | 0.937 | 0.678 | −0.111 | −0.172 | 0.008 |
| 1 | 0.513 | 0.791 | −0.172 | −0.254 | 0.075 |
| 1 | 0.150 | 0.803 | −0.165 | −0.271 | 0.013 |
| 1 | 0.828 | 0.772 | −0.179 | −0.232 | 0.077 |
| 1 | 0.768 | 0.870 | −0.187 | −0.229 | 0.074 |
| 1 | 0.334 | 0.819 | −0.183 | −0.214 | 0.086 |
| 1 | 0.929 | 0.657 | −0.183 | −0.175 | 0.017 |
| 1 | 0.989 | 0.676 | −0.143 | −0.192 | 0.039 |
| 1 | 0.584 | 0.789 | −0.170 | −0.191 | 0.032 |
| 1 | 0.807 | 0.716 | −0.165 | −0.186 | 0.061 |
| 1 | −0.221 | 0.509 | −0.117 | −0.193 | 0.006 |
| 1 | 0.729 | 0.699 | −0.146 | −0.164 | −0.011 |
| 1 | 0.969 | 0.646 | −0.158 | −0.243 | 0.051 |
| 1 | 0.701 | 0.734 | −0.056 | −0.198 | 0.045 |
| 1 | 0.773 | 0.722 | −0.071 | −0.173 | 0.048 |
| 1 | 0.878 | 0.697 | −0.173 | −0.207 | 0.061 |
| 1 | 0.766 | 0.535 | −0.141 | −0.252 | 0.031 |
| 1 | 0.645 | 0.690 | −0.125 | −0.159 | 0.030 |
| 1 | 0.741 | 0.386 | −0.060 | −0.187 | 0.026 |
| 1 | 0.972 | 0.761 | −0.146 | −0.177 | 0.032 |
| 1 | 0.680 | 0.774 | −0.179 | −0.173 | −0.008 |
| 1 | 0.993 | 0.718 | −0.213 | −0.176 | 0.021 |
| 1 | 0.848 | 0.819 | −0.130 | −0.191 | 0.019 |
| 1 | 0.316 | 0.794 | −0.125 | −0.281 | 0.117 |
| 1 | 0.579 | 0.730 | −0.077 | −0.253 | 0.043 |
| 1 | 0.738 | 0.851 | −0.083 | −0.222 | 0.022 |
| 1 | 0.303 | 0.816 | 0.046 | −0.252 | 0.020 |
| 1 | 0.862 | 0.736 | −0.124 | −0.213 | 0.054 |
| 1 | 0.975 | 0.635 | −0.116 | −0.166 | 0.056 |
| 1 | 0.935 | 0.763 | −0.065 | −0.199 | 0.032 |
| 1 | 0.897 | 0.703 | −0.111 | −0.214 | 0.063 |
| 1 | 0.697 | 0.821 | −0.085 | −0.210 | 0.052 |
| 1 | 0.789 | 0.724 | −0.075 | −0.205 | 0.049 |
| 1 | 0.701 | 0.700 | −0.073 | −0.166 | 0.025 |
| 1 | 0.676 | 0.765 | −0.110 | −0.149 | 0.018 |
| 1 | 0.433 | 0.666 | 0.109 | −0.136 | 0.032 |
| 1 | 0.910 | 0.776 | −0.315 | −0.154 | 0.016 |
| 1 | 0.557 | 0.781 | −0.099 | −0.220 | 0.041 |
| 1 | 0.923 | 0.873 | −0.105 | −0.146 | 0.044 |
| 1 | 0.628 | 0.845 | −0.101 | −0.248 | 0.048 |
| 1 | 1.060 | 0.705 | −0.141 | −0.167 | 0.050 |
| 1 | 0.897 | 0.598 | −0.167 | −0.198 | 0.053 |
| 1 | 0.143 | 0.845 | −0.269 | −0.243 | 0.063 |
| 1 | 0.635 | 0.807 | −0.185 | −0.218 | 0.032 |
| 1 | 0.867 | 0.763 | −0.069 | −0.180 | 0.047 |
| 1 | 0.771 | 0.769 | −0.051 | −0.227 | 0.054 |
| 1 | 0.763 | 0.681 | −0.114 | −0.185 | 0.040 |
| 1 | 1.060 | 0.697 | −0.135 | −0.152 | 0.042 |
| 1 | 1.040 | 0.754 | −0.143 | −0.162 | 0.049 |
| 1 | 0.898 | 0.724 | −0.096 | −0.164 | 0.022 |
| 1 | 0.558 | 0.789 | −0.059 | −0.246 | 0.035 |
| 1 | 0.668 | 0.771 | −0.192 | −0.236 | 0.012 |
| 1 | 0.582 | 0.713 | 0.020 | −0.188 | 0.026 |
| 1 | 0.771 | 0.656 | −0.164 | −0.163 | 0.065 |
| 1 | 0.635 | 0.691 | −0.059 | −0.154 | 0.021 |
| 1 | 0.854 | 0.686 | −0.126 | −0.151 | 0.025 |
| 1 | 0.876 | 0.640 | −0.142 | −0.171 | 0.003 |
| 1 | 0.679 | 0.784 | 0.006 | −0.245 | 0.046 |
| 1 | 0.690 | 0.834 | −0.146 | −0.232 | 0.035 |
| 1 | 0.711 | 0.753 | −0.096 | −0.184 | 0.067 |
| 1 | 0.694 | 0.677 | −0.099 | −0.267 | 0.044 |
| 1 | 0.812 | 0.545 | −0.188 | −0.228 | 0.083 |
| 1 | 0.671 | 0.754 | −0.054 | −0.210 | 0.059 |
| 1 | 0.869 | 0.844 | −0.337 | −0.190 | 0.049 |
| 1 | 1.000 | 0.724 | −0.160 | −0.220 | 0.042 |
| 1 | 0.860 | 0.693 | −0.166 | −0.203 | 0.027 |
| 1 | 0.476 | 0.738 | 0.152 | −0.252 | 0.040 |
| 1 | 0.804 | 0.728 | −0.141 | −0.229 | 0.005 |
| 1 | 0.729 | 0.790 | −0.069 | −0.184 | 0.056 |
| 1 | 0.167 | 0.671 | −0.096 | −0.196 | 0.078 |
| 1 | 0.929 | 0.733 | −0.087 | −0.182 | 0.015 |
| 1 | 0.933 | 0.651 | −0.113 | −0.140 | 0.035 |
| 1 | 0.581 | 0.710 | −0.182 | −0.189 | 0.026 |
| 1 | 0.655 | 0.765 | −0.077 | −0.175 | 0.022 |
| 1 | 0.921 | 0.652 | −0.187 | −0.134 | 0.057 |
| 1 | 0.753 | 0.620 | −0.111 | −0.150 | 0.059 |
| 1 | 0.730 | 0.687 | −0.124 | −0.156 | 0.047 |
| 1 | 0.615 | 0.692 | −0.014 | −0.194 | 0.086 |
| 1 | 0.640 | 0.655 | −0.012 | −0.197 | 0.053 |
| 1 | 0.155 | 0.583 | −0.225 | −0.285 | 0.020 |
| 1 | −0.120 | 0.592 | −0.191 | −0.257 | 0.052 |
| 1 | 0.694 | 0.727 | −0.123 | −0.111 | 0.012 |
| 1 | 0.556 | 0.645 | −0.043 | −0.189 | 0.026 |
| 1 | −0.245 | 0.594 | −0.170 | −0.183 | 0.030 |
| 1 | 0.126 | 0.639 | −0.083 | −0.304 | 0.065 |
| 1 | 0.726 | 0.668 | −0.131 | −0.153 | 0.055 |
| 1 | 0.633 | 0.669 | −0.076 | −0.202 | 0.052 |
| 1 | 0.879 | 0.732 | −0.224 | −0.150 | 0.048 |
| 1 | 0.898 | 0.606 | −0.183 | −0.163 | 0.012 |
| 1 | 0.641 | 0.788 | −0.113 | −0.198 | 0.044 |
| 1 | −0.132 | 0.564 | −0.168 | −0.220 | 0.026 |
| 2 | 0.407 | 0.803 | −0.116 | −0.236 | 0.019 |
| 2 | 0.494 | 0.841 | −0.228 | −0.215 | 0.088 |
| 2 | 0.474 | 0.762 | −0.273 | −0.165 | −0.025 |
| 2 | 0.009 | 0.734 | −0.455 | −0.235 | 0.006 |
| 2 | 0.254 | 0.903 | −0.364 | −0.250 | 0.029 |
| 2 | 0.496 | 0.868 | −0.143 | −0.251 | 0.048 |
| 2 | −0.170 | 0.642 | 0.053 | −0.182 | 0.033 |
| 2 | 0.179 | 0.977 | −0.370 | −0.191 | 0.081 |

-continued

| L | PC1 | PC3 | PC4 | PC7 | PC8 |
|---|---|---|---|---|---|
| 2 | 0.490 | 0.905 | −0.200 | −0.187 | 0.089 |
| 2 | 0.383 | 0.739 | −0.193 | −0.216 | 0.066 |
| 2 | 0.585 | 0.819 | −0.163 | −0.209 | 0.060 |
| 2 | 0.376 | 0.890 | −0.186 | −0.235 | 0.030 |
| 2 | 0.403 | 0.785 | −0.018 | −0.141 | 0.036 |
| 3 | −0.201 | 0.489 | −0.004 | −0.120 | 0.018 |
| 3 | 0.590 | 0.739 | −0.071 | −0.266 | 0.060 |
| 3 | 0.593 | 0.751 | −0.082 | −0.214 | 0.036 |
| 3 | 0.658 | 0.373 | −0.144 | −0.215 | 0.064 |
| 3 | 0.520 | 0.890 | −0.003 | −0.197 | 0.075 |
| 3 | 0.279 | 0.839 | −0.186 | −0.219 | 0.000 |
| 3 | −0.062 | 0.662 | −0.004 | −0.218 | −0.037 |
| 3 | 0.657 | 0.849 | −0.085 | −0.260 | 0.031 |
| 3 | −0.090 | 0.788 | −0.163 | −0.164 | −0.063 |
| 3 | 0.533 | 0.769 | 0.040 | −0.221 | 0.048 |
| 4 | 0.549 | 0.801 | −0.188 | −0.269 | 0.003 |
| 4 | 0.270 | 0.864 | −0.182 | −0.217 | −0.049 |
| 4 | 0.241 | 0.882 | −0.166 | −0.156 | 0.065 |
| 4 | 0.455 | 0.764 | −0.005 | −0.233 | 0.054 |
| 4 | −0.119 | 0.636 | −0.180 | −0.140 | 0.016 |
| 4 | 0.162 | 0.753 | −0.179 | −0.159 | 0.040 |
| 4 | 0.610 | 0.285 | −0.158 | −0.228 | 0.068 |
| 4 | 0.394 | 0.826 | −0.039 | −0.232 | 0.028 |
| 4 | −0.007 | 0.706 | 0.034 | −0.163 | 0.062 |
| 4 | 0.494 | 0.818 | −0.195 | −0.259 | 0.031 |
| 4 | 0.999 | 0.673 | −0.154 | −0.135 | 0.046 |
| 4 | 0.243 | 0.784 | −0.140 | −0.259 | 0.081 |
| 4 | 0.102 | 0.656 | 0.177 | −0.171 | 0.064 |
| 4 | 0.176 | 0.687 | −0.058 | −0.244 | 0.054 |
| 4 | 0.444 | 0.540 | −0.059 | −0.266 | −0.008 |
| 5 | 0.731 | 0.721 | −0.247 | −0.203 | 0.018 |
| 5 | 0.004 | 0.744 | −0.204 | −0.144 | 0.012 |
| 5 | 0.864 | 0.667 | −0.177 | −0.183 | 0.050 |
| 5 | −0.023 | 0.653 | −0.274 | −0.144 | −0.129 |
| 5 | 0.671 | 0.729 | 0.059 | −0.158 | 0.048 |
| 5 | 0.622 | 0.823 | −0.079 | −0.172 | 0.052 |
| 5 | 0.495 | 0.677 | −0.069 | −0.142 | 0.045 |
| 5 | 0.759 | 0.780 | −0.097 | −0.250 | 0.025 |
| 5 | 0.581 | 0.835 | −0.080 | −0.207 | 0.035 |
| 5 | 0.782 | 0.539 | −0.088 | −0.211 | 0.007 |
| 5 | 0.242 | 0.812 | −0.253 | −0.244 | 0.067 |
| 5 | −0.019 | 0.932 | −0.074 | −0.118 | −0.131 |
| 5 | 0.194 | 0.990 | −0.170 | −0.168 | −0.026 |
| 5 | 0.682 | 1.080 | −0.110 | −0.099 | 0.095 |
| 5 | 0.750 | 0.848 | −0.108 | −0.183 | 0.016 |
| 5 | 0.274 | 0.748 | −0.135 | −0.177 | −0.021 |
| 5 | 0.510 | 0.785 | −0.090 | −0.151 | 0.033 |
| 5 | 0.533 | 0.781 | −0.053 | −0.257 | 0.069 |
| 5 | 0.468 | 0.903 | −0.216 | −0.185 | 0.049 |
| 5 | 0.747 | 0.733 | 0.027 | −0.273 | 0.027 |
| 5 | 0.593 | 0.746 | 0.072 | −0.242 | 0.035 |
| 5 | 0.570 | 0.841 | −0.065 | −0.162 | 0.041 |
| 5 | 0.451 | 0.709 | −0.052 | −0.199 | 0.006 |
| 6 | 0.499 | 0.458 | 0.002 | −0.240 | 0.081 |
| 6 | 0.015 | 0.779 | −0.226 | −0.126 | 0.069 |
| 6 | 0.427 | 0.809 | −0.164 | −0.204 | 0.055 |
| 6 | 0.760 | 0.745 | −0.267 | −0.175 | 0.051 |
| 6 | 0.262 | 0.734 | −0.141 | −0.294 | −0.078 |
| 6 | 0.825 | 0.724 | −0.006 | −0.153 | 0.040 |
| 6 | 0.389 | 0.767 | −0.072 | −0.268 | 0.073 |
| 6 | −0.249 | 0.494 | −0.049 | −0.104 | 0.052 |
| 6 | 0.698 | 0.770 | 0.038 | −0.118 | 0.030 |
| 6 | 0.255 | 0.910 | −0.258 | −0.261 | 0.024 |
| 6 | 0.178 | 0.854 | −0.178 | −0.207 | 0.024 |
| 6 | 0.857 | 0.784 | −0.122 | −0.242 | 0.050 |
| 6 | 0.402 | 0.813 | −0.063 | −0.157 | 0.043 |
| 6 | 0.677 | 0.632 | −0.088 | −0.153 | 0.052 |
| 6 | 0.485 | 0.900 | −0.112 | −0.182 | 0.083 |
| 6 | 0.610 | 0.765 | −0.104 | −0.241 | 0.046 |
| 6 | 0.271 | 0.752 | −0.104 | −0.250 | 0.024 |
| 6 | 0.498 | 0.801 | −0.156 | −0.235 | 0.047 |
| 6 | 0.405 | 0.790 | 0.034 | −0.223 | 0.055 |
| 6 | 0.165 | 0.499 | −0.127 | −0.037 | 0.107 |
| 6 | 0.582 | 0.755 | −0.166 | −0.159 | 0.039 |
| 6 | 0.352 | 0.689 | −0.041 | −0.145 | 0.039 |
| 6 | 0.413 | 0.805 | −0.068 | −0.245 | 0.067 |
| 6 | 0.065 | 0.689 | 0.089 | −0.153 | 0.038 |

-continued

| L | PC1 | PC3 | PC4 | PC7 | PC8 |
|---|---|---|---|---|---|
| 6 | 0.364 | 0.845 | −0.212 | −0.256 | 0.079 |
| 6 | 0.261 | 0.720 | 0.055 | −0.232 | 0.054 |
| 6 | 0.538 | 0.802 | −0.074 | −0.253 | 0.071 |
| 6 | 0.526 | 0.615 | −0.049 | −0.174 | 0.050 |
| 6 | 0.397 | 0.778 | 0.019 | −0.201 | 0.059 |
| 6 | 0.292 | 0.758 | 0.000 | −0.217 | 0.052 |
| 6 | 0.433 | 0.797 | −0.322 | −0.248 | 0.037 |
| 6 | 0.635 | 0.803 | −0.116 | −0.195 | 0.064 |
| 6 | −0.064 | 0.813 | −0.203 | −0.183 | −0.045 |
| 6 | 0.254 | 0.733 | −0.091 | −0.194 | 0.050 |
| 6 | 0.037 | 0.671 | −0.260 | −0.106 | 0.115 |

APPENDIX D: PRINCIPAL COMPONENTS

| 337 nm excitation | | 460 nm excitation | | 380 excitation | | 460 excitation | |
|---|---|---|---|---|---|---|---|
| E1 | E2 | E1 | E2 | E2 | E5 | E4 | E7 |
| 0.12 | 0.11 | −0.147 | −0.275 | −0.615 | 0.532 | 0.69 | 0.10 |
| 0.17 | 0.12 | −0.093 | −0.319 | −0.464 | −0.151 | 0.09 | −0.07 |
| 0.22 | 0.12 | −0.074 | −0.360 | −0.378 | −0.1 | −0.14 | −0.17 |
| 0.25 | 0.11 | −0.056 | −0.345 | −0.317 | −0.308 | −0.23 | −0.07 |
| 0.27 | 0.1 | −0.027 | −0.314 | −0.236 | −0.373 | −0.24 | 0.06 |
| 0.28 | 0.11 | −0.004 | −0.253 | −0.157 | −0.348 | −0.23 | 0.04 |
| 0.28 | 0.12 | 0.010 | −0.193 | −0.086 | −0.236 | −0.19 | 0.01 |
| 0.28 | 0.12 | 0.024 | −0.121 | −0.04 | −0.161 | −0.15 | 0.00 |
| 0.28 | 0.11 | 0.029 | −0.048 | −0.004 | −0.071 | −0.09 | −0.05 |
| 0.26 | 0.11 | 0.016 | 0.030 | 0.025 | −0.055 | −0.01 | −0.07 |
| 0.24 | 0.11 | −0.001 | 0.097 | 0.044 | 0.013 | 0.06 | −0.07 |
| 0.22 | 0.11 | −0.026 | 0.153 | 0.06 | 0.068 | 0.12 | 0.24 |
| 0.2 | 0.09 | −0.052 | 0.201 | 0.06 | 0.108 | 0.14 | 0.40 |
| 0.17 | 0.08 | −0.025 | 0.203 | 0.055 | 0.123 | 0.16 | 0.30 |
| 0.13 | 0.05 | 0.019 | 0.192 | 0.046 | 0.159 | 0.16 | 0.04 |
| 0.09 | 0.04 | 0.062 | 0.160 | 0.023 | 0.133 | 0.16 | −0.12 |
| 0.06 | 0.04 | 0.090 | 0.153 | 0.006 | 0.15 | 0.14 | −0.18 |
| 0.02 | 0.05 | 0.091 | 0.153 | −0.014 | 0.089 | 0.14 | −0.14 |
| −0.01 | 0.05 | 0.088 | 0.164 | −0.026 | 0.075 | 0.16 | −0.24 |
| −0.04 | 0.05 | 0.087 | 0.158 | −0.044 | 0.047 | 0.17 | −0.23 |
| −0.06 | 0.05 | 0.106 | 0.146 | −0.055 | 0.025 | 0.17 | −0.16 |
| −0.08 | 0.07 | 0.145 | 0.092 | −0.063 | −0.018 | 0.11 | −0.12 |
| −0.09 | 0.09 | 0.189 | 0.020 | −0.071 | −0.089 | 0.05 | −0.18 |
| −0.1 | 0.11 | 0.218 | −0.023 | −0.072 | −0.102 | 0.01 | −0.09 |
| −0.11 | 0.13 | 0.240 | −0.054 | −0.078 | −0.104 | −0.02 | 0.11 |
| −0.11 | 0.15 | 0.249 | −0.060 | −0.071 | −0.078 | −0.04 | 0.04 |
| −0.12 | 0.17 | 0.242 | −0.073 | −0.071 | −0.091 | −0.03 | −0.06 |
| −0.12 | 0.18 | 0.238 | −0.075 | −0.066 | −0.087 | −0.02 | 0.08 |
| −0.12 | 0.2 | 0.240 | −0.064 | −0.062 | −0.095 | −0.03 | 0.15 |
| −0.11 | 0.2 | 0.230 | −0.063 | −0.06 | −0.08 | −0.03 | 0.18 |
| −0.1 | 0.21 | 0.221 | −0.061 | −0.057 | −0.067 | −0.03 | 0.19 |
| −0.09 | 0.22 | 0.211 | −0.060 | −0.048 | −0.086 | −0.02 | 0.25 |
| −0.08 | 0.22 | 0.204 | −0.052 | −0.039 | −0.068 | −0.01 | 0.26 |
| −0.07 | 0.21 | 0.199 | −0.045 | −0.031 | −0.039 | 0.00 | 0.17 |
| −0.07 | 0.21 | 0.185 | −0.044 | −0.027 | −0.034 | 0.01 | 0.10 |
| −0.07 | 0.2 | 0.181 | −0.045 | −0.019 | −0.028 | 0.01 | 0.03 |
| −0.06 | 0.2 | 0.176 | −0.042 | −0.019 | −0.032 | 0.00 | −0.02 |
| −0.06 | 0.19 | 0.170 | −0.037 | −0.015 | −0.01 | 0.00 | −0.01 |
| −0.06 | 0.18 | 0.167 | −0.035 | −0.008 | −0.039 | 0.01 | −0.12 |
| −0.05 | 0.17 | 0.159 | −0.030 | −0.008 | −0.037 | 0.03 | −0.13 |
| −0.05 | 0.16 | 0.158 | −0.032 | −0.01 | −0.068 | 0.01 | −0.21 |
| −0.05 | 0.15 | 0.151 | −0.027 | −0.009 | −0.085 | 0.01 | 0.00 |
| −0.05 | 0.14 | 0.146 | −0.027 | −0.005 | −0.095 | 0.00 | −0.03 |
| −0.05 | 0.13 | 0.137 | −0.019 | −0.01 | −0.069 | 0.01 | 0.03 |
| −0.05 | 0.12 | 0.128 | −0.015 | −0.007 | −0.084 | 0.01 | 0.03 |
| −0.05 | 0.11 | | | −0.012 | −0.034 | | |
| −0.05 | 0.1 | | | −0.012 | −0.036 | | |
| −0.04 | 0.11 | | | | | | |
| −0.04 | 0.09 | | | | | | |
| −0.04 | 0.09 | | | | | | |
| −0.03 | 0.09 | | | | | | |
| −0.03 | 0.09 | | | | | | |

-continued

| 337 nm excitation | | 460 nm excitation | | 380 excitation | | 460 excitation | |
|---|---|---|---|---|---|---|---|
| E1 | E2 | E1 | E2 | E2 | E5 | E4 | E7 |
| −0.03 | 0.08 | | | | | | |
| −0.03 | 0.08 | | | | | | |
| −0.03 | 0.08 | | | | | | |
| −0.02 | 0.09 | | | | | | |
| −0.02 | 0.12 | | | | | | |

The invention claimed is:

1. A method of probabilistically classifying a sample of tissue of a mammalian anatomical structure, tissues of which may have various morphological and biochemical states and are classifiable in accordance therewith, comprising:
   illuminating the tissue sample with electromagnetic radiation of a first wavelength selected to stimulate in tissues of the mammalian anatomical structure a fluorescence having spectral characteristics indicative of a first classification thereof;
   detecting a first fluorescence intensity spectrum from the tissue sample resulting from the first wavelength illuminating step; and
   calculating a first probability that the tissue sample belongs in the first classification from a data set comprising the first fluorescence intensity spectrum.

2. The method of claim 1, wherein the first wavelength is within one of the ranges of 317-357 nm, 360-400 nm and 440-480 nm.

3. The method of claim 1 wherein the first fluorescence intensity spectrum comprises emission wavelengths of about 410 nm, about 460 nm, about 510 nm and about 580 nm when the first wavelength is about 337 nm; about 460 nm, about 510 nm, about 580 nm, about 600 nm and about 640 nm when the first wavelength is about 380 nm; and about 510, about 580 nm, about 600 nm, about 620 nm, about 640 nm and about 660 nm when the first wavelength is about 460 nm.

4. A method as in claim 1, further comprising:
   illuminating the tissue sample with electromagnetic radiation of a second wavelength selected to stimulate in tissues of the mammalian anatomical structure a fluorescence having spectral characteristics indicative of a second classification thereof;
   detecting a second fluorescence intensity spectrum from the tissue sample resulting from the second wavelength illuminating step;
   calculating a second probability that the tissue sample belongs in the second classification from a data set comprising the second fluorescence intensity spectrum; and
   classifying the tissue sample in the second classification if the first and second probabilities exceed respective thresholds.

5. The method of claim 4 wherein the first probability calculating step comprises:
   providing a statistically significant first plurality of tissue samples, at least some of which are tissues known to belong to the first classification;
   illuminating the first plurality of tissue samples with the first wavelength electromagnetic radiation;
   detecting a first plurality of fluorescence intensity spectra from the first plurality of tissue samples;
   generating first vectors that account for variation in the first plurality of fluorescence intensity spectra and that are indicative of the first classification;
   calculating the first probability from the data set comprising the first fluorescence intensity spectrum, with use of the first vectors;
   and wherein the second probability calculating step comprises:
   providing a statistically significant second plurality of tissue samples, at least some of which are tissues known to belong to the second classification;
   illuminating the second plurality of tissue samples with the second wavelength electromagnetic radiation;
   detecting a second plurality of fluorescence intensity spectra from the second plurality of tissue samples;
   generating second vectors that account for variation in the second plurality of fluorescence intensity spectra and that are indicative of the second classification; and
   calculating the second probability from the data set comprising the second fluorescence intensity spectrum, with use of the second vectors.

6. A method as in claim 1, further comprising:
   illuminating the tissue sample with electromagnetic radiation of a second wavelength selected to stimulate in tissues of the mammalian anatomical structure a fluorescence having spectral characteristics indicative of a second classification thereof;
   detecting a second fluorescence intensity spectrum from the tissue sample resulting from the second wavelength illuminating step;
   calculating a second probability that the tissue sample belongs in the second classification from a data set comprising the second fluorescence intensity spectrum;
   illuminating the tissue sample with electromagnetic radiation of a third wavelength selected to stimulate in tissues of the mammalian anatomical structure a fluorescence having spectral characteristics indicative of a third classification thereof;
   detecting a third fluorescence intensity spectrum from the tissue sample resulting from the third wavelength illuminating step;
   calculating a third probability that the tissue sample belongs in the third classification from a data set comprising the third fluorescence intensity spectrum; and
   classifying the tissue sample in the second classification if the third, first and second probabilities exceed respective thresholds.

7. A method as in claim 6, wherein:
   the third classification is SIL as distinguished from normal squamous, and the wavelength selected to stimulate in tissues of the mammalian anatomical structure a fluorescence having spectral characteristics indicative of the third classification thereof is selected for cervical tissues from 337 nm and 460 nm;
   the first classification is SIL as distinguished from normal columnar and inflammation, and the wavelength selected to stimulate in tissues of the mammalian anatomical structure a fluorescence having spectral characteristics indicative of the first classification thereof is 380 nm for cervical tissues; and
   the second classification is high grade SIL as distinguished from low grade SIL, and the wavelength selected to stimulate in tissues of the mammalian anatomical structure a fluorescence having spectral characteristics indicative of the first classification thereof is 460 nm for cervical tissues.

8. The method of claim 6 wherein the first probability calculating step comprises:
providing a statistically significant first plurality of tissue samples, at least some of which are tissues known to belong to the first classification;
illuminating the first plurality of tissue samples with the first wavelength electromagnetic radiation;
detecting a first plurality of fluorescence intensity spectra from the first plurality of tissue samples;
generating first vectors that account for variation in the first plurality of fluorescence intensity spectra and that are indicative of the first classification;
calculating the first probability from the data set comprising the first fluorescence intensity spectrum, with use of the first vectors;
wherein the second probability calculating step comprises:
providing a statistically significant second plurality of tissue samples, at least some of which are tissues known to belong to the second classification;
illuminating the second plurality of tissue samples with the second wavelength electromagnetic radiation;
detecting a second plurality of fluorescence intensity spectra from the second plurality of tissue samples;
generating second vectors that account for variation in the second plurality of fluorescence intensity spectra and that are indicative of the second classification; and
calculating the second probability from the data set comprising the second fluorescence intensity spectrum, with use of the second vectors;
and wherein the third probability calculating step comprises:
providing a statistically significant third plurality of tissue samples, at least some of which are tissues known to belong to the third classification;
illuminating the third plurality of tissue samples with the third wavelength electromagnetic radiation;
detecting a third plurality of fluorescence intensity spectra from the third plurality of tissue samples;
generating third vectors that account for variation in the second plurality of fluorescence intensity spectra and that are indicative of the second classification; and
calculating the third probability from the data set comprising the third fluorescence intensity spectrum, with use of the third vectors.

9. A method as in claim 1 further comprising:
illuminating the tissue sample with electromagnetic radiation of a second wavelength selected to stimulate in tissues of the mammalian anatomical structure a fluorescence having spectral characteristics indicative of a first classification thereof; and
detecting a second fluorescence intensity spectrum from the tissue sample resulting from the second wavelength illuminating step;
wherein the calculating step comprises calculating the first probability from a data set comprising the first and second fluorescence intensity spectrum.

10. A method as in claim 9 further comprising:
illuminating the tissue sample with electromagnetic radiation of a third wavelength selected to stimulate in tissues of the mammalian anatomical structure a fluorescence having spectral characteristics indicative of a first classification thereof; and
detecting a third fluorescence intensity spectrum from the tissue sample resulting from the second wavelength illuminating step;
wherein the calculating step comprises calculating the first probability from a data set comprising the first, second and third fluorescence intensity spectrum.

11. A method as in claim 10 wherein the electromagnetic radiation of the first, second and third wavelengths further is selected to stimulate in tissues of the mammalian anatomical structure a fluorescence having spectral characteristics indicative of a second classification thereof, further comprising calculating a second probability that the tissue sample belongs in the second classification from a data set comprising the first, second and third fluorescence intensity spectrum.

12. A method as in claim 11 wherein the electromagnetic radiation of the first, second and third wavelengths further is selected to stimulate in tissues of the mammalian anatomical structure a fluorescence having spectral characteristics indicative of a third classification thereof, further comprising calculating a third probability that the tissue sample belongs in the third classification from a data set comprising the first, second and third fluorescence intensity spectrum.

13. A method as in claim 12, wherein:
the first wavelength is about 337 nm;
the second wavelength is about 380 nm;
the third wavelength is about 460 nm;
the third classification is SIL as distinguished from normal squamous;
the first classification is SIL as distinguished from normal columnar; and
the second classification is high grade SIL as distinguished from low grade SIL.

14. The method of claim 10 wherein the step of calculating the first probability from a data set comprising the first, second and third fluorescence intensity spectrum comprises:
providing a statistically significant plurality of additional tissue samples, at least some of which are tissues known to belong to the first classification;
illuminating the additional tissue samples with the first wavelength electromagnetic radiation;
detecting a first plurality of fluorescence intensity spectra from the additional tissue samples illuminated in the first wavelength illuminating step;
illuminating the additional tissue samples with the second wavelength electromagnetic radiation;
detecting a second plurality of fluorescence intensity spectra from the additional tissue samples illuminated in the second wavelength illuminating step;
illuminating the additional tissue samples with the third wavelength electromagnetic radiation;
detecting a third plurality of fluorescence intensity spectra from the additional tissue samples illuminated in the second wavelength illuminating step;
generating vectors that account for variation in the first, second and third pluralities of fluorescence intensity spectra and that are indicative of the first classification; and
calculating the first probability from the data set comprising the first fluorescence intensity spectrum, with use of the vectors.

15. The method of claim 9 wherein the step of calculating the first probability from a data set comprising the first and second fluorescence intensity spectrum comprises:
providing a statistically significant plurality of additional tissue samples, at least some of which are tissues known to belong to the first classification;
illuminating the additional tissue samples with the first wavelength electromagnetic radiation;

detecting a first plurality of fluorescence intensity spectra from the additional tissue samples illuminated in the first wavelength illuminating step;

illuminating the additional tissue samples with the second wavelength electromagnetic radiation;

detecting a second plurality of fluorescence intensity spectra from the additional tissue samples illuminated in the second wavelength illuminating step;

generating vectors that account for variation in the first and second pluralities of fluorescence intensity spectra and that are indicative of the first classification; and calculating the first probability from the data set comprising the first fluorescence intensity spectrum, with use of the vectors.

16. A method as in claim 1 wherein the calculating step comprises calculating a probability from the first fluorescence intensity spectrum that the tissue is SIL versus normal squamous.

17. A method as in claim 16 wherein the illuminating step comprises illuminating the tissue sample with electromagnetic radiation having a wavelength of about 337 nm.

18. A method as in claim 16 wherein the illuminating step comprises illuminating the tissue sample with electromagnetic radiation having a wavelength of about 460 nm.

19. A method as in claim 1 wherein the calculating step comprises calculating a probability from the first fluorescence intensity spectrum that the tissue is SIL versus normal columnar and inflammation.

20. A method as in claim 19 wherein the illuminating step comprises illuminating the tissue sample with electromagnetic radiation having a wavelength of about 380 nm.

21. A method as in claim 1 wherein the calculating step comprises calculating a probability from the first fluorescence intensity spectrum that the tissue is high grade SIL versus low grade SIL.

22. A method as in claim 21 wherein the illuminating step comprises illuminating the tissue with electromagnetic radiation having a wavelength of about 460 nm.

23. The method of claim 1 wherein the illuminating step is performed in vivo.

24. The method of claim 1 wherein the illuminating step is performed in vitro.

25. The method of claim 1 wherein the calculating step comprises:

providing a statistically significant plurality of additional tissue samples, at least some of which are tissues known to belong to the first classification;

illuminating the additional tissue samples with the first wavelength electromagnetic radiation;

detecting a plurality of additional fluorescence intensity spectra from the additional tissue samples;

generating vectors that account for variation in the additional fluorescence intensity spectra and that are indicative of the first classification; and calculating the first probability from the data set comprising the first fluorescence intensity spectrum, with use of the vectors.

26. The method of claim 25 wherein the first fluorescence intensity spectrum comprises emission wavelengths of about 410 nm, about 460 nm, about 510 nm and about 580 nm when the first wavelength is about 337 nm; about 460 nm, about 510 nm, about 580 nm, about 600 nm and about 640 nm when the first wavelength is about 380 nm; and about 510 nm, about 580 nm, about 600 nm, about 620 nm, about 640 nm and about 660 nm when the first wavelength is about 460 nm.

27. A method of assigning a probability that a tissue sample belongs to a particular tissue category, comprising:

providing a first tissue sample;

illuminating the first tissue sample with electromagnetic radiation having at least one wavelength known to excite tissue into producing a fluorescence intensity spectra containing information about whether tissue belongs to the particular tissue category;

detecting a fluorescence intensity spectra from the first tissue sample; and calculating from the fluorescence intensity spectra from the first tissue sample a probability that the tissue sample belongs to the particular tissue category.

28. A method as in claim 27 wherein the calculating step comprises:

providing a statistically significant plurality of second tissue samples, at least some of which are tissues known to belong to the particular tissue category;

illuminating the second tissue samples with the electromagnetic radiation; detecting a plurality of fluorescence intensity spectra from the second tissue samples, respectively;

calculating from the fluorescence intensity spectra from the second tissue samples a probability distribution for the second tissue samples belonging to the particular tissue category; and calculating the probability that the tissue sample belongs to the particular tissue category using the fluorescence intensity spectra from the first tissue sample and the probability distribution for the second tissue samples.

29. A method as in claim 28 wherein the probability distribution calculating step comprises:

generating a set of first vectors that account for variation in the fluorescence intensity spectra from the second tissue samples; and selecting from the first vectors a set of second vectors that are indicative of the particular tissue category, the second vectors containing first indicia of the probability distribution for the second tissue samples belonging to the particular tissue category.

30. A method as in claim 29 wherein:

the first vector generating step comprises principle component analysis;

the second vector generating step comprises a student's t-test; and the step of calculating the probability that the tissue sample belongs to the particular tissue category using the fluorescence intensity spectra from the first tissue sample and the probability distribution for the second tissue samples comprises logistic discrimination.

31. A method as in claim 27 wherein:

the illuminating step comprises illuminating the tissue sample with electromagnetic radiation having at least a first wavelength known to excite tissue into producing a fluorescence intensity spectra containing information about whether tissue belongs to a first tissue category, and a second wavelength known to excite tissue into producing a fluorescence intensity spectra containing information about whether tissue belongs to a second tissue category that is a refinement of the first tissue category;

the detecting step comprises detecting first and second fluorescence intensity spectra from the illuminating step to obtain respective first and second spectral data; and the calculating step comprises calculating from the first spectral data a first probability that the tissue sample belongs to the first tissue category, calculating from the second spectral data a second probability that the tissue sample belongs to the first tissue category, and assigning the tissue sample a probability of belonging to the second tissue category from the first and second probabilities.

32. A method as in claim 27 wherein:

the illuminating step comprises illuminating the tissue sample with electromagnetic radiation having a first wavelength of about 337 nm, a second wavelength of about 380 nm, and a third wavelength of about 460 nm; and the detecting step comprises detecting first, second and third fluorescence intensity spectra from the illuminating step to obtain respective first, second and third spectral data; and calculating from the first, second and third spectral data a probability that the tissue sample belongs to the particular tissue category.

* * * * *

UNITED STATES PATENT AND TRADEMARK OFFICE
CERTIFICATE OF CORRECTION

PATENT NO. : 7,236,815 B2  Page 1 of 1
APPLICATION NO. : 10/688152
DATED : June 26, 2007
INVENTOR(S) : Richards-Kortum et al.

It is certified that error appears in the above-identified patent and that said Letters Patent is hereby corrected as shown below:

Column 67, line 65, delete "510," and insert --510 nm,-- therefor.

Signed and Sealed this

Sixth Day of November, 2007

JON W. DUDAS
*Director of the United States Patent and Trademark Office*